US012660984B2

(12) United States Patent
Shelton, IV et al.

(10) Patent No.:  US 12,660,984 B2
(45) Date of Patent:      Jun. 23, 2026

(54) SURGICAL METHODS USING MULTI-SOURCE IMAGING

(71) Applicant: Cilag GmbH International, Zug (CH)

(72) Inventors: Frederick E. Shelton, IV, Hillsboro, OH (US); Charles J. Scheib, Loveland, OH (US)

(73) Assignee: Cilag GmbH International, Zug (CH)

(*) Notice: Subject to any disclaimer, the term of this patent is extended or adjusted under 35 U.S.C. 154(b) by 744 days.

(21) Appl. No.: 17/493,904

(22) Filed: Oct. 5, 2021

(65) Prior Publication Data

US 2023/0097906 A1      Mar. 30, 2023

Related U.S. Application Data

(60) Provisional application No. 63/249,644, filed on Sep. 29, 2021.

(51) Int. Cl.
*A61B 1/00* (2006.01)
*A61B 1/005* (2006.01)
(Continued)

(52) U.S. Cl.
CPC ........ *A61B 1/0005* (2013.01); *A61B 1/00009* (2013.01); *A61B 1/005* (2013.01);
(Continued)

(58) Field of Classification Search
CPC ... A61B 1/0005; A61B 1/00009; A61B 1/005; A61B 1/043; A61B 1/05; A61B 1/267;
(Continued)

(56) References Cited

U.S. PATENT DOCUMENTS

| | | | |
|---|---|---|---|
| 5,188,104 A | 2/1993 | Wernicke et al. | |
| 5,231,988 A | 8/1993 | Wernicke et al. | |

(Continued)

FOREIGN PATENT DOCUMENTS

| | | | |
|---|---|---|---|
| EP | 1886711 B1 | 4/2018 | |
| EP | 3305173 A1 | 4/2018 | |

(Continued)

OTHER PUBLICATIONS

International Search Report and Written Opinion received for Intl. Pat. App. No. PCT/IB2022/059077 mailed on Nov. 23, 2022. (14 pages).

(Continued)

*Primary Examiner* — Anh Tuan T Nguyen
*Assistant Examiner* — Shankar Raj Ghimire
(74) *Attorney, Agent, or Firm* — Condo Roccia Koptiw LLP

(57)      ABSTRACT

In general, devices, systems, and methods for multi-source imaging are provided. In one embodiment, a surgical method includes visualizing, with a first imaging system, a first side of a tissue wall during performance of a surgical procedure, and visualizing, with an endoscopic imaging system, a second, opposite side of the tissue wall during the performance of the surgical procedure. The first imaging system and the endoscopic imaging system are unable to directly visualize each other, and the first imaging system and the endoscopic imaging system are operatively coupled together. The method also includes guiding a first surgical instrument based on the visualization provided by the first imaging system and the visualization provided by the endoscopic imaging system, and guiding a second surgical instrument based on the visualization provided by the endoscopic imaging system and based on the visualization provided by the first imaging system.

19 Claims, 34 Drawing Sheets

(51) Int. Cl.

| | |
|---|---|
| *A61B 1/04* | (2006.01) |
| *A61B 1/05* | (2006.01) |
| *A61B 1/06* | (2006.01) |
| *A61B 1/267* | (2006.01) |
| *A61B 1/313* | (2006.01) |
| *A61B 6/03* | (2006.01) |
| *A61B 18/02* | (2006.01) |
| *A61B 18/14* | (2006.01) |
| *A61B 18/18* | (2006.01) |
| *A61B 34/20* | (2016.01) |
| *A61B 34/30* | (2016.01) |
| *A61B 90/00* | (2016.01) |
| *A61B 18/00* | (2006.01) |

(52) U.S. Cl.
CPC ............... *A61B 1/043* (2013.01); *A61B 1/05* (2013.01); *A61B 1/0638* (2013.01); *A61B 1/267* (2013.01); *A61B 1/2676* (2013.01); *A61B 1/3132* (2013.01); *A61B 6/032* (2013.01); *A61B 18/02* (2013.01); *A61B 18/1482* (2013.01); *A61B 18/1815* (2013.01); *A61B 34/20* (2016.02); *A61B 34/30* (2016.02); *A61B 90/37* (2016.02); *A61B 2018/00577* (2013.01); *A61B 2018/00648* (2013.01); *A61B 2018/00702* (2013.01); *A61B 2018/00779* (2013.01); *A61B 2018/00791* (2013.01); *A61B 2018/1861* (2013.01); *A61B 2034/2051* (2016.02); *A61B 2034/2057* (2016.02); *A61B 2034/2063* (2016.02); *A61B 2034/2065* (2016.02); *A61B 2034/301* (2016.02); *A61B 2090/3762* (2016.02); *A61B 2090/378* (2016.02)

(58) Field of Classification Search
CPC ..... A61B 1/2676; A61B 1/3132; A61B 6/032; A61B 34/20; A61B 34/30; A61B 2034/2051; A61B 2034/2057; A61B 2034/2063; A61B 2034/2065; A61B 2090/371; A61B 1/00149
See application file for complete search history.

(56) References Cited

U.S. PATENT DOCUMENTS

| | | | |
|---|---|---|---|
| 5,256,149 A | 10/1993 | Banik et al. | |
| 5,263,480 A | 11/1993 | Wernicke et al. | |
| 5,540,730 A | 7/1996 | Terry, Jr. et al. | |
| 5,558,671 A | 9/1996 | Yates | |
| 6,086,528 A | 7/2000 | Adair | |
| 6,332,089 B1* | 12/2001 | Acker ...................... | A61N 7/02 |
| | | | 128/899 |
| 6,471,172 B1 | 10/2002 | Lemke et al. | |
| 7,143,925 B2 | 12/2006 | Shelton, IV et al. | |
| 7,585,290 B2 | 9/2009 | Kathrani et al. | |
| 7,601,118 B2 | 10/2009 | Smith et al. | |
| 8,068,649 B2 | 11/2011 | Green | |
| 8,317,070 B2 | 11/2012 | Hueil et al. | |
| 8,352,026 B2 | 1/2013 | DiUbaldi | |
| 8,393,514 B2 | 3/2013 | Shelton, IV et al. | |
| 8,465,417 B2* | 6/2013 | Yamaguchi .......... | A61B 1/0005 |
| | | | 600/113 |
| 8,517,933 B2 | 8/2013 | Mohr | |
| 8,545,515 B2 | 10/2013 | Prisco et al. | |
| 8,551,115 B2 | 10/2013 | Steger et al. | |
| 8,623,028 B2 | 1/2014 | Rogers et al. | |
| 8,632,462 B2 | 1/2014 | Yoo et al. | |
| 8,636,751 B2 | 1/2014 | Albrecht et al. | |
| 8,734,478 B2 | 5/2014 | Widenhouse et al. | |
| 8,753,338 B2 | 6/2014 | Widenhouse et al. | |
| 8,771,180 B2 | 7/2014 | Mohr | |

| | | | |
|---|---|---|---|
| 8,812,100 B2 | 8/2014 | Voegele et al. | |
| 8,831,782 B2 | 9/2014 | Itkowitz | |
| 8,888,789 B2 | 11/2014 | Prisco et al. | |
| 8,919,348 B2 | 12/2014 | Williams et al. | |
| 8,961,406 B2 | 2/2015 | Ortiz et al. | |
| 9,044,606 B2 | 6/2015 | Harris et al. | |
| 9,072,535 B2 | 7/2015 | Shelton, IV et al. | |
| 9,072,536 B2 | 7/2015 | Shelton, IV et al. | |
| 9,204,879 B2 | 12/2015 | Shelton, IV | |
| 9,216,062 B2 | 12/2015 | Duque et al. | |
| 9,254,178 B2 | 2/2016 | Prisco et al. | |
| 9,274,047 B2 | 3/2016 | Velten et al. | |
| 9,283,050 B2 | 3/2016 | Prisco et al. | |
| 9,320,416 B2 | 4/2016 | Cooper et al. | |
| 9,339,341 B2 | 5/2016 | Cooper | |
| 9,358,074 B2 | 6/2016 | Schena et al. | |
| 9,393,017 B2 | 7/2016 | Flanagan et al. | |
| 9,561,038 B2 | 2/2017 | Shelton, IV et al. | |
| 9,572,481 B2 | 2/2017 | Duindam et al. | |
| 9,636,186 B2 | 5/2017 | Kumar et al. | |
| 9,757,128 B2 | 9/2017 | Baber et al. | |
| 9,833,254 B1 | 12/2017 | Barral et al. | |
| 9,962,161 B2 | 5/2018 | Scheib et al. | |
| 10,092,738 B2 | 10/2018 | Harris et al. | |
| 10,159,487 B2* | 12/2018 | Gagner ................ | A61B 17/221 |
| 10,179,024 B2 | 1/2019 | Yeung | |
| 10,206,682 B2 | 2/2019 | Bakos et al. | |
| 10,245,069 B2 | 4/2019 | Rogers et al. | |
| 10,492,788 B2 | 12/2019 | Swayze et al. | |
| 10,517,600 B2 | 12/2019 | Beisel et al. | |
| 10,569,071 B2 | 2/2020 | Harris et al. | |
| 10,607,738 B2 | 3/2020 | Davidson et al. | |
| 10,639,104 B1 | 5/2020 | Barral et al. | |
| 10,716,564 B2 | 7/2020 | Shelton, IV et al. | |
| 10,722,301 B2 | 7/2020 | Amirana et al. | |
| 10,751,117 B2 | 8/2020 | Witt et al. | |
| 10,779,831 B2 | 9/2020 | Lukin et al. | |
| 10,792,034 B2 | 10/2020 | Scheib et al. | |
| 10,856,928 B2 | 12/2020 | Shelton, IV et al. | |
| 10,925,598 B2 | 2/2021 | Scheib et al. | |
| 11,033,272 B2 | 6/2021 | Fegelman et al. | |
| 11,051,876 B2 | 7/2021 | Shelton, IV et al. | |
| 11,751,877 B2* | 9/2023 | Seddon ............ | A61B 17/06166 |
| | | | 606/153 |
| 11,864,764 B2* | 1/2024 | Tinkham .......... | A61B 17/07207 |
| 2005/0182295 A1* | 8/2005 | Soper ................... | A61B 1/2676 |
| | | | 600/117 |
| 2005/0277998 A1 | 12/2005 | Tracey et al. | |
| 2006/0195146 A1 | 8/2006 | Tracey et al. | |
| 2006/0195153 A1 | 8/2006 | DiUbaldi et al. | |
| 2007/0113860 A1 | 5/2007 | Anderson | |
| 2007/0185541 A1 | 8/2007 | DiUbaldi et al. | |
| 2008/0132962 A1 | 6/2008 | DiUbaldi et al. | |
| 2008/0147146 A1 | 6/2008 | Wahlgren et al. | |
| 2008/0312498 A1 | 12/2008 | Moll et al. | |
| 2009/0062792 A1 | 3/2009 | Vakharia et al. | |
| 2009/0132018 A1 | 5/2009 | DiUbaldi et al. | |
| 2009/0135280 A1* | 5/2009 | Johnston .............. | A61B 1/3132 |
| | | | 348/262 |
| 2009/0137868 A1* | 5/2009 | Yamaguchi ............ | A61B 1/045 |
| | | | 600/109 |
| 2009/0137893 A1* | 5/2009 | Seibel ................ | A61B 1/00172 |
| | | | 600/407 |
| 2009/0149918 A1 | 6/2009 | Krulevitch et al. | |
| 2009/0157149 A1 | 6/2009 | Wahlgren et al. | |
| 2010/0161001 A1 | 6/2010 | DiUbaldi et al. | |
| 2010/0161005 A1 | 6/2010 | Wahlgren et al. | |
| 2010/0191267 A1 | 7/2010 | Fox | |
| 2010/0239648 A1 | 9/2010 | Smith et al. | |
| 2011/0094773 A1 | 4/2011 | Bare et al. | |
| 2011/0118708 A1 | 5/2011 | Burbank et al. | |
| 2012/0150192 A1 | 6/2012 | Dachs, II et al. | |
| 2012/0209314 A1 | 8/2012 | Weir et al. | |
| 2012/0245576 A1 | 9/2012 | Epstein et al. | |
| 2013/0105545 A1 | 5/2013 | Burbank | |
| 2013/0105552 A1 | 5/2013 | Weir et al. | |
| 2013/0146643 A1 | 6/2013 | Schmid et al. | |
| 2013/0221065 A1 | 8/2013 | Aronhalt et al. | |
| 2013/0256377 A1 | 10/2013 | Schmid et al. | |

(56) References Cited

U.S. PATENT DOCUMENTS

| | | | |
|---|---|---|---|
| 2014/0066717 A1 | 3/2014 | Rogers et al. | |
| 2014/0121678 A1 | 5/2014 | Trusty et al. | |
| 2014/0253684 A1 | 9/2014 | Kumar et al. | |
| 2014/0268046 A1 | 9/2014 | Narasimha-Iyer et al. | |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0164607 A1* | 6/2015 | Ruijters | G06T 7/30 |
| | | | 382/132 |
| 2015/0238268 A1 | 8/2015 | Weir et al. | |
| 2015/0257841 A1 | 9/2015 | Dachs, II | |
| 2015/0257842 A1 | 9/2015 | Dachs, II | |
| 2015/0272575 A1 | 10/2015 | Leimbach et al. | |
| 2015/0282736 A1 | 10/2015 | Huldin et al. | |
| 2015/0320514 A1* | 11/2015 | Ahn | A61B 34/30 |
| | | | 606/130 |
| 2015/0351758 A1 | 12/2015 | Shelton, IV et al. | |
| 2016/0015469 A1 | 1/2016 | Goshayesh et al. | |
| 2016/0128782 A1 | 5/2016 | Wei et al. | |
| 2016/0256071 A1 | 9/2016 | Shelton, IV et al. | |
| 2016/0262761 A1* | 9/2016 | Beisel | A61B 17/1114 |
| 2016/0303743 A1 | 10/2016 | Rockrohr | |
| 2016/0324523 A1* | 11/2016 | Lukin | A61B 17/1114 |
| 2016/0331473 A1* | 11/2016 | Yamamura | A61B 18/1445 |
| 2017/0035425 A1 | 2/2017 | Fegelman et al. | |
| 2017/0055819 A1 | 3/2017 | Hansen et al. | |
| 2017/0071693 A1 | 3/2017 | Taylor et al. | |
| 2017/0128041 A1 | 5/2017 | Hasser et al. | |
| 2017/0128144 A1 | 5/2017 | Hasser et al. | |
| 2017/0128145 A1* | 5/2017 | Hasser | A61B 8/4245 |
| 2017/0202591 A1 | 7/2017 | Shelton, IV et al. | |
| 2017/0251900 A1 | 9/2017 | Hansen et al. | |
| 2017/0265866 A1* | 9/2017 | Ryou | A61B 17/3478 |
| 2018/0028187 A1* | 2/2018 | Gagner | A61B 17/1114 |
| 2018/0049820 A1 | 2/2018 | Widenhouse et al. | |
| 2018/0049821 A1 | 2/2018 | Shelton, IV et al. | |
| 2018/0146839 A1 | 5/2018 | Friedlander et al. | |
| 2018/0168757 A1 | 6/2018 | Bono et al. | |
| 2018/0177556 A1 | 6/2018 | Noonan | |
| 2018/0256008 A1 | 9/2018 | Nishizawa | |
| 2018/0353174 A1 | 12/2018 | Widenhouse et al. | |
| 2019/0099209 A1 | 4/2019 | Witt et al. | |
| 2019/0125431 A1 | 5/2019 | Shelton, IV et al. | |
| 2019/0125457 A1 | 5/2019 | Parihar et al. | |
| 2019/0200844 A1 | 7/2019 | Shelton, IV et al. | |
| 2019/0200905 A1 | 7/2019 | Shelton, IV et al. | |
| 2019/0200981 A1 | 7/2019 | Harris et al. | |
| 2019/0201046 A1 | 7/2019 | Shelton, IV et al. | |
| 2019/0201088 A1 | 7/2019 | Shelton, IV et al. | |
| 2019/0201114 A1 | 7/2019 | Shelton, IV et al. | |
| 2019/0201136 A1 | 7/2019 | Shelton, IV et al. | |
| 2019/0201140 A1 | 7/2019 | Yates et al. | |
| 2019/0204201 A1 | 7/2019 | Shelton, IV et al. | |
| 2019/0206004 A1 | 7/2019 | Shelton, IV et al. | |
| 2019/0206050 A1 | 7/2019 | Yates et al. | |
| 2019/0206555 A1 | 7/2019 | Morgan et al. | |
| 2019/0207857 A1 | 7/2019 | Shelton, IV et al. | |
| 2019/0290247 A1 | 9/2019 | Popovic et al. | |
| 2019/0307331 A1 | 10/2019 | Saadat et al. | |
| 2019/0343581 A1 | 11/2019 | Panescu et al. | |
| 2020/0000530 A1* | 1/2020 | DeFonzo | A61B 34/37 |
| 2020/0015668 A1 | 1/2020 | Scheib | |
| 2020/0015897 A1 | 1/2020 | Scheib et al. | |
| 2020/0015898 A1 | 1/2020 | Scheib et al. | |
| 2020/0015899 A1 | 1/2020 | Scheib et al. | |
| 2020/0015900 A1 | 1/2020 | Scheib et al. | |
| 2020/0015901 A1 | 1/2020 | Scheib et al. | |
| 2020/0015902 A1 | 1/2020 | Scheib et al. | |
| 2020/0015903 A1 | 1/2020 | Scheib et al. | |
| 2020/0015906 A1 | 1/2020 | Scheib et al. | |
| 2020/0015907 A1 | 1/2020 | Scheib | |
| 2020/0015914 A1 | 1/2020 | Scheib et al. | |
| 2020/0015923 A1 | 1/2020 | Scheib et al. | |
| 2020/0015924 A1 | 1/2020 | Scheib et al. | |
| 2020/0015925 A1 | 1/2020 | Scheib | |
| 2020/0078109 A1 | 3/2020 | Steger et al. | |
| 2020/0085516 A1 | 3/2020 | DeFonzo et al. | |
| 2020/0100855 A1 | 4/2020 | Leparmentier et al. | |
| 2020/0170720 A1* | 6/2020 | Ummalaneni | A61B 1/00 |
| 2020/0188041 A1 | 6/2020 | Toporek et al. | |
| 2020/0188043 A1 | 6/2020 | Yu et al. | |
| 2020/0222146 A1 | 7/2020 | Komp | |
| 2020/0229866 A1 | 7/2020 | Harlev et al. | |
| 2020/0297403 A1 | 9/2020 | Kochavi | |
| 2020/0315723 A1* | 10/2020 | Hassan | A61B 34/74 |
| 2020/0391053 A1 | 12/2020 | Koyama | |
| 2021/0085410 A1* | 3/2021 | Hassan | A61B 34/32 |
| 2021/0196108 A1 | 7/2021 | Shelton, IV | |
| 2021/0196109 A1 | 7/2021 | Shelton, IV et al. | |
| 2021/0196381 A1 | 7/2021 | Eckert et al. | |
| 2021/0196383 A1 | 7/2021 | Shelton, IV et al. | |
| 2021/0196384 A1 | 7/2021 | Shelton, IV et al. | |
| 2021/0196385 A1 | 7/2021 | Shelton, IV et al. | |
| 2021/0196386 A1 | 7/2021 | Shelton, IV et al. | |
| 2021/0196423 A1 | 7/2021 | Shelton, IV et al. | |
| 2021/0196424 A1 | 7/2021 | Shelton, IV et al. | |
| 2021/0196425 A1 | 7/2021 | Shelton, IV et al. | |
| 2021/0199557 A1 | 7/2021 | Shelton, IV et al. | |
| 2021/0289189 A1 | 9/2021 | Sela | |
| 2021/0307687 A1 | 10/2021 | Culman et al. | |
| 2022/0192758 A1 | 6/2022 | Roh et al. | |
| 2022/0218435 A1 | 7/2022 | Shirazian et al. | |
| 2022/0395342 A1* | 12/2022 | Weiss | A61B 6/4458 |
| 2023/0015694 A1 | 1/2023 | Lim et al. | |
| 2023/0096406 A1 | 3/2023 | Shelton, IV et al. | |
| 2023/0097906 A1* | 3/2023 | Shelton, IV | A61B 18/1492 |
| | | | 606/1 |
| 2023/0098670 A1 | 3/2023 | Shelton, IV et al. | |
| 2023/0105509 A1 | 4/2023 | Shelton, IV et al. | |
| 2023/0116781 A1 | 4/2023 | Shelton, IV et al. | |

FOREIGN PATENT DOCUMENTS

| | | |
|---|---|---|
| EP | 3679851 A1 | 7/2020 |
| EP | 3845192 A1 | 7/2021 |
| EP | 3845193 A1 | 7/2021 |
| WO | WO-02/11639 A1 | 2/2002 |
| WO | WO-2012007052 A1 | 1/2012 |
| WO | WO-2014151621 A1 | 9/2014 |
| WO | WO-2015142814 A1 | 9/2015 |
| WO | WO-2015148378 A1 | 10/2015 |
| WO | WO-2015153636 A1 | 10/2015 |
| WO | WO-2015153642 A1 | 10/2015 |
| WO | WO-2016144937 A1 | 9/2016 |
| WO | WO-2016144998 A1 | 9/2016 |
| WO | WO-2016183054 A1 | 11/2016 |
| WO | WO-2016205266 A1 | 12/2016 |
| WO | WO-2016205452 A1 | 12/2016 |
| WO | WO-2016209769 A1 | 12/2016 |
| WO | WO-2017044406 A1 | 3/2017 |
| WO | WO-2017053358 A1 | 3/2017 |
| WO | WO-2017053363 A1 | 3/2017 |
| WO | WO-2017053507 A1 | 3/2017 |
| WO | WO-2017053698 A1 | 3/2017 |
| WO | WO-2017075121 A1 | 5/2017 |
| WO | WO-2017116793 A1 | 7/2017 |
| WO | WO-2018226050 A1 | 12/2018 |
| WO | WO-2020243432 A1 | 12/2020 |

OTHER PUBLICATIONS

International Search Report and Written Opinion received for Intl. Pat. App. No. PCT/IB2022/059090 mailed on Dec. 6, 2022. (13 pages).

International Search Report and Written Opinion received for Intl. Pat. App. No. PCT/IB2022/059089 mailed on Dec. 8, 2022. (14 pages).

International Search Report and Written Opinion received for Intl. Pat. App. No. PCT/IB2022/059110 mailed on Dec. 14, 2022. (16 pages).

(56)        References Cited

OTHER PUBLICATIONS

"Fiber Bragg Gatings," RP Photonics Encyclopedia, available at <https://www.rp-photonics.com/fiber_bragg_gratings.html>, dated no later than Apr. 5, 2021 (12 pages).

"Ion by Intuitive," available at <https://www.intuitive.com/en-us/products-and-services/ion>, dated no later than Apr. 5, 2021 (5 pages).

Aisu et al., Laparoscopic and endoscopic cooperative surgery for gastric tumors: Perspective for actual practice and oncological benefits,: World J Gastrointest Oncol, Nov. 15, 2018, 10(11): 381-397.

Akirov, "Duodenal Mucosal Resurfacing May Safely Improve Glycemic Control in T2D," Aug. 19, 2019, Haymarket Media, Inc., 14 pages.

Brace et al., "Thermal Tumor Ablation in Clinical Use," IEEE Pulse, 2011, 2(5):28-38.

Carlota V., "4D printing reconfigurable materials for use in aerospace, medical and robotics fields," Apr. 3, 2019, available at <https://www.3dnatices.com/en/4d-printing-materials-030420195/> (7 pages).

Chauhan et al., "Enteroscopy," Gastrointestinal Endoscopy, 2015, vol. 82, No. 6, 975-990.

Conway et al., "Endoscopic hemostatic devices," Gastrointestinal Endoscopy, 2009, vol. 69, No. 6, 987-996.

Dunkin et al., "Thin-layer ablation of human esophageal epithelium using a bipolar radiofrequency balloon device," Surg Endosc (2006) 20: 125-130.

Ethicon, "Laparoscopic Sizing Tool: LINX® Reflux Management System," 2019 (6 pages).

Fried et al., "A novel approach to glycemic control in type 2 diabetes mellius, partial jejunal diversion: pre-clinical to clinical pathway," BMJ Open Diab Res Care 2017; 5:e000431.doi:10.1136*BMJdrc-2017000431.

Garvey, "Ablation of the Duodenal Mucosa as a Strategy for Glycemic Control in Diabetes: Role of Nutrient Signaling or Simple Weight Loss," Diabetes Care 2016; 39:2108-2110.

Gioux et al., "Image-Guided Surgery using Invisible Near-Infrared Light: Fundamental of Clinical Translation," Mol Imaging, Oct. 2010, 9)5): 237-255.

Gupta, "Understanding Image Recognition and Its Uses," elnfochips, available at <http://www.einfochips.com/blog/understanding-image-recognition-and-its-uses/>, Dec. 11, 2019.

Hiki et al., "Laparoscopic and endoscopic cooperative surgery for gastrointestinal stromal tumor dissection," Surg Endosc (2008) 22:1729-1735.

Intuitive Surgical, "Da Vinci Xi Single-Site Technology: Solutions For Single-Incision Surgery," 2016 (10 pages).

Kurata et al., "Time-of-Flight Near-Infrared Spectroscopy for Non-destructive Measurement of Internal Quality in Grapefruit," Journal of the American Society for Horticultural Science, May 2013 vol. 138 No. 3 225-228.

Machytka et al., "Partial jejunal diversion using an incisionless magnetic anastomosis system: 1-year interim results in patients with obesity and diabetes," Gastrointestinal Endoscopy, 2017, vol. 86, No. 5, 904-912.

Matsuda et al., "Laparoscopic endoscopic cooperative surgery (LECS) for the upper gastrointestinal tract," Transl Gastroenterol Hepatol 2017, 2:40 (6 pages).

Miklavčič et al., "Electric Properties of Tissues," Wiley Encyclopedia of Biomedical Engineering, 2006, 1-12.

Sculpteo, "4D Printing: A technology coming from the future," 3D Learning Hub, dated no later than Aug. 26, 2021 (12 pages).

Seeley et al., "The Role of Gut Adaptation in the Potent Effects of Multiple Bariatric Surgeries on Obesity and Diabetes," Cell Metabolism 21, Mar. 3, 2015, 369-378.

Tamegai et al., "Laparoscopic and endoscopic cooperative surgery (LECS) to overcome the limitations of endoscopic resection for colorectal tumors," Endosc Int Open, Dec. 2018, 6(12): E1477-E1485.

Tokar et al., "Electrosurgical generators," Gastrointestinal Endoscopy, 2013, vol. 78, No. 2, 197-208.

Tomie et al., "Blue Laser Imaging-Bright Improves Endoscopic Recognition of Superficial Esophagael Squamous Cell Carcinoma," Gastroenterology Research and Practice, vol. 2016, Article ID 6140854, 7 pages.

Toposens, "Advanced Ultrasonic Sensors: What Makes Them Different?" available at <https://toposens.com/technology/>, 2020.

Toposens, "Beacon Based 3D Tracking System," available at <https://toposens.com/beacon-based-3d-ttracking-system/>, 2020.

U.S. Appl. No. 17/449,765 entitled "Cooperative Access Hybrid Procedures" filed Oct. 1, 2021.

U.S. Appl. No. 17/450,020 entitled "Methods for Controlling Cooperative Surgical Instruments" filed Oct. 5, 2021.

U.S. Appl. No. 17/450,025 entitled "Methods for Controlling Cooperative Surgical Instruments" filed Oct. 5, 2021.

U.S. Appl. No. 17/450,027 entitled "Methods for Controlling Cooperative Surgical Instruments" filed Oct. 5, 2021.

U.S. Appl. No. 17/493,913 entitled "Surgical Methods Using Fiducial Identification and Tracking" filed Oct. 5, 2021.

U.S. Appl. No. 17/494,364 entitled "Surgical Methods for Control of One Visualization With Another" filed Oct. 5, 2021.

U.S. Appl. No. 17/068,857 entitled "Adaptive Responses From Smart Packaging of Drug Delivery Absorbable Adjuncts" filed Oct. 13, 2020.

U.S. Appl. No. 17/068,858 entitled "Drug Administration Devices That Communicate With Surgical Hubs" filed Oct. 13, 2020.

U.S. Appl. No. 17/068,859 entitled "Controlling Operation of Drug Administration Devices Using Surgical Hubs" filed Oct. 13, 2020.

U.S. Appl. No. 17/068,863 entitled "Patient Monitoring Using Drug Administration Devices" filed Oct. 13, 2020.

U.S. Appl. No. 17/068,865 entitled "Monitoring and Communicating Information Using Drug Administration Devices" filed Oct. 13, 2020.

U.S. Appl. No. 17/068,867 entitled "Aggregating And Analyzing Drug Administration Data" filed Oct. 13, 2020.

Van Baar et al., "Endoscopic duodenal mucosal resurfacing for the treatment of type 2 diabetes mellitus: one year results from the first international, open label, prospective, multicentre study," Gut 2020, 69:295-303.

Yang et al., "4d printing reconfigurable, deployable and mechanically tunable materials," Material Science, 2019 (33 pages).

Zuo et al., "Pulmonary Intersegmental Places: Imaging Appearance and Possible Reasons Leading to Their Visualization," Radiology, vol. 267, No. 1, Apr. 2013, 267-275.

* cited by examiner

OBJECT

430

EMITTED WAVE

RECEIVED WAVE

DELAY

DELAY t t $q_1$  $q_2$ $q_1$  $q_2$

RATIO OF "ON" LIGHT TO "OFF" LIGHT

DELAY IS A FUNCTION OF DISTANCE c = SPEED OF LIGHT t = LENGTH OF PULSE $q_1$ = ACCUMULATED CHARGE WHILE LIGHT IS EMITTED $q_2$ = ACCUMULATED CHARGE WHILE LIGHT IS <u>NOT</u> BEING EMITTED $$d = \frac{ct}{2} \cdot \frac{q_2}{q_1 + q_2}$$

410

407

402

408

406

424

407

425

409

404

403

401

405 d

*FIG. 28*
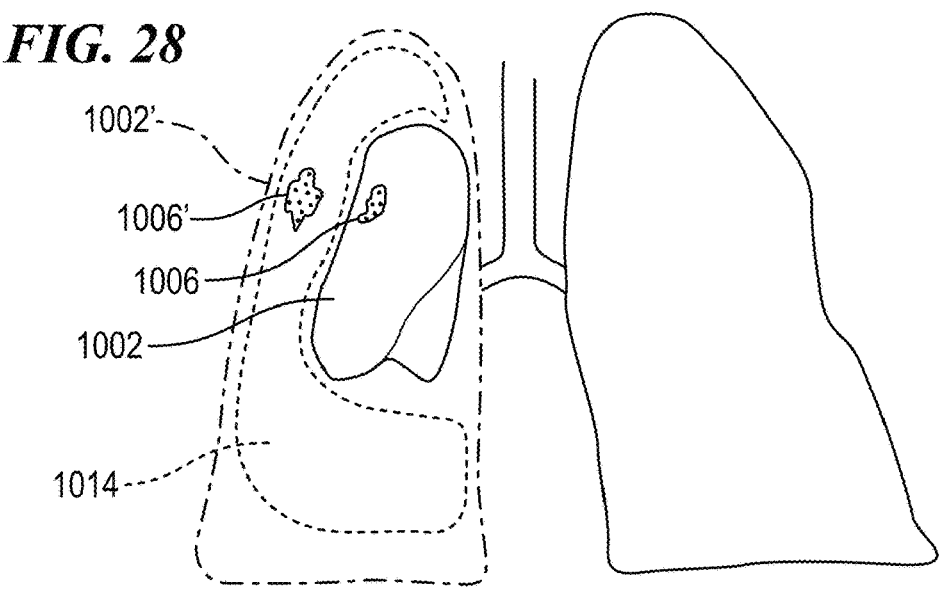
*FIG. 29*
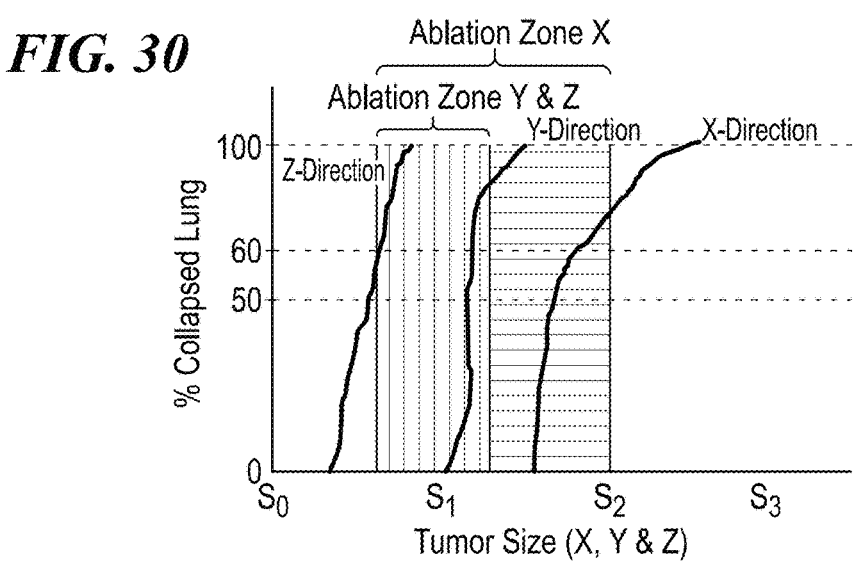
*FIG. 30*

*FIG. 32*
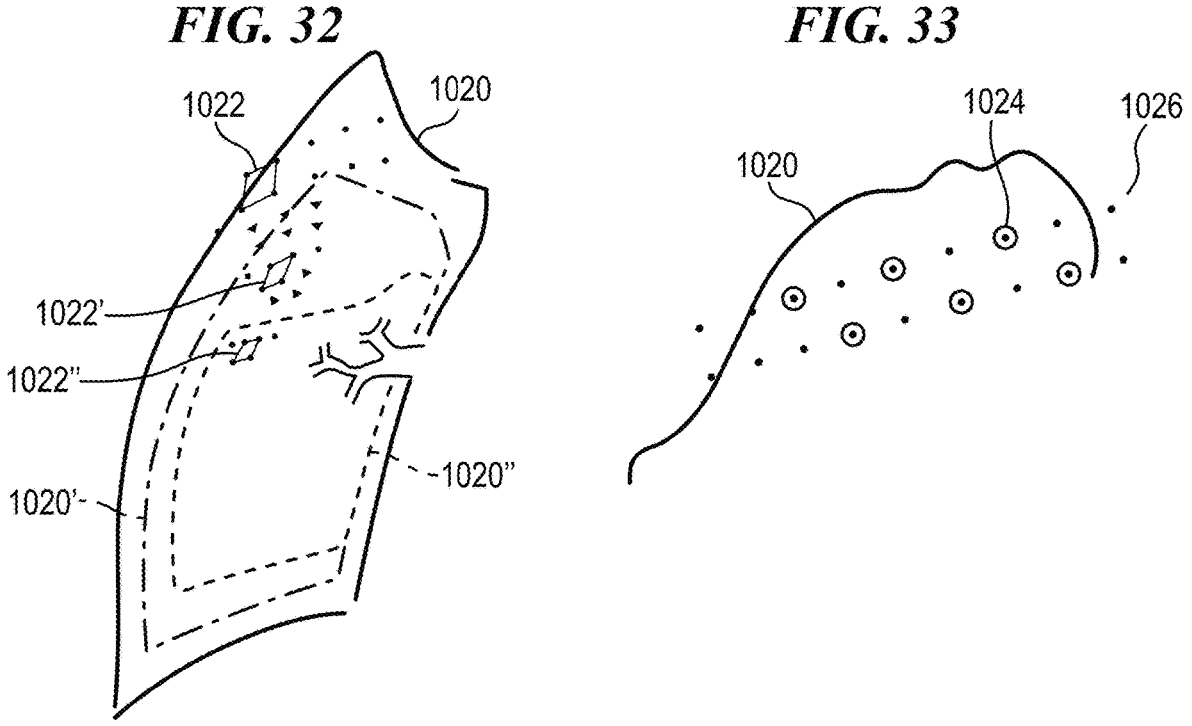
*FIG. 33*
*FIG. 34*
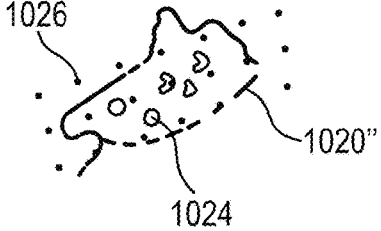

*FIG. 35*
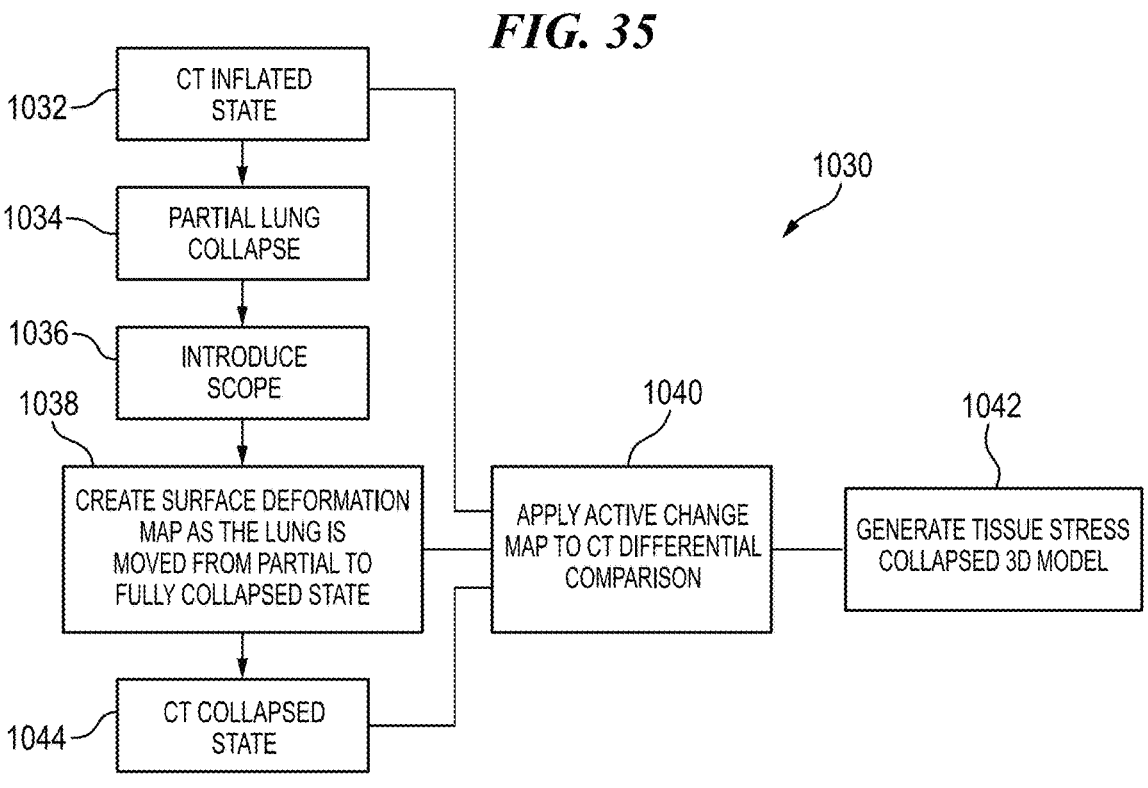
*FIG. 36*          *FIG. 37*
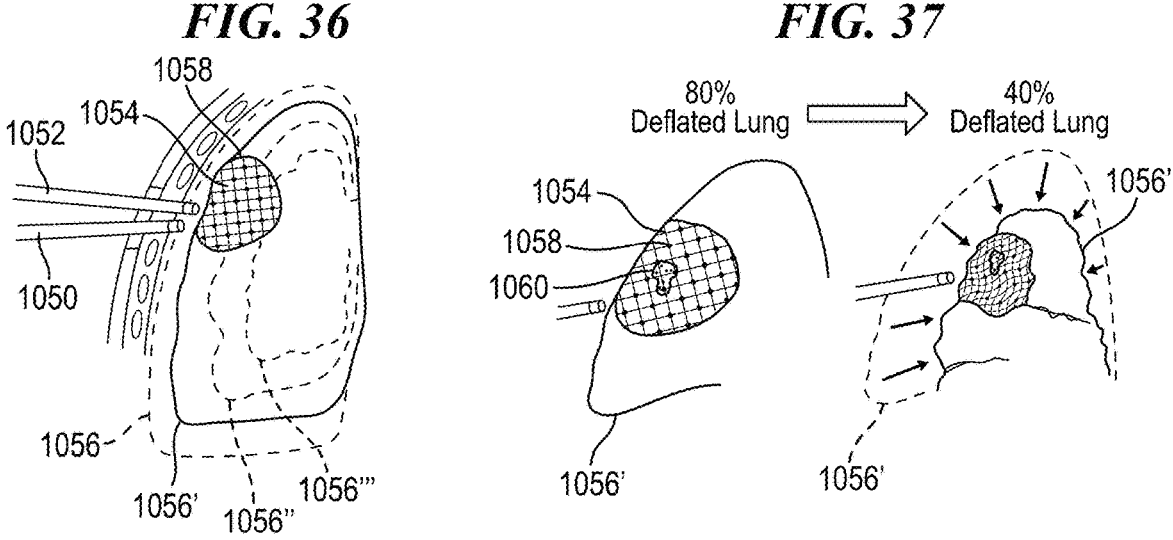

FIG. 43
FRONT VIEW
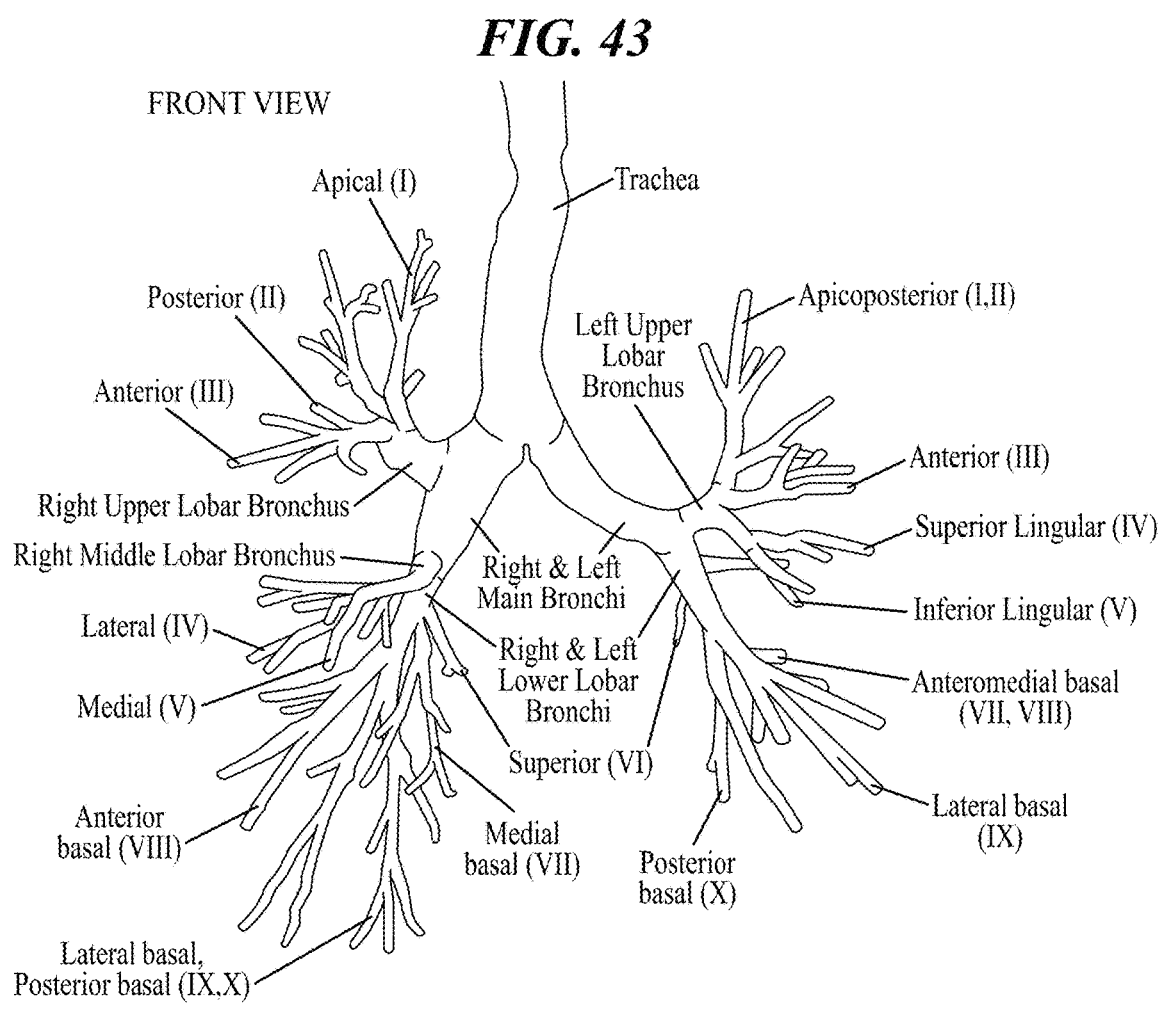
FIG. 44
RIGHT SIDE VIEW
FIG. 45
FRONT VIEW
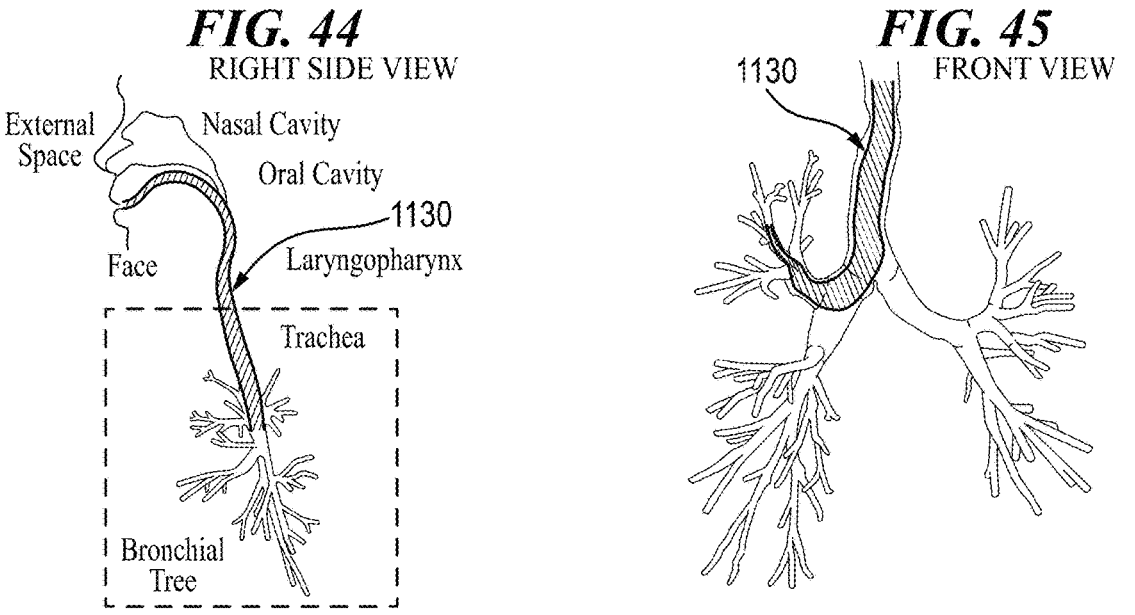

*FIG. 54*
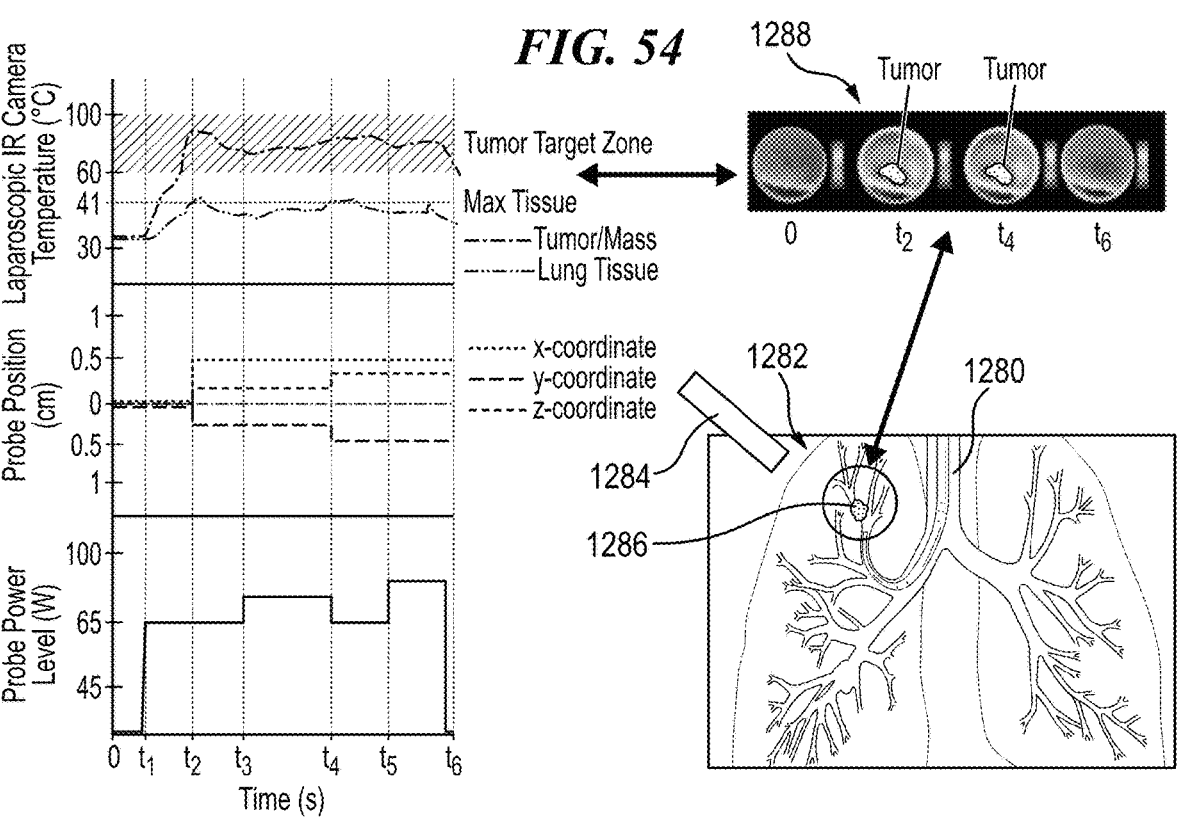
*FIG. 55*
*FIG. 56*
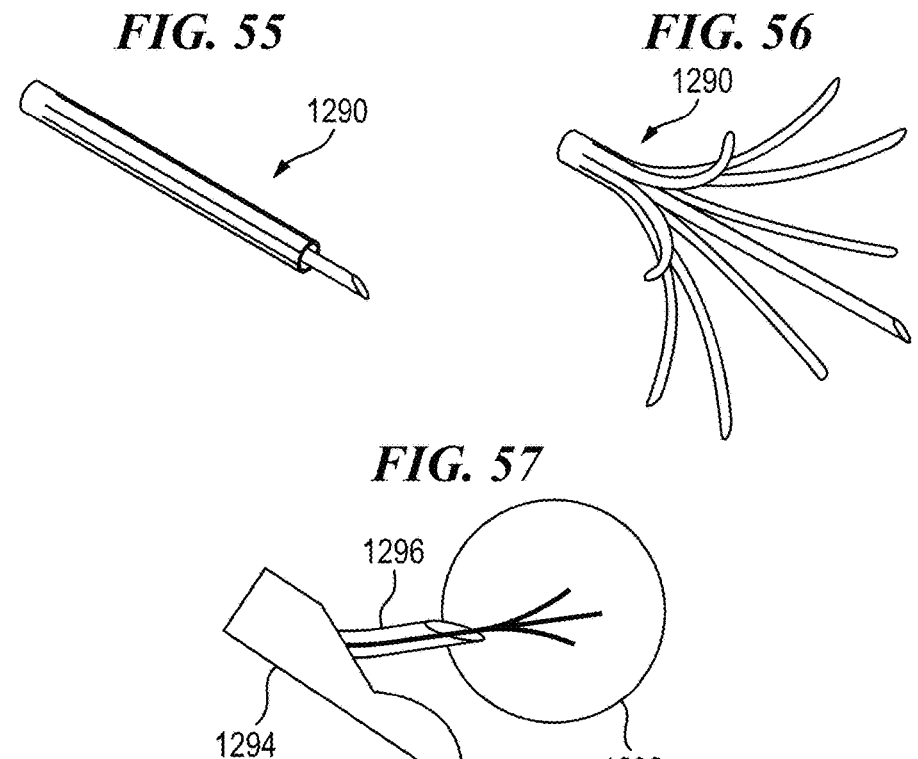
*FIG. 57*

SURGICAL METHODS USING MULTI-SOURCE IMAGING

CROSS REFERENCE TO RELATED APPLICATIONS

The present application claims priority to U.S. Prov. Pat. App. No. 63/249,644 entitled "Surgical Devices, Systems, And Methods Using Multi-Source Imaging" filed Sep. 29, 2021, which is hereby incorporated by reference in its entirety.

FIELD

The present disclosure relates generally to surgical devices, systems, and methods using multi-source imaging.

BACKGROUND

Surgical systems often incorporate an imaging system, which can allow medical practitioners to view a surgical site and/or one or more portions thereof on one or more displays, e.g., a monitor, a computer tablet screen, etc. The display(s) can be local and/or remote to a surgical theater. The imaging system can include a scope with a camera that views the surgical site and transmits the view to the one or more displays viewable by medical practitioner(s).

Imaging systems can be limited by the information that they are able to recognize and/or convey to the medical practitioner(s). For example, certain concealed structures, physical contours, and/or dimensions within a three-dimensional space may be unrecognizable intraoperatively by certain imaging systems. For another example, certain imaging systems may be incapable of communicating and/or conveying certain information to the medical practitioner(s) intraoperatively.

Accordingly, there remains a need for improved surgical imaging.

SUMMARY

In general, devices, systems, and methods for multi-source imaging are provided.

In one aspect, a surgical method is provided that in one embodiment includes visualizing, with a first imaging system, a first side of a tissue wall during performance of a surgical procedure. The first imaging system is a thoracoscopic imaging system or a laparoscopic imaging system. The method also includes visualizing, with an endoscopic imaging system, a second, opposite side of the tissue wall during the performance of the surgical procedure. The first imaging system and the endoscopic imaging system are unable to directly visualize each other, and the first imaging system and the endoscopic imaging system are operatively coupled together. The method also includes guiding a first surgical instrument based on the visualization provided by the first imaging system and the visualization provided by the endoscopic imaging system, and guiding a second surgical instrument configured based on the visualization provided by the endoscopic imaging system and based on the visualization provided by the first imaging system.

The method can vary in any number of ways. For example, at least one of the first and second surgical instruments can include integrated tracking and coordinating means that identifies a location of the at least one first surgical instrument and second surgical instrument, and the method can further include communicating the location to the first imaging system and the endoscopic imaging system so as to provide secondary location verification to the first imaging system and the endoscopic imaging system. For another example, the method can further include determining, with the first imaging system, a location and orientation of the second surgical instrument relative to the first surgical instrument to facilitate the first surgical instrument being guided based on the visualization provided by the endoscopic imaging system, and determining, with the endoscopic imaging system, a location and orientation of the first surgical instrument relative to the second surgical instrument to facilitate the second surgical instrument being guided based on the visualization provided by the first imaging system. For yet another example, the method can further include visualizing, with each of the first imaging system and the endoscopic imaging system, a common anatomic landmark and thereby facilitate guiding of the first and second surgical instruments relative to one another. For still another example, one of the first imaging system and the endoscopic imaging system can include a structured light emitter configured to emit a structured light pattern on a surface of an organ, a spectral light emitter configured to emit spectral light in a plurality of wavelengths capable of penetrating the organ and reaching an internal aspect located below the surface of the organ, and an image sensor configured to detect reflected structured light pattern, reflected spectral light, and reflected visible light, and the surgical method can further include constructing, with a controller, a three-dimensional (3D) digital representation of the organ from the reflected structured light pattern detected by the image sensor, detecting, with the controller, the internal aspect from the reflected spectral light detected by the image sensor, integrating, with the controller, the internal aspect with the 3D digital representation of the organ, and causing, with the controller, a display device to show the internal aspect and a 3D rendering of the organ based on the 3D digital representation of the organ. For another example, the method can further include visualizing, with a computerized tomography (CT) imaging system, the first and second instruments and thereby facilitate guiding of the first and second surgical instruments relative to one another. For still another example, the method can further include gathering, with a non-magnetic sensing system that uses at least one of ultrasonic energy and radiofrequency (RF) energy, data indicative of a location of the first and second surgical instruments and thereby facilitate guiding of the first and second surgical instruments relative to one another. For another example, the first and second surgical instruments can each be releasably coupled to a robotic surgical system that controls the guiding of each of the first and second surgical instruments.

In another embodiment, a surgical method includes gathering, with an imaging device, images of an organ during performance of a surgical procedure. The images include a plurality of images each gathered at a different time during the performance of the surgical procedure as the organ undergoes distortions. The method also includes tracking, with a controller, the organ from a first state to a second, different state that is subsequent to the first state by analyzing the plurality of images. The tracking allows the controller to predict an internal aspect of the organ in the second state. The method also includes causing, with the controller, a display device to show an indication of the internal aspect of the organ in the second state.

The method can have any number of variations. For example, the tracking can forecast a perimeter shape of the internal aspect in the second state, a location of the internal aspect in the organ in the second state, and an orientation of the internal aspect in the organ in the second state. For another example, the plurality of images can be analyzed with respect to at least one of tissue strain and a geometry of the organ.

For yet another example, the imaging device can include a flexible scoping device, the organ can be a lung, the internal aspect can be a tumor. The lung in the first state can be expanded, and the lung in the second state can be collapsed. The method can further include controlling, with the controller, the collapse of the lung to create a predefined shape of the tumor.

For another example, the imaging device can include a structured light emitter configured to emit a structured light pattern on a surface of the organ, a spectral light emitter configured to emit spectral light in a plurality of wavelengths capable of penetrating the organ and reaching the internal aspect located below the surface of the organ, and an image sensor configured to detect reflected structured light pattern, reflected spectral light, and reflected visible light, and the method can further include constructing, with a controller, a three-dimensional (3D) digital representation of the organ from the reflected structured light pattern detected by the image sensor, detecting, with the controller, the internal aspect from the reflected spectral light detected by the image sensor, integrating, with the controller, the internal aspect with the 3D digital representation of the organ, and causing, with the controller, a display device to show the internal aspect and a 3D rendering of the organ based on the 3D digital representation of the organ.

For still another example, the organ can be a lung, the imaging device can include a bronchoscope, the method can further include advancing the bronchoscope distally in an airway of the lung during the performance of the surgical procedure, and the method can further include automatically causing, with the controller, the bronchoscope to be retracted proximally in the airway of the lung during the performance of the surgical procedure. The method can further include automatically causing, with the controller, the bronchoscope to be retracted proximally based on an analysis of the images indicating the bronchoscope being within a threshold distance of a tissue wall. The method can further include automatically causing, with the controller, the bronchoscope to be retracted proximally also based on at least one of a rate of change of a volume of the lung and a rate of change of an external surface of the lung. The method can further include automatically causing, with the controller, the bronchoscope to be retracted proximally also based on the rate of change of the volume of the lung as indicated by at least one of CT imaging and ventilator exchange. The imaging device can include a structured light emitter that emits a structured light pattern on the external surface of the organ, the imaging device can include an image sensor that detects reflected structured light pattern, and the method can further include automatically causing, with the controller, the bronchoscope to be retracted proximally also based on the rate of change of the external surface of the lung as indicated by the reflected structure light pattern.

For yet another example, a surgical hub can include the controller. For still another example, a robotic surgical system can includes the controller, and the imaging device can be releasably coupled to and controlled by the robotic surgical system.

In another embodiment, a surgical method includes gathering, with a first imaging device, first images visualizing a surgical target, gathering, with a second imaging device, second images that enhance the visualization of the surgical target, and causing, with a controller, a display device to show a single view of the surgical target that is a cooperation of the first and second images. The first imaging device has a different point of view of the surgical site than the second imaging device.

The method can vary in any number of ways. For example, the different point of view of the first imaging device can be a physically different point of view of the surgical site than the second imaging device, and the surgical target can not be accurately visible by at least one of the first and second imaging devices. The method can further include causing, with the controller, the point of view of the first imaging device to change based on the second images gathered by the second imaging device. The second imaging device can have a point of view within a body lumen, the first imaging device can have a point of view outside the body lumen, the second imaging device can have a point of view from a first side of a tissue wall, the first imaging device can have a point of view from a second side of the tissue wall that is opposite to the first side of the tissue wall, or the second imaging device can have a point of view from a first side of an organ and the first imaging device can have a point of view from a second, different side of the organ.

For another example, the different point of view of the first imaging device can be the first imaging device having a different energy modality than the second imaging device. The different energy modality can include the second imaging device having ultrasound or CT modality and the first imaging device having another type of energy modality.

For yet another example, the different point of view of the first imaging device can be the first imaging device having a physically different point of view of the surgical site than the second imaging device and having a different energy modality than the second imaging device. For another example, the first imaging device can be operated by a first user during a surgical procedure in which the first and second images are being gathered, the second imaging device can be operated by a second user during the surgical procedure; and a surgical hub can include the controller. For still another example, the first and second imaging devices can each be releasably coupled to and controlled by a robotic surgical system, and the robotic surgical system can include the controller. For another example, a robotic surgical system can include the controller and the display device, and the first and second imaging devices can each be releasably coupled to and controlled by the robotic surgical system. For yet another example, the surgical target can include a tumor at a lung, and the first imaging device can include a flexible scoping device.

In another embodiment, a surgical method includes gathering, with a first imaging device, first images of a surgical site during performance of a surgical procedure, gathering, with a second imaging device, second images of the surgical site during the performance of the surgical procedure, analyzing, with a controller, the first images and the second images to identify and define boundaries of connective soft tissue planes, relating, with the controller, the identified and defined boundaries of the connective soft tissue planes to an anatomic structure and a role of the tissue, and causing, with the controller, a display device to show information related to the tissue and to show at least one of the first images and the second images overlaid with the identified and defined boundaries of the connective soft tissue planes and thereby define a location and orientation of the connective soft tissue planes.

The method can have any number of variations. For example, the anatomic structure and the role of the tissue can include at least one of tissue planes, tissue composition, tumor location, tumor margin identification, adhesions, vascularization, and tissue fragility. For another example, the information related to the tissue can include at least one of a type of the tissue, collagen composition of the tissue, organized versus remodeled disorganized fiber orientation of the tissue, viability of the tissue, and health of the tissue. For yet another example, the first imaging device can include a structured light emitter configured to emit a structured light pattern on a surface of the anatomic structure, a spectral light emitter configured to emit spectral light in a plurality of wavelengths capable of penetrating the anatomic structure and reaching an embedded structure located below the surface of the anatomic structure, and an image sensor configured to detect reflected structured light pattern, reflected spectral light, and reflected visible light, the method can further include constructing, with the controller, a three-dimensional (3D) digital representation of the anatomic structure from the reflected structured light pattern detected by the image sensor, and the controller can use the 3D digital representation in identifying and defining the boundaries of the connective soft tissue planes. For still another example, the first imaging device can include a flexible scoping device, and the second imaging device can includes a rigid scoping device. For another example, the first imaging device can include a bronchoscope, the anatomic structure can include a lung, the method can further include advancing the bronchoscope into the lung, the tissue can include bronchial tissue, the embedded structure can include a tumor, and the location and orientation of the connective soft tissue planes can enable identification of tumor location and orientation in the lung.

For yet another example, the first imaging device can gather the first images using a wavelength outside a spectrum of visible light so as to allow visualization of the embedded structure from outside the anatomic structure, the wavelength outside the spectrum of visible light can include an ultrasound wavelength or an infrared wavelength, and the second imaging device can gather the second images using a wavelength within the spectrum of visible light so as to allow visualization of the surface of the anatomic structure. The method can further include delivering a contrast agent to the anatomic structure, the first imaging device can visualize the contrast agent within the anatomic structure, and the second imaging device cannot visualize the contrast agent within the anatomic structure.

For still another example, the first and second imaging devices can be releasably coupled to and controlled by a robotic surgical system, and a surgical hub can include the controller. For another example, a robotic surgical system can include the controller and the display device, and the first and second imaging devices can each be releasably coupled to and controlled by the robotic surgical system.

In another embodiment, a surgical method includes visualizing a surgical site with a first visualization system, visualizing the surgical site with a second visualization system configured to visualize the surgical site, and monitoring, with a controller and during the second visualization system's visualization of the surgical site, energy delivery to tissue at the surgical site. The energy is being delivered to the tissue by an electrode of a surgical instrument positioned in a lumen of the first visualization system. The method also includes controlling, with the controller, energizing of the electrode such that a parameter associated with the tissue does not exceed a predefined maximum threshold.

The method can vary in any number of ways. For example, the predefined maximum threshold can include a temperature of the tissue, and the method can further include measuring the temperature of the tissue with a sensor operatively coupled to the controller. For another example, the predefined maximum threshold can include a temperature of the tissue, the electrode can include an electrode array, and the method can further include measuring the temperature of the tissue with the electrode array. For still another example, the predefined maximum threshold can include a surface water content of the tissue, and the method can further include measuring the surface water content of the tissue with a sensor operatively coupled to the controller. For another example, the predefined maximum threshold can include a refractivity of the tissue, and the method can further include measuring the refractivity of the tissue with at least one of the first and second visualization systems. For yet another example, the first visualization system can be visualizing within a hollow organ at the surgical site, the tissue can be tissue within the hollow organ, and the second visualization system can be visualizing outside the hollow organ. For another example, the energy can include one of radiofrequency (RF) energy and microwave energy. For yet another example, the tissue can include a tumor, and the energy can include cold so as to treat the tumor with cyroablation. For still another example, a surgical hub can include the controller. For yet another example, a robotic surgical system can include the controller, and the surgical instrument can be configured to be releasably coupled to and controlled by the robotic surgical system.

In one aspect, a surgical system is provided that in one embodiment includes a first imaging device configured to gather first images for visualization of a surgical target, a second imaging device configured to gather second images that enhance the visualization of the surgical target, and a controller configured to cause a display device to show a single view of the surgical target that is a cooperation of the first and second images. The first imaging device has a different point of view of the surgical site than the second imaging device.

The surgical system can vary in any number of ways. For example, the different point of view of the first imaging device can be a physically different point of view of the surgical site than the second imaging device, and the surgical target can not be accurately visible by at least one of the first and second imaging devices. The controller can be configured to cause the point of view of the first imaging device to change based on the second images gathered by the second imaging device. The second imaging device can be configured to have a point of view within a body lumen, the first imaging device can be configured to have a point of view outside the body lumen, the second imaging device can be configured to have a point of view from a first side of a tissue wall, the first imaging device can be configured to have a point of view from a second side of the tissue wall that is opposite to the first side of the tissue wall, or the second imaging device can be configured to have a point of view from a first side of an organ and the first imaging device is configured to have a point of view from a second, different side of the organ.

For another example, the different point of view of the first imaging device can be the first imaging device having a different energy modality than the second imaging device. The different energy modality can include the second imaging device having ultrasound or CT modality and the first imaging device having another type of energy modality.

For yet another example, the different point of view of the first imaging device can be the first imaging device having a physically different point of view of the surgical site than the second imaging device and having a different energy modality than the second imaging device. For still another example, the first imaging device can be configured to be operated by a first user during a surgical procedure in which the first and second images are being gathered, the second imaging device can be configured to be operated by a second user during the surgical procedure, and a surgical hub can include the controller. For another example, the system can further include the display device, a robotic surgical system can include the controller and the display device, and the first and second imaging devices can each be configured to be releasably coupled to and controlled by the robotic surgical system.

In another embodiment, a surgical system includes a first imaging device configured to gather first images of a surgical site during performance of a surgical procedure, a second imaging device configured to gather second images of the surgical site during the performance of the surgical procedure, and a controller configured to analyze the first images and the second images to identify and define boundaries of connective soft tissue planes, relate the identified and defined boundaries of the connective soft tissue planes to an anatomic structure and a role of the tissue, and cause a display device to show information related to the tissue and to show at least one of the first images and the second images overlaid with the identified and defined boundaries of the connective soft tissue planes and thereby define a location and orientation of the connective soft tissue planes.

The system can vary in any number of ways. For example, the anatomic structure and the role of the tissue can include at least one of tissue planes, tissue composition, tumor location, tumor margin identification, adhesions, vascularization, and tissue fragility. For another example, the information related to the tissue can include at least one of a type of the tissue, collagen composition of the tissue, organized versus remodeled disorganized fiber orientation of the tissue, viability of the tissue, and health of the tissue. For yet another example, the first imaging device can include a structured light emitter configured to emit a structured light pattern on a surface of the anatomic structure, a spectral light emitter configured to emit spectral light in a plurality of wavelengths capable of penetrating the anatomic structure and reaching an embedded structure located below the surface of the anatomic structure, and an image sensor configured to detect reflected structured light pattern, reflected spectral light, and reflected visible light, the controller can be configured to construct a three-dimensional (3D) digital representation of the anatomic structure from the reflected structured light pattern detected by the image sensor, and the controller can be configured to use the 3D digital representation in identifying and defining the boundaries of the connective soft tissue planes. For still another example, the first imaging device can include a flexible scoping device, and the second imaging device can includes a rigid scoping device. For yet another example, the anatomic structure can include a lung, the first imaging device can include a bronchoscope configured to be advanced into the lung, the tissue can include bronchial tissue, the embedded structure can include a tumor, and the location and orientation of the connective soft tissue planes can enable identification of tumor location and orientation in the lung.

For another example, the first imaging device can be configured to gather the first images using a wavelength outside a spectrum of visible light so as to allow visualization of the embedded structure from outside the anatomic structure, the wavelength outside the spectrum of visible light can include an ultrasound wavelength or an infrared wavelength, and the second imaging device can be configured to gather the second images using a wavelength within the spectrum of visible light so as to allow visualization of the surface of the anatomic structure. The system can further include a contrast agent configured to be delivered to the anatomic structure, the first imaging device can be configured to visualize the contrast agent within the anatomic structure, and the second imaging device cannot visualize the contrast agent within the anatomic structure.

For yet another example, the first and second imaging devices can each be configured to be releasably coupled to and controlled by a robotic surgical system, and a surgical hub can include the controller. For another example, the system can further include the display device, a robotic surgical system can include the controller and the display device, and the first and second imaging devices can each be configured to be releasably coupled to and controlled by the robotic surgical system.

In another embodiment, a surgical system includes a first imaging system configured to provide visualization of a surgical site including a tissue wall. The first imaging system is a thoracoscopic imaging system or a laparoscopic imaging system. The system also includes a first surgical instrument configured to be guided based on the visualization provided by the first imaging system, an endoscopic imaging system configured to be advanced to the surgical site transorally and configured to provide visualization of the surgical site including the tissue wall, and a second surgical instrument configured to be guided based on the visualization provided by the endoscopic imaging system. With the first imaging system and the endoscopic imaging system being unable to directly visualize each other, the first imaging system is configured to visualize a first side of the tissue wall during performance of a surgical procedure and the endoscopic imaging system is configured to visualize a second, opposite side of the tissue wall during the performance of the surgical procedure. The first imaging system and the endoscopic imaging system are configured to be operatively coupled together such that the first surgical instrument is also configured to be guided based on the visualization provided by the endoscopic imaging system and the second surgical instrument is also configured to be guided based on the visualization provided by the first imaging system.

The system can vary in any number of ways. For example, at least one of the first and second surgical instruments can include integrated tracking and coordinating means configured to identify a location of the at least one first surgical instrument and second surgical instrument and can be configured to communicate the location to the first imaging system and the endoscopic imaging system so as to provide secondary location verification to the first imaging system and the endoscopic imaging system. For another example, the first imaging system can be configured to determine a location and orientation of the second surgical instrument relative to the first surgical instrument to facilitate the first surgical instrument being guided based on the visualization provided by the endoscopic imaging system, and the endoscopic imaging system can be configured to determine a location and orientation of the first surgical instrument relative to the second surgical instrument to facilitate the second surgical instrument being guided based on the visualization provided by the first imaging system. For yet another example, the first imaging system and the endoscopic imaging system can be configured to each visualize a common anatomic landmark and thereby facilitate guiding of the first and second surgical instruments relative to one another. For still another example, one of the first imaging system and the endoscopic imaging system includes a structured light emitter configured to emit a structured light pattern on a surface of an organ, a spectral light emitter configured to emit spectral light in a plurality of wavelengths capable of penetrating the organ and reaching an internal aspect located below the surface of the organ, and an image sensor configured to detect reflected structured light pattern, reflected spectral light, and reflected visible light, and the surgical system further includes a controller configured to construct a three-dimensional (3D) digital representation of the organ from the reflected structured light pattern detected by the image sensor, detect the internal aspect from the reflected spectral light detected by the image sensor, integrate the internal aspect with the 3D digital representation of the organ, and cause a display device to show the internal aspect and a 3D rendering of the organ based on the 3D digital representation of the organ. For another example, the system can further include a computerized tomography (CT) imaging system configured to provide visualization of the first and second instruments and thereby facilitate guiding of the first and second surgical instruments relative to one another. For yet another example, the system can further include a non-magnetic sensing system that uses at least one of ultrasonic energy and radiofrequency (RF) energy and is configured to gather data indicative of a location of the first and second surgical instruments and thereby facilitate guiding of the first and second surgical instruments relative to one another. For another example, the first and second surgical instruments can each be configured to be releasably coupled to a robotic surgical system configured to control the guiding of each of the first and second surgical instruments.

In another embodiment, a surgical system includes an imaging device configured to gather images of an organ during performance of a surgical procedure. The images include a plurality of images each gathered at a different time during the performance of the surgical procedure as the organ undergoes distortions. The system also includes a controller configured to track the organ from a first state to a second, different state that is subsequent to the first state by analyzing the plurality of images. The tracking allows the controller to predict an internal aspect of the organ in the second state. The controller is also configured to cause a display device to show an indication of the internal aspect of the organ in the second state.

The system can have any number of variations. For example, the tracking can forecast a perimeter shape of the internal aspect in the second state, a location of the internal aspect in the organ in the second state, and an orientation of the internal aspect in the organ in the second state. For another example, the plurality of images can be analyzed with respect to at least one of tissue strain and a geometry of the organ.

For yet another example, the imaging device can include a flexible scoping device, the organ can be a lung, and the internal aspect can be a tumor. The lung in the first state can be expanded, and the lung in the second state can be collapsed. The controller can be configured to control the collapse of the lung to create a predefined shape of the tumor.

For still another example, the imaging device can include a structured light emitter configured to emit a structured light pattern on a surface of the organ, a spectral light emitter configured to emit spectral light in a plurality of wavelengths capable of penetrating the organ and reaching the internal aspect located below the surface of the organ, and an image sensor configured to detect reflected structured light pattern, reflected spectral light, and reflected visible light, and the controller can be configured to construct a three-dimensional (3D) digital representation of the organ from the reflected structured light pattern detected by the image sensor, detect the internal aspect from the reflected spectral light detected by the image sensor, integrate the internal aspect with the 3D digital representation of the organ, and cause a display device to show the internal aspect and a 3D rendering of the organ based on the 3D digital representation of the organ.

For yet another example, the organ can be a lung, the imaging device can include a bronchoscope configured to be advanced distally in an airway of the lung during the performance of the surgical procedure, and the controller can be configured to automatically cause the bronchoscope to be retracted proximally in the airway of the lung during the performance of the surgical procedure. The controller can be configured to automatically cause the bronchoscope to be retracted proximally based on an analysis of the images indicating the bronchoscope being within a threshold distance of a tissue wall. The controller can be configured to automatically cause the bronchoscope to be retracted proximally also based on at least one of a rate of change of a volume of the lung and a rate of change of an external surface of the lung. The controller can be configured to automatically cause the bronchoscope to be retracted proximally also based on the rate of change of the volume of the lung as indicated by at least one of CT imaging and ventilator exchange. The imaging device can include a structured light emitter configured to emit a structured light pattern on the external surface of the organ, the imaging device can include an image sensor configured to detect reflected structured light pattern, and the controller can be configured to automatically cause the bronchoscope to be retracted proximally also based on the rate of change of the external surface of the lung as indicated by the reflected structure light pattern.

For still another example, a surgical hub can include the controller. For another example, a robotic surgical system can include the controller, and the imaging device can be configured to be releasably coupled to and controlled by the robotic surgical system.

In another embodiment, a surgical system includes a first visualization system configured to visualize a surgical site, and a surgical instrument configured to be advanced to the surgical site through a lumen of the first visualization system. The surgical includes an electrode configured to deliver energy to tissue at a surgical site. The system also includes a second visualization system configured to visualize the surgical site, and a controller configured to be operatively coupled to the electrosurgical instrument and to the second visualization system, monitor the electrode's energy delivery to the tissue during the delivery and during the second visualization system's visualization of the surgical site, and control energizing of the electrode such that a parameter associated with the tissue does not exceed a predefined maximum threshold.

The system can vary in any number of ways. For example, the predefined maximum threshold can include a temperature of the tissue, and the system can further include a sensor operatively coupled to the controller and configured to measure the temperature of the tissue. For another example, the predefined maximum threshold includes a temperature of the tissue, and the electrode can include an electrode array configured to measure the temperature of the tissue. For yet another example, the predefined maximum threshold can include a surface water content of the tissue, and the system can further include a sensor operatively coupled to the controller and configured to measure the surface water content of the tissue. For still another example, the predefined maximum threshold can include a refractivity of the tissue, and at least one of the first and second visualization systems can be configured to measure the refractivity of the tissue. For another example, the first visualization system can be configured to visualize within a hollow organ at the surgical site, the tissue can be tissue within the hollow organ, and the second visualization system can be configured to visualize outside the hollow organ. For yet another example, the energy can include one of radiofrequency (RF) energy and microwave energy. For still another example, the tissue can include a tumor, and the energy can include cold so as to treat the tumor with cyroablation. For another example, a surgical hub can include the controller. For still another example, a robotic surgical system can include the controller, and the surgical instrument can be configured to be releasably coupled to and controlled by the robotic surgical system.

BRIEF DESCRIPTION OF DRAWINGS

The present invention is described by way of reference to the accompanying figures which are as follows:

FIG. 28 is a schematic view illustrating the lung of FIG. 24 and the lung in an inflated state;

FIG. 29 is a schematic view of a tumor in the lung of FIG. 28 corresponding to the inflated and collapsed states of the lung;

FIG. 30 is a graph showing lung collapse percentage versus tumor size in X, Y, and X dimensions;

FIG. 32 is a schematic view of a lung in an inflated state, a partially collapses state, and a fully collapses state;

FIG. 33 is a schematic view of the lung of FIG. 32 in the inflated state with physical organ tag markers and a projected light structure thereon;

FIG. 34 is a schematic view of the lung of FIG. 32 in the inflated state with physical organ tag markers and a projected light structure thereon;

FIG. 35 is a flowchart of one embodiment of a method of predicting tumor size using measured tissue strain;

FIG. 36 is a schematic view of a lung inflated and in various states of collapse;

FIG. 37 is a schematic view of the lung in two of the collapsed states of FIG. 36;

FIG. 43 is a schematic front view of lung airways;

FIG. 44 is a schematic right side view of one embodiment of a path of advancement of a scope in a lung;

FIG. 45 is a schematic front view of the path of advancement of the scope of FIG. 44;

FIG. 54 is illustrates one embodiment of controlling energy of a microwave ablation device;

FIG. 55 is a perspective view of a distal portion of one embodiment of an ablation device in a compressed configuration;

FIG. 56 is a perspective view of the distal portion the ablation device of FIG. 55 in an expanded configuration;

FIG. 57 is a perspective view of the ablation device of FIG. 56 positioned relative to a tumor;

DETAILED DESCRIPTION

Figure 1:
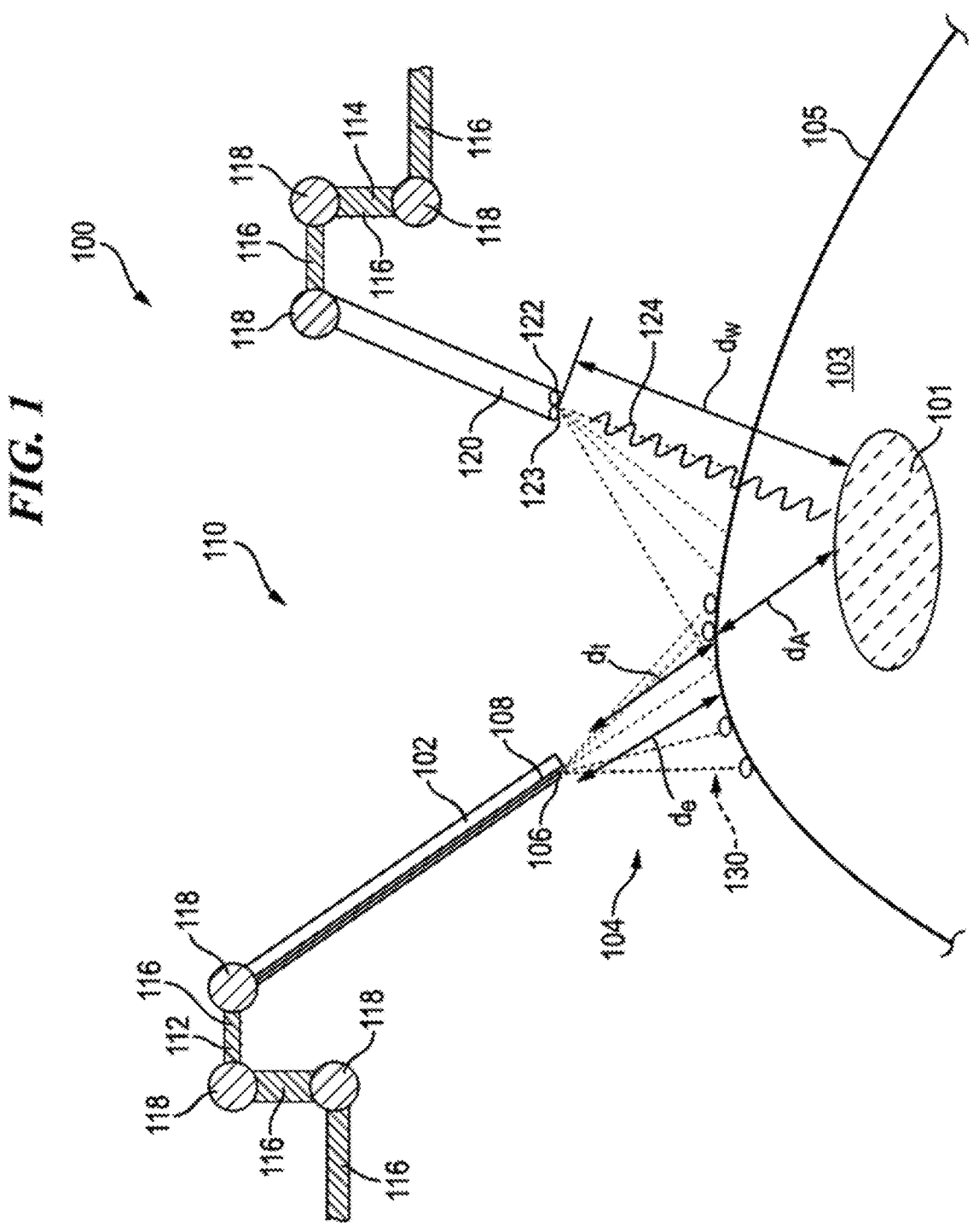
FIG. 1 is a schematic view of one embodiment of a surgical visualization system.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension or other measurement may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Surgical Visualization

In general, a surgical visualization system is configured to leverage "digital surgery" to obtain additional information about a patient's anatomy and/or a surgical procedure. The surgical visualization system is further configured to convey data to one or more medical practitioners in a helpful manner. Various aspects of the present disclosure provide improved visualization of the patient's anatomy and/or the surgical procedure, and/or use visualization to provide improved control of a surgical tool (also referred to herein as a "surgical device" or a "surgical instrument").

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization systems described herein can be used in combination with a robotic surgical system, surgical visualization systems are not limited to use with a robotic surgical system. In certain instances, surgical visualization using a surgical visualization system can occur without robotics and/or with limited and/or optional robotic assistance. Similarly, digital surgery can occur without robotics and/or with limited and/or optional robotic assistance.

In certain instances, a surgical system that incorporates a surgical visualization system may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, a surgical fastener, a clip, a tack, a bougie, a band, a plate, and other foreign structures. Critical structures can be determined on a patient-by-patient and/or a procedure-by-procedure basis. Smart dissection technology may provide, for example, improved intraoperative guidance for dissection and/or may enable smarter decisions with critical anatomy detection and avoidance technology.

A surgical system incorporating a surgical visualization system may enable smart anastomosis technologies that provide more consistent anastomoses at optimal location(s) with improved workflow. Cancer localization technologies may be improved with a surgical visualization platform. For example, cancer localization technologies can identify and track a cancer location, orientation, and its margins. In certain instances, the cancer localization technologies may compensate for movement of a surgical instrument, a patient, and/or the patient's anatomy during a surgical procedure in order to provide guidance back to the point of interest for medical practitioner(s).

A surgical visualization system may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies may be utilized without ionizing radiation and/or contrast agents. With respect to lymph node diagnostics and mapping, a surgical visualization platform may, for example, preoperatively locate, map, and ideally diagnose the lymph system and/or lymph nodes involved in cancerous diagnosis and staging.

During a surgical procedure, information available to a medical practitioner via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move pre-operatively (e.g., before a surgical procedure but after a preoperative scan) and/or intraoperatively. In such instances, the medical practitioner can be unable to accurately determine the location of a critical structure intraoperatively.

When the position of a critical structure is uncertain and/or when the proximity between the critical structure and a surgical tool is unknown, a medical practitioner's decision-making process can be inhibited. For example, a medical practitioner may avoid certain areas in order to avoid inadvertent dissection of a critical structure; however, the avoided area may be unnecessarily large and/or at least partially misplaced. Due to uncertainty and/or overly/excessive exercises in caution, the medical practitioner may not access certain desired regions. For example, excess caution may cause a medical practitioner to leave a portion of a tumor and/or other undesirable tissue in an effort to avoid a critical structure even if the critical structure is not in the particular area and/or would not be negatively impacted by the medical practitioner working in that particular area. In certain instances, surgical results can be improved with increased knowledge and/or certainty, which can allow a surgeon to be more accurate and, in certain instances, less conservative/more aggressive with respect to particular anatomical areas.

A surgical visualization system can allow for intraoperative identification and avoidance of critical structures. The surgical visualization system may thus enable enhanced intraoperative decision making and improved surgical outcomes. The surgical visualization system can provide advanced visualization capabilities beyond what a medical practitioner sees with the "naked eye" and/or beyond what an imaging system can recognize and/or convey to the medical practitioner. The surgical visualization system can augment and enhance what a medical practitioner is able to know prior to tissue treatment (e.g., dissection, etc.) and, thus, may improve outcomes in various instances. As a result, the medical practitioner can confidently maintain momentum throughout the surgical procedure knowing that the surgical visualization system is tracking a critical structure, which may be approached during dissection, for example. The surgical visualization system can provide an indication to the medical practitioner in sufficient time for the medical practitioner to pause and/or slow down the surgical procedure and evaluate the proximity to the critical structure to prevent inadvertent damage thereto. The surgical visualization system can provide an ideal, optimized, and/or customizable amount of information to the medical practitioner to allow the medical practitioner to move confidently and/or quickly through tissue while avoiding inadvertent damage to healthy tissue and/or critical structure(s) and, thus, to minimize the risk of harm resulting from the surgical procedure.

Surgical visualization systems are described in detail below. In general, a surgical visualization system can include a first light emitter configured to emit a plurality of spectral waves, a second light emitter configured to emit a light pattern, and a receiver, or sensor, configured to detect visible light, molecular responses to the spectral waves (spectral imaging), and/or the light pattern. The surgical visualization system can also include an imaging system and a control circuit in signal communication with the receiver and the imaging system. Based on output from the receiver, the control circuit can determine a geometric surface map, e.g., three-dimensional surface topography, of the visible surfaces at the surgical site and a distance with respect to the surgical site, such as a distance to an at least partially concealed structure. The imaging system can convey the geometric surface map and the distance to a medical practitioner. In such instances, an augmented view of the surgical site provided to the medical practitioner can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of a surgical tool to the visible and obstructing tissue and/or to the at least partially concealed structure and/or a depth of the concealed structure below the visible surface of the obstructing tissue. For example, the visualization system can determine a distance with respect to the augmented line on the surface of the visible tissue and convey the distance to the imaging system.

Throughout the present disclosure, any reference to "light," unless specifically in reference to visible light, can include electromagnetic radiation (EMR) or photons in the visible and/or non-visible portions of the EMR wavelength spectrum. The visible spectrum, sometimes referred to as the optical spectrum or luminous spectrum, is that portion of the electromagnetic spectrum that is visible to (e.g., can be detected by) the human eye and may be referred to as "visible light" or simply "light." A typical human eye will respond to wavelengths in air that are from about 380 nm to about 750 nm. The invisible spectrum (e.g., the non-luminous spectrum) is that portion of the electromagnetic spectrum that lies below and above the visible spectrum. The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

FIG. 1 illustrates one embodiment of a surgical visualization system 100. The surgical visualization system 100 is configured to create a visual representation of a critical structure 101 within an anatomical field. The critical structure 101 can include a single critical structure or a plurality of critical structures. As discussed herein, the critical structure 101 can be any of a variety of structures, such as an anatomical structure, e.g., a ureter, an artery such as a superior mesenteric artery, a vein such as a portal vein, a nerve such as a phrenic nerve, a vessel, a tumor, or other anatomical structure, or a foreign structure, e.g., a surgical device, a surgical fastener, a surgical clip, a surgical tack, a bougie, a surgical band, a surgical plate, or other foreign structure. As discussed herein, the critical structure 101 can be identified on a patient-by-patient and/or a procedure-by-procedure basis. Embodiments of critical structures and of identifying critical structures using a visualization system are further described in U.S. Pat. No. 10,792,034 entitled "Visualization Of Surgical Devices" issued Oct. 6, 2020, which is hereby incorporated by reference in its entirety.

In some instances, the critical structure 101 can be embedded in tissue 103. The tissue 103 can be any of a variety of tissues, such as fat, connective tissue, adhesions, and/or organs. Stated differently, the critical structure 101 may be positioned below a surface 105 of the tissue 103. In such instances, the tissue 103 conceals the critical structure 101 from the medical practitioner's "naked eye" view. The tissue 103 also obscures the critical structure 101 from the view of an imaging device 120 of the surgical visualization system 100. Instead of being fully obscured, the critical structure 101 can be partially obscured from the view of the medical practitioner and/or the imaging device 120.

The surgical visualization system 100 can be used for clinical analysis and/or medical intervention. In certain instances, the surgical visualization system 100 can be used intraoperatively to provide real-time information to the medical practitioner during a surgical procedure, such as real-time information regarding proximity data, dimensions, and/or distances. A person skilled in the art will appreciate that information may not be precisely real time but nevertheless be considered to be real time for any of a variety of reasons, such as time delay induced by data transmission, time delay induced by data processing, and/or sensitivity of measurement equipment. The surgical visualization system 100 is configured for intraoperative identification of critical structure(s) and/or to facilitate the avoidance of the critical structure(s) 101 by a surgical device. For example, by identifying the critical structure 101, a medical practitioner can avoid maneuvering a surgical device around the critical structure 101 and/or a region in a predefined proximity of the critical structure 101 during a surgical procedure. For another example, by identifying the critical structure 101, a medical practitioner can avoid dissection of and/or near the critical structure 101, thereby helping to prevent damage to the critical structure 101 and/or helping to prevent a surgical device being used by the medical practitioner from being damaged by the critical structure 101.

The surgical visualization system 100 is configured to incorporate tissue identification and geometric surface mapping in combination with the surgical visualization system's distance sensor system 104. In combination, these features of the surgical visualization system 100 can determine a position of a critical structure 101 within the anatomical field and/or the proximity of a surgical device 102 to the surface 105 of visible tissue 103 and/or to the critical structure 101. Moreover, the surgical visualization system 100 includes an imaging system that includes the imaging device 120 configured to provide real-time views of the surgical site. The imaging device 120 can include, for example, a spectral camera (e.g., a hyperspectral camera, multispectral camera, or selective spectral camera), which is configured to detect reflected spectral waveforms and generate a spectral cube of images based on the molecular response to the different wavelengths. Views from the imaging device 120 can be provided in real time to a medical practitioner, such as on a display (e.g., a monitor, a computer tablet screen, etc.). The displayed views can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intra-operatively provide advanced data synthesis and integrated information to the medical practitioner.

The imaging device 120 can be configured to detect visible light, spectral light waves (visible or invisible), and a structured light pattern (visible or invisible). Examples of the imaging device 120 includes scopes, e.g., an endoscope, an arthroscope, an angioscope, a bronchoscope, a choledochoscope, a colonoscope, a cytoscope, a duodenoscope, an enteroscope, an esophagogastro-duodenoscope (gastroscope), a laryngoscope, a nasopharyngo-neproscope, a sigmoidoscope, a thoracoscope, an ureteroscope, or an exoscope. Scopes can be particularly useful in minimally invasive surgical procedures. In open surgery applications, the imaging device 120 may not include a scope.

The tissue identification subsystem can be achieved with a spectral imaging system. The spectral imaging system can rely on imaging such as hyperspectral imaging, multispectral imaging, or selective spectral imaging. Embodiments of hyperspectral imaging of tissue are further described in U.S. Pat. No. 9,274,047 entitled "System And Method For Gross Anatomic Pathology Using Hyperspectral Imaging" issued Mar. 1, 2016, which is hereby incorporated by reference in its entirety.

The surface mapping subsystem can be achieved with a light pattern system. Various surface mapping techniques using a light pattern (or structured light) for surface mapping can be utilized in the surgical visualization systems described herein. Structured light is the process of projecting a known pattern (often a grid or horizontal bars) on to a surface. In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Embodiments of surface mapping and a surgical system including a light source and a projector for projecting a light pattern are further described in U.S. Pat. Pub. No. 2017/0055819 entitled "Set Comprising A Surgical Instrument" published Mar. 2, 2017, U.S. Pat. Pub. No. 2017/0251900 entitled "Depiction System" published Sep. 7, 2017, and U.S. Pat. Pub. No. 2021/0196385 entitled "Surgical Systems For Generating Three Dimensional Constructs Of Anatomical Organs And Coupling Identified Anatomical Structures Thereto" published Jul. 1, 2021, which are hereby incorporated by reference in their entireties.

The distance determining system can be incorporated into the surface mapping system. For example, structured light can be utilized to generate a three-dimensional (3D) virtual model of the visible surface 105 and determine various distances with respect to the visible surface 105. Additionally or alternatively, the distance determining system can rely on time-of-flight measurements to determine one or more distances to the identified tissue (or other structures) at the surgical site.

The surgical visualization system 100 also includes a surgical device 102. The surgical device 102 can be any suitable surgical device. Examples of the surgical device 102 includes a surgical dissector, a surgical stapler, a surgical grasper, a clip applier, a smoke evacuator, a surgical energy device (e.g., mono-polar probes, bi-polar probes, ablation probes, an ultrasound device, an ultrasonic end effector, etc.), etc. In some embodiments, the surgical device 102 includes an end effector having opposing jaws that extend from a distal end of a shaft of the surgical device 102 and that are configured to engage tissue therebetween.

The surgical visualization system 100 can be configured to identify the critical structure 101 and a proximity of the surgical device 102 to the critical structure 101. The imaging device 120 of the surgical visualization system 100 is configured to detect light at various wavelengths, such as visible light, spectral light waves (visible or invisible), and a structured light pattern (visible or invisible). The imaging device 120 can include a plurality of lenses, sensors, and/or receivers for detecting the different signals. For example, the imaging device 120 can be a hyperspectral, multispectral, or selective spectral camera, as described herein. The imaging device 120 can include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a 3D image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, a field of view of the imaging device 120 can overlap with a pattern of light (structured light) on the surface 105 of the tissue 103, as shown in FIG. 1.

As in this illustrated embodiment, the surgical visualization system 100 can be incorporated into a robotic surgical system 110. The robotic surgical system 110 can have a variety of configurations, as discussed herein. In this illustrated embodiment, the robotic surgical system 110 includes a first robotic arm 112 and a second robotic arm 114. The robotic arms 112, 114 each include rigid structural members 116 and joints 118, which can include servomotor controls. The first robotic arm 112 is configured to maneuver the surgical device 102, and the second robotic arm 114 is configured to maneuver the imaging device 120. A robotic control unit of the robotic surgical system 110 is configured to issue control motions to the first and second robotic arms 112, 114, which can affect the surgical device 102 and the imaging device 120, respectively.

In some embodiments, one or more of the robotic arms 112, 114 can be separate from the main robotic system 110 used in the surgical procedure. For example, at least one of the robotic arms 112, 114 can be positioned and registered to a particular coordinate system without a servomotor control. For example, a closed-loop control system and/or a plurality of sensors for the robotic arms 112, 114 can control and/or register the position of the robotic arm(s) 112, 114 relative to the particular coordinate system. Similarly, the position of the surgical device 102 and the imaging device 120 can be registered relative to a particular coordinate system.

Examples of robotic surgical systems include the Ottava™ robotic-assisted surgery system (Johnson & Johnson of New Brunswick, NJ), da Vinci® surgical systems (Intuitive Surgical, Inc. of Sunnyvale, CA), the Hugo™ robotic-assisted surgery system (Medtronic PLC of Minneapolis, MN), the Versius® surgical robotic system (CMR Surgical Ltd of Cambridge, UK), and the Monarch® platform (Auris Health, Inc. of Redwood City, CA). Embodiments of various robotic surgical systems and using robotic surgical systems are further described in U.S. Pat. Pub. No. 2018/0177556 entitled "Flexible Instrument Insertion Using An Adaptive Force Threshold" filed Dec. 28, 2016, U.S. Pat. Pub. No. 2020/0000530 entitled "Systems And Techniques For Providing Multiple Perspectives During Medical Procedures" filed Apr. 16, 2019, U.S. Pat. Pub. No. 2020/0170720 entitled "Image-Based Branch Detection And Mapping For Navigation" filed Feb. 7, 2020, U.S. Pat. Pub. No. 2020/0188043 entitled "Surgical Robotics System" filed Dec. 9, 2019, U.S. Pat. Pub. No. 2020/0085516 entitled "Systems And Methods For Concomitant Medical Procedures" filed Sep. 3, 2019, U.S. Pat. No. 8,831,782 entitled "Patient-Side Surgeon Interface For A Teleoperated Surgical Instrument" filed Jul. 15, 2013, and Intl. Pat. Pub. No. WO 2014151621 entitled "Hyperdexterous Surgical System" filed Mar. 13, 2014, which are hereby incorporated by reference in their entireties.

The surgical visualization system 100 also includes an emitter 106. The emitter 106 is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120. In one aspect, the projected light array 130 is employed by the surgical visualization system 100 to determine the shape defined by the surface 105 of the tissue 103 and/or motion of the surface 105 intraoperatively. The imaging device 120 is configured to detect the projected light arrays 130 reflected from the surface 105 to determine the topography of the surface 105 and various distances with respect to the surface 105.

As in this illustrated embodiment, the imaging device 120 can include an optical waveform emitter 123, such as by being mounted on or otherwise attached on the imaging device 120. The optical waveform emitter 123 is configured to emit electromagnetic radiation 124 (near-infrared (NIR) photons) that can penetrate the surface 105 of the tissue 103 and reach the critical structure 101. The imaging device 120 and the optical waveform emitter 123 can be positionable by the robotic arm 114. The optical waveform emitter 123 is mounted on or otherwise on the imaging device 120 but in other embodiments can be positioned on a separate surgical device from the imaging device 120. A corresponding waveform sensor 122 (e.g., an image sensor, spectrometer, or vibrational sensor) of the imaging device 120 is configured to detect the effect of the electromagnetic radiation received by the waveform sensor 122. The wavelengths of the electromagnetic radiation 124 emitted by the optical waveform emitter 123 are configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 can be variable. The waveform sensor 122 and optical waveform emitter 123 can be inclusive of a multispectral imaging system and/or a selective spectral imaging system, for example. In other instances, the waveform sensor 122 and optical waveform emitter 123 can be inclusive of a photoacoustic imaging system, for example.

The distance sensor system 104 of the surgical visualization system 100 is configured to determine one or more distances at the surgical site. The distance sensor system 104 can be a time-of-flight distance sensor system that includes an emitter, such as the emitter 106 as in this illustrated embodiment, and that includes a receiver 108. In other instances, the time-of-flight emitter can be separate from the structured light emitter. The emitter 106 can include a very tiny laser source, and the receiver 108 can include a matching sensor. The distance sensor system 104 is configured to detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104.

The receiver 108 of the distance sensor system 104 is positioned on the surgical device 102 in this illustrated embodiment, but in other embodiments the receiver 108 can be mounted on a separate surgical device instead of the surgical device 102. For example, the receiver 108 can be mounted on a cannula or trocar through which the surgical device 102 extends to reach the surgical site. In still other embodiments, the receiver 108 for the distance sensor system 104 can be mounted on a separate robotically-controlled arm of the robotic system 110 (e.g., on the second robotic arm 114) than the first robotic arm 112 to which the surgical device 102 is coupled, can be mounted on a movable arm that is operated by another robot, or be mounted to an operating room (OR) table or fixture. In some embodiments, the imaging device 120 includes the receiver 108 to allow for determining the distance from the emitter 106 to the surface 105 of the tissue 103 using a line between the emitter 106 on the surgical device 102 and the imaging device 120. For example, a distance $d_e$ can be triangulated based on known positions of the emitter 106 (on the surgical device 102) and the receiver 108 (on the imaging device 120) of the distance sensor system 104. The 3D position of the receiver 108 can be known and/or registered to the robot coordinate plane intraoperatively.

As in this illustrated embodiment, the position of the emitter 106 of the distance sensor system 104 can be controlled by the first robotic arm 112, and the position of the receiver 108 of the distance sensor system 104 can be controlled by the second robotic arm 114. In other embodiments, the surgical visualization system 100 can be utilized apart from a robotic system. In such instances, the distance sensor system 104 can be independent of the robotic system.

In FIG. 1, distance $d_e$ is emitter-to-tissue distance from the emitter 106 to the surface 105 of the tissue 103, and distance $d_e$ is device-to-tissue distance from a distal end of the surgical device 102 to the surface 105 of the tissue 103. The distance sensor system 104 is configured to determine the emitter-to-tissue distance $d_e$. The device-to-tissue distance $d_e$ is obtainable from the known position of the emitter 106 on the surgical device 102, e.g., on a shaft thereof proximal to the surgical device's distal end, relative to the distal end of the surgical device 102. In other words, when the distance between the emitter 106 and the distal end of the surgical device 102 is known, the device-to-tissue distance $d_e$ can be determined from the emitter-to-tissue distance $d_e$. In some embodiments, the shaft of the surgical device 102 can include one or more articulation joints and can be articulatable with respect to the emitter 106 and jaws at the distal end of the surgical device 102. The articulation configuration can include a multi-joint vertebrae-like structure, for example. In some embodiments, a 3D camera can be utilized to triangulate one or more distances to the surface 105.

In FIG. 1, distance $d_w$ is camera-to-critical structure distance from the optical waveform emitter 123 located on the imaging device 120 to the surface of the critical structure 101, and distance $d_A$ is a depth of the critical structure 101 below the surface 105 of the tissue 103 (e.g., the distance between the portion of the surface 105 closest to the surgical device 102 and the critical structure 101). The time-of-flight of the optical waveforms emitted from the optical waveform emitter 123 located on the imaging device 120 are configured to determine the camera-to-critical structure distance $d_w$.

Figure 2:
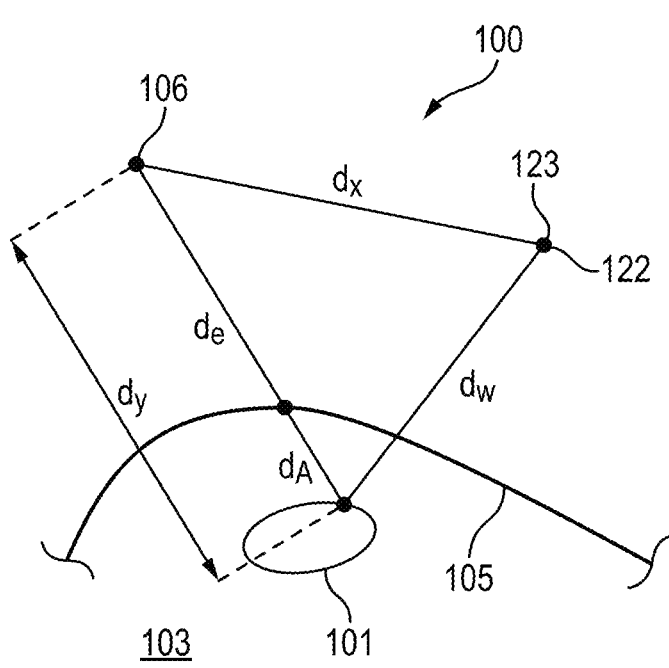
FIG. 2 is a schematic view of triangularization between a surgical device, an imaging device, and a critical structure of FIG. 1.

As shown in FIG. 2, the depth $d_A$ of the critical structure 101 relative to the surface 105 of the tissue 103 can be determined by triangulating from the camera-to-critical structure distance $d_w$ and known positions of the emitter 106 on the surgical device 102 and the optical waveform emitter 123 on the imaging device 120 (and, thus, the known distance $d_x$ therebetween) to determine distance dy, which is the sum of the distances $d_e$ and $d_A$. Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, the distance $d_A$ can be determined from an ultrasound, a registered magnetic resonance imaging (MRI), or computerized tomography (CT) scan. In still other instances, the distance $d_A$ can be determined with spectral imaging because the detection signal received by the imaging device 120 can vary based on the type of material, e.g., type of the tissue 103. For example, fat can decrease the detection signal in a first way, or a first amount, and collagen can decrease the detection signal in a different, second way, or a second amount.

Figure 3:
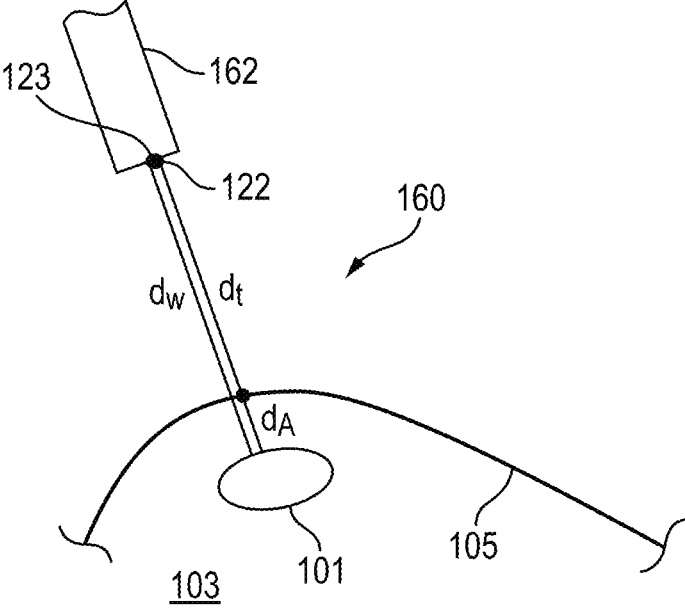
FIG. 3 is a schematic view of another embodiment of a surgical visualization system.

In another embodiment of a surgical visualization system 160 illustrated in FIG. 3, a surgical device 162, and not the imaging device 120, includes the optical waveform emitter 123 and the waveform sensor 122 that is configured to detect the reflected waveforms. The optical waveform emitter 123 is configured to emit waveforms for determining the distances $d_t$ and $d_w$ from a common device, such as the surgical device 162, as described herein. In such instances, the distance $d_A$ from the surface 105 of the tissue 103 to the surface of the critical structure 101 can be determined as follows:

$$d_A = d_w - d_t$$

Figure 4:
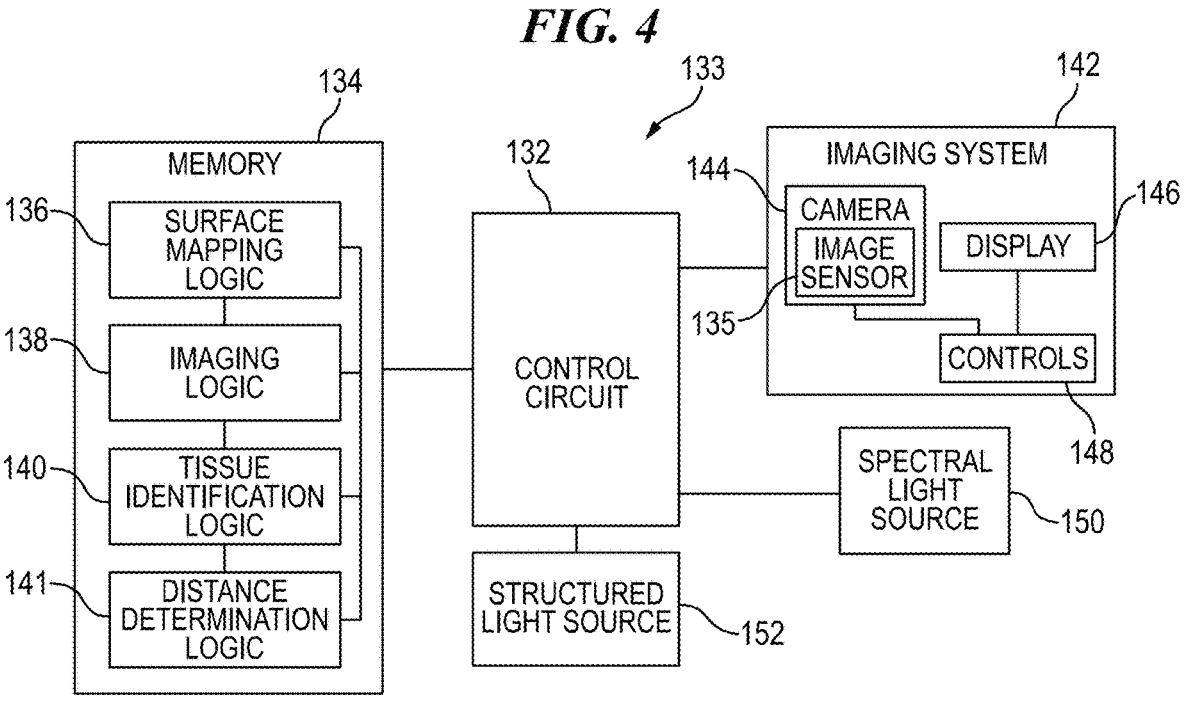
FIG. 4 is a schematic view of one embodiment of a control system for a surgical visualization system.

The surgical visualization system 100 includes a control system configured to control various aspects of the surgical visualization system 100. FIG. 4 illustrates one embodiment of a control system 133 that can be utilized as the control system of the surgical visualization system 100 (or other surgical visualization system described herein). The control system 133 includes a control circuit 132 configured to be in signal communication with a memory 134. The memory 134 is configured to store instructions executable by the control circuit 132, such as instructions to determine and/or recognize critical structures (e.g., the critical structure 101 of FIG. 1), instructions to determine and/or compute one or more distances and/or three-dimensional digital representations, and instructions to communicate information to a medical practitioner. As in this illustrated embodiment, the memory 134 can store surface mapping logic 136, imaging logic 138, tissue identification logic 140, and distance determining logic 141, although the memory 134 can store any combinations of the logics 136, 138, 140, 141 and/or can combine various logics together. The control system 133 also includes an imaging system 142 including a camera 144 (e.g., the imaging system including the imaging device 120 of FIG. 1), a display 146 (e.g., a monitor, a computer tablet screen, etc.), and controls 148 of the camera 144 and the display 146. The camera 144 includes an image sensor 135 (e.g., the waveform sensor 122) configured to receive signals from various light sources emitting light at various visible and invisible spectra (e.g., visible light, spectral imagers, three-dimensional lens, etc.). The display 146 is configured to depict real, virtual, and/or virtually-augmented images and/or information to a medical practitioner.

In an exemplary embodiment, the image sensor 135 is a solid-state electronic device containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of the image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors are sensitive to wavelengths in a range of about 350 nm to about 1050 nm, such as in a range of about 400 nm to about 1000 nm. A person skilled in the art will appreciate that a value may not be precisely at a value but nevertheless considered to be about that value for any of a variety of reasons, such as sensitivity of measurement equipment and manufacturing tolerances. CMOS sensors are, in general, more sensitive to IR wavelengths than CCD sensors. Solid state image sensors are based on the photo-electric effect and, as a result, cannot distinguish between colors. Accordingly, there are two types of color CCD cameras: single chip and three-chip. Single chip color CCD cameras offer a common, low-cost imaging solution and use a mosaic (e.g., Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes an emitter (e.g., the emitter 106) including a spectral light source 150 and a structured light source 152 each operably coupled to the control circuit 133. A single source can be pulsed to emit wavelengths of light in the spectral light source 150 range and wavelengths of light in the structured light source 152 range. Alternatively, a single light source can be pulsed to provide light in the invisible spectrum (e.g., infrared spectral light) and wavelengths of light on the visible spectrum. The spectral light source 150 can be, for example, a hyperspectral light source, a multispectral light source, and/or a selective spectral light source. The tissue identification logic 140 is configured to identify critical structure(s) (e.g., the critical structure 101 of FIG. 1) via data from the spectral light source 150 received by the image sensor 135 of the camera 144. The surface mapping logic 136 is configured to determine the surface contours of the visible tissue (e.g., the tissue 103) based on reflected structured light. With time-of-flight measurements, the distance determining logic 141 is configured to determine one or more distance(s) to the visible tissue and/or the critical structure. Output from each of the surface mapping logic 136, the tissue identification logic 140, and the distance determining logic 141 is configured to be provided to the imaging logic 138, and combined, blended, and/or overlaid by the imaging logic 138 to be conveyed to a medical practitioner via the display 146 of the imaging system 142.

Figure 5:
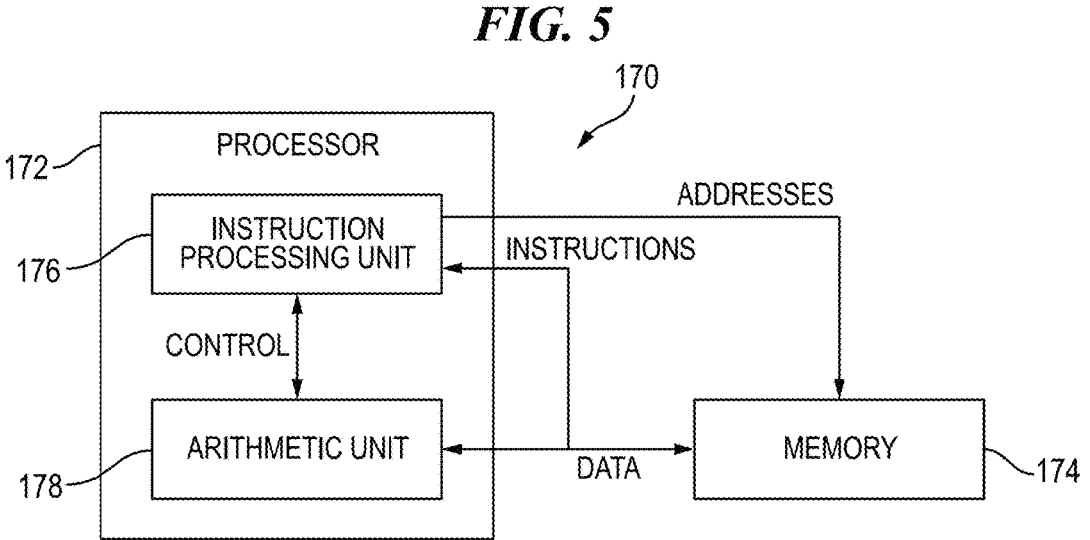
FIG. 5 is a schematic view of one embodiment of a control circuit of a control system for a surgical visualization system.

The control circuit 132 can have a variety of configurations. FIG. 5 illustrates one embodiment of a control circuit 170 that can be used as the control circuit 132 configured to control aspects of the surgical visualization system 100. The control circuit 170 is configured to implement various processes described herein. The control circuit 170 includes a microcontroller that includes a processor 172 (e.g., a microprocessor or microcontroller) operably coupled to a memory 174. The memory 174 is configured to store machine-executable instructions that, when executed by the processor 172, cause the processor 172 to execute machine instructions to implement various processes described herein. The processor 172 can be any one of a number of single-core or multicore processors known in the art. The memory 174 can include volatile and non-volatile storage media. The processor 172 includes an instruction processing unit 176 and an arithmetic unit 178. The instruction processing unit 176 is configured to receive instructions from the memory 174.

Figure 6:
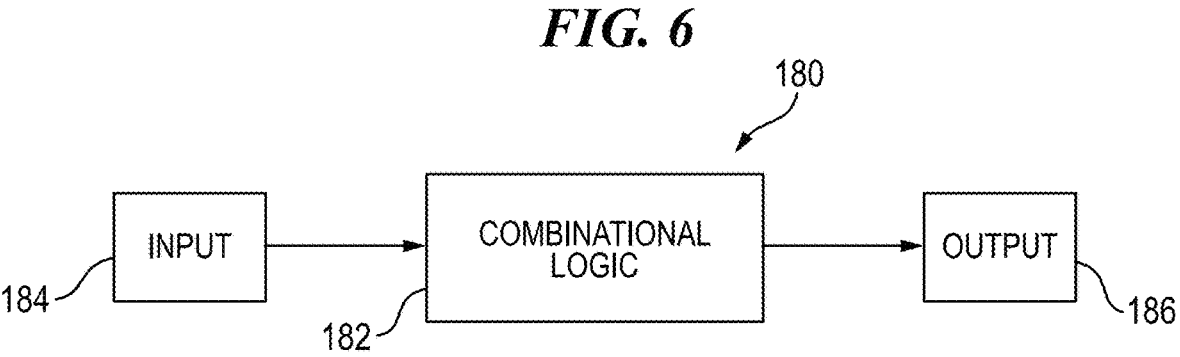
FIG. 6 is a schematic view of one embodiment of a combinational logic circuit of a surgical visualization system.

The surface mapping logic 136, the imaging logic 138, the tissue identification logic 140, and the distance determining logic 141 can have a variety of configurations. FIG. 6 illustrates one embodiment of a combinational logic circuit 180 configured to control aspects of the surgical visualization system 100 using logic such as one or more of the surface mapping logic 136, the imaging logic 138, the tissue identification logic 140, and the distance determining logic 141. The combinational logic circuit 180 includes a finite state machine that includes a combinational logic 182 configured to receive data associated with a surgical device (e.g. the surgical device 102 and/or the imaging device 120) at an input 184, process the data by the combinational logic 182, and provide an output 186 to a control circuit (e.g., the control circuit 132).

Figure 7:
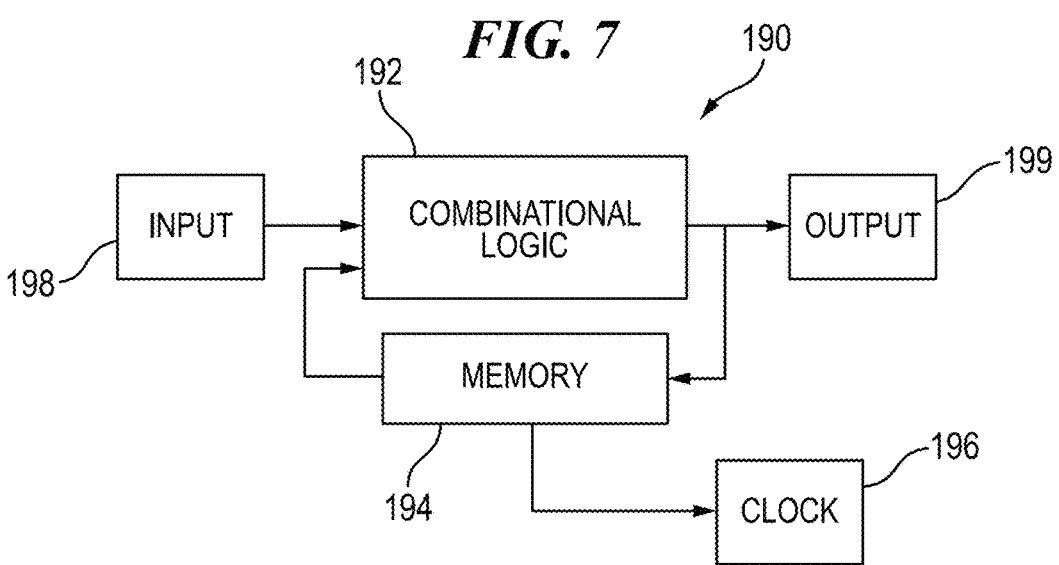
FIG. 7 is a schematic view of one embodiment of a sequential logic circuit of a surgical visualization system.

FIG. 7 illustrates one embodiment of a sequential logic circuit 190 configured to control aspects of the surgical visualization system 100 using logic such as one or more of the surface mapping logic 136, the imaging logic 138, the tissue identification logic 140, and the distance determining logic 141. The sequential logic circuit 190 includes a finite state machine that includes a combinational logic 192, a memory 194, and a clock 196. The memory 194 is configured to store a current state of the finite state machine. The sequential logic circuit 190 can be synchronous or asynchronous. The combinational logic 192 is configured to receive data associated with a surgical device (e.g. the surgical device 102 and/or the imaging device 120) at an input 198, process the data by the combinational logic 192, and provide an output 199 to a control circuit (e.g., the control circuit 132). In some embodiments, the sequential logic circuit 190 can include a combination of a processor (e.g., processor 172 of FIG. 5) and a finite state machine to implement various processes herein. In some embodiments, the finite state machine can include a combination of a combinational logic circuit (e.g., the combinational logic circuit 192 of FIG. 7) and the sequential logic circuit 190.

Figure 8:
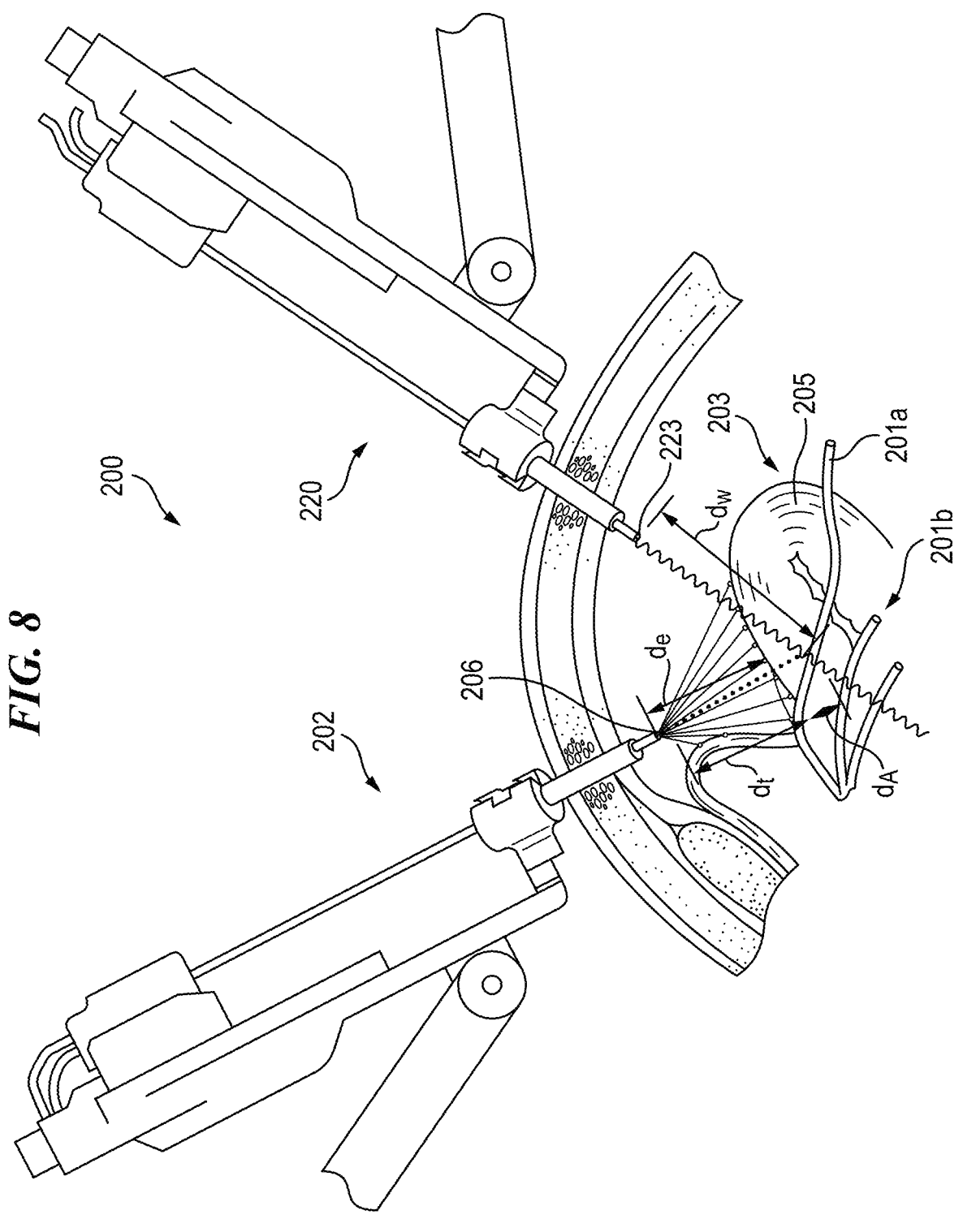
FIG. 8 is a schematic view of yet another embodiment of a surgical visualization system.

FIG. 8 illustrates another embodiment of a surgical visualization system 200. The surgical visualization system 200 is generally configured and used similar to the surgical visualization system 100 of FIG. 1, e.g., includes a surgical device 202 and an imaging device 220. The imaging device 220 includes a spectral light emitter 223 configured to emit spectral light in a plurality of wavelengths to obtain a spectral image of hidden structures, for example. The imaging device 220 can also include a three-dimensional camera and associated electronic processing circuits. The surgical visualization system 200 is shown being utilized intraoperatively to identify and facilitate avoidance of certain critical structures, such as a ureter 201$a$ and vessels 201$b$, in an organ 203 (a uterus in this embodiment) that are not visible on a surface 205 of the organ 203.

The surgical visualization system 200 is configured to determine an emitter-to-tissue distance $d_e$ from an emitter 206 on the surgical device 202 to the surface 205 of the uterus 203 via structured light. The surgical visualization system 200 is configured to extrapolate a device-to-tissue distance $d_t$ from the surgical device 202 to the surface 205 of the uterus 203 based on the emitter-to-tissue distance $d_e$. The surgical visualization system 200 is also configured to determine a tissue-to-ureter distance $d_A$ from the ureter 201$a$ to the surface 205 and a camera-to ureter distance $d_w$ from the imaging device 220 to the ureter 201$a$. As described herein, e.g., with respect to the surgical visualization system 100 of FIG. 1, the surgical visualization system 200 is configured to determine the distance $d_w$ with spectral imaging and time-of-flight sensors, for example. In various embodiments, the surgical visualization system 200 can determine (e.g., triangulate) the tissue-to-ureter distance $d_A$ (or depth) based on other distances and/or the surface mapping logic described herein.

Figure 9:
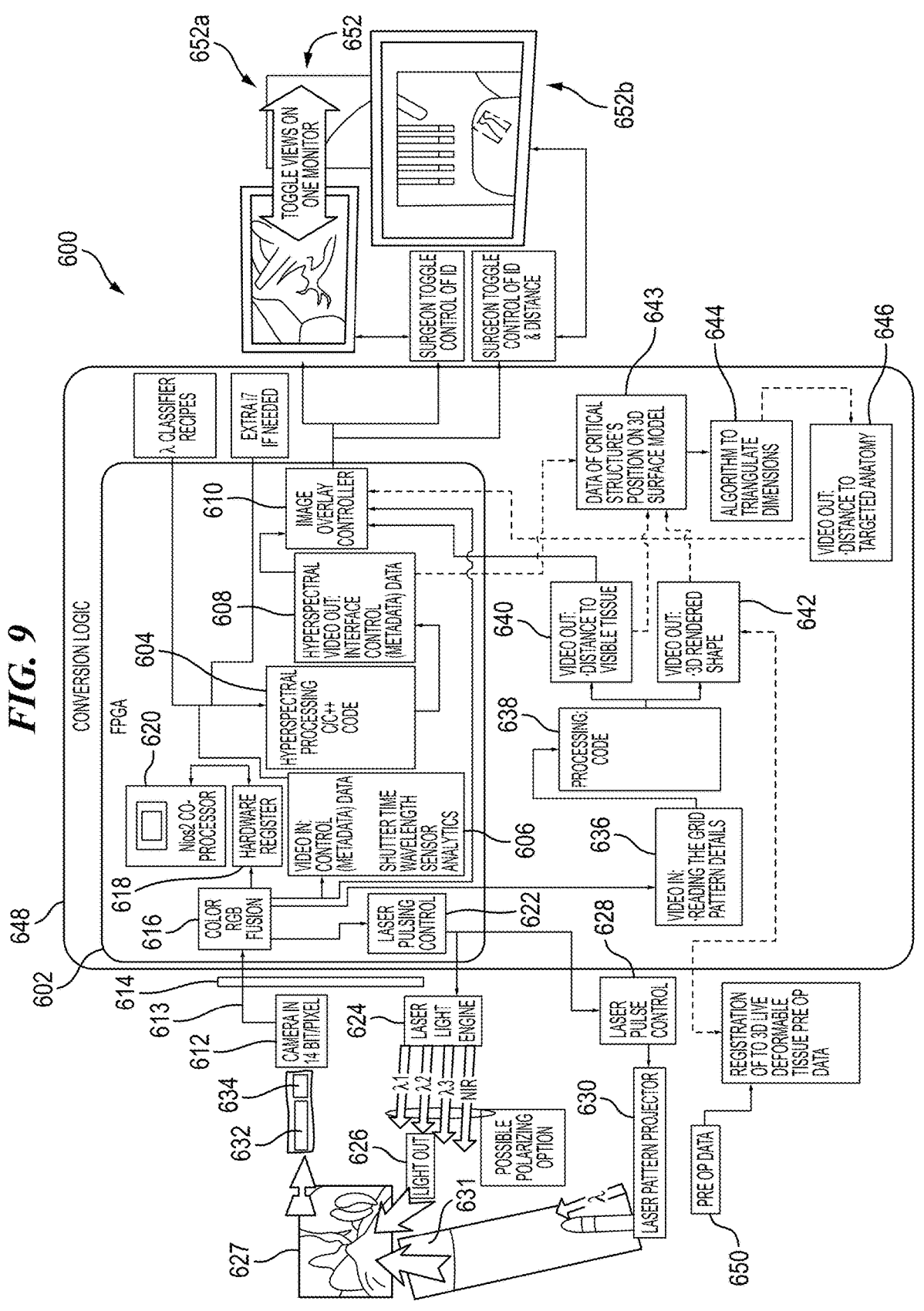
FIG. 9 is a schematic view of another embodiment of a control system for a surgical visualization system.

As mentioned above, a surgical visualization system includes a control system configured to control various aspects of the surgical visualization system. The control system can have a variety of configurations. FIG. 9 illustrates one embodiment of a control system 600 for a surgical visualization system, such as the surgical visualization system 100 of FIG. 1, the surgical visualization system 200 of FIG. 8, or other surgical visualization system described herein. The control system 600 is a conversion system that integrates spectral signature tissue identification and structured light tissue positioning to identify a critical structure, especially when those structure(s) are obscured by tissue, e.g., by fat, connective tissue, blood tissue, and/or organ(s), and/or by blood, and/or to detect tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 configured to convert tissue data to usable information for surgeons and/or other medical practitioners. For example, variable reflectance based on wavelengths with respect to obscuring material can be utilized to identify the critical structure in the anatomy. Moreover, the control system 600 is configured to combine the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various embodiments, the control system 600 is configured to provide warnings to a medical practitioner when in the proximity of one or more critical structures. Various algorithms can be employed to guide robotic automation and semiautomated approaches based on the surgical procedure and proximity to the critical structure(s).

A projected array of lights is employed by the control system 600 to determine tissue shape and motion intraoperatively. Alternatively, flash Lidar may be utilized for surface mapping of the tissue.

The control system 600 is configured to detect the critical structure, which as mentioned above can include one or more critical structures, and provide an image overlay of the critical structure and measure the distance to the surface of the visible tissue and the distance to the embedded/buried critical structure(s). The control system 600 can measure the distance to the surface of the visible tissue or detect the critical structure and provide an image overlay of the critical structure.

The control system 600 includes a spectral control circuit 602. The spectral control circuit 602 can be a field programmable gate array (FPGA) or another suitable circuit configuration, such as the configurations described with respect to FIG. 6, FIG. 7, and FIG. 8. The spectral control circuit 602 includes a processor 604 configured to receive video input signals from a video input processor 606. The processor 604 can be configured for hyperspectral processing and can utilize C/C++ code, for example. The video input processor 606 is configured to receive video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 is configured to provides the video output signal to an image overlay controller 610.

The video input processor 606 is operatively coupled to a camera 612 at the patient side via a patient isolation circuit 614. The camera 612 includes a solid state image sensor 634. The patient isolation circuit 614 can include a plurality of transformers so that the patient is isolated from other circuits in the system. The camera 612 is configured to receive intraoperative images through optics 632 and the image sensor 634. The image sensor 634 can include a CMOS image sensor, for example, or can include another image sensor technology, such as those discussed herein in connection with FIG. 4. The camera 612 is configured to output 613 images in 14 bit/pixel signals. A person skilled in the art will appreciate that higher or lower pixel resolutions can be employed. The isolated camera output signal 613 is provided to a color RGB fusion circuit 616, which in this illustrated embodiment employs a hardware register 618 and a Nios2 co-processor 620 configured to process the camera output signal 613. A color RGB fusion output signal is provided to the video input processor 606 and a laser pulsing control circuit 622.

The laser pulsing control circuit 622 is configured to control a laser light engine 624. The laser light engine 624 is configured to output light in a plurality of wavelengths ($\lambda 1, \lambda 2, \lambda 3, \ldots \lambda n$) including near infrared (NIR). The laser light engine 624 can operate in a plurality of modes. For example, the laser light engine 624 can operate in two modes. In a first mode, e.g., a normal operating mode, the laser light engine 624 is configured to output an illuminating signal. In a second mode, e.g., an identification mode, the laser light engine 624 is configured to output RGBG and NIR light. In various embodiments, the laser light engine 624 can operate in a polarizing mode.

Light output 626 from the laser light engine 624 is configured to illuminate targeted anatomy in an intraoperative surgical site 627. The laser pulsing control circuit 622 is also configured to control a laser pulse controller 628 for a laser pattern projector 630 configured to project a laser light pattern 631, such as a grid or pattern of lines and/or dots, at a predetermined wavelength ($\lambda$2) on an operative tissue or organ at the surgical site 627. The camera 612 is configured to receive the patterned light as well as the reflected light output through the camera optics 632. The image sensor 634 is configured to convert the received light into a digital signal.

The color RGB fusion circuit 616 is also configured to output signals to the image overlay controller 610 and a video input module 636 for reading the laser light pattern 631 projected onto the targeted anatomy at the surgical site 627 by the laser pattern projector 630. A processing module 638 is configured to process the laser light pattern 631 and output a first video output signal 640 representative of the distance to the visible tissue at the surgical site 627. The data is provided to the image overlay controller 610. The processing module 638 is also configured to output a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 is configured to determine the distance (e.g., distance $d_A$ of FIG. 1) to a buried critical structure (e.g., via triangularization algorithms 644), and the distance to the buried critical structure can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650, such as from a CT or MRI scan, can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Embodiments of registration of preoperative data are further described in U.S. Pat. Pub. No. 2020/0015907 entitled "Integration Of Imaging Data" filed Sep. 11, 2018, which is hereby incorporated by reference herein in its entirety.

The video monitors 652 are configured to output the integrated/augmented views from the image overlay controller 610. A medical practitioner can select and/or toggle between different views on one or more displays. On a first display 652a, which is a monitor in this illustrated embodiment, the medical practitioner can toggle between (A) a view in which a three-dimensional rendering of the visible tissue is depicted and (B) an augmented view in which one or more hidden critical structures are depicted over the three-dimensional rendering of the visible tissue. On a second display 652b, which is a monitor in this illustrated embodiment, the medical practitioner can toggle on distance measurements to one or more hidden critical structures and/or the surface of visible tissue, for example.

The various surgical visualization systems described herein can be utilized to visualize various different types of tissues and/or anatomical structures, including tissues and/or anatomical structures that may be obscured from being visualized by EMR in the visible portion of the spectrum. The surgical visualization system can utilize a spectral imaging system, as mentioned above, which can be configured to visualize different types of tissues based upon their varying combinations of constituent materials. In particular, a spectral imaging system can be configured to detect the presence of various constituent materials within a tissue being visualized based on the absorption coefficient of the tissue across various EMR wavelengths. The spectral imaging system can be configured to characterize the tissue type of the tissue being visualized based upon the particular combination of constituent materials.

Figure 10:
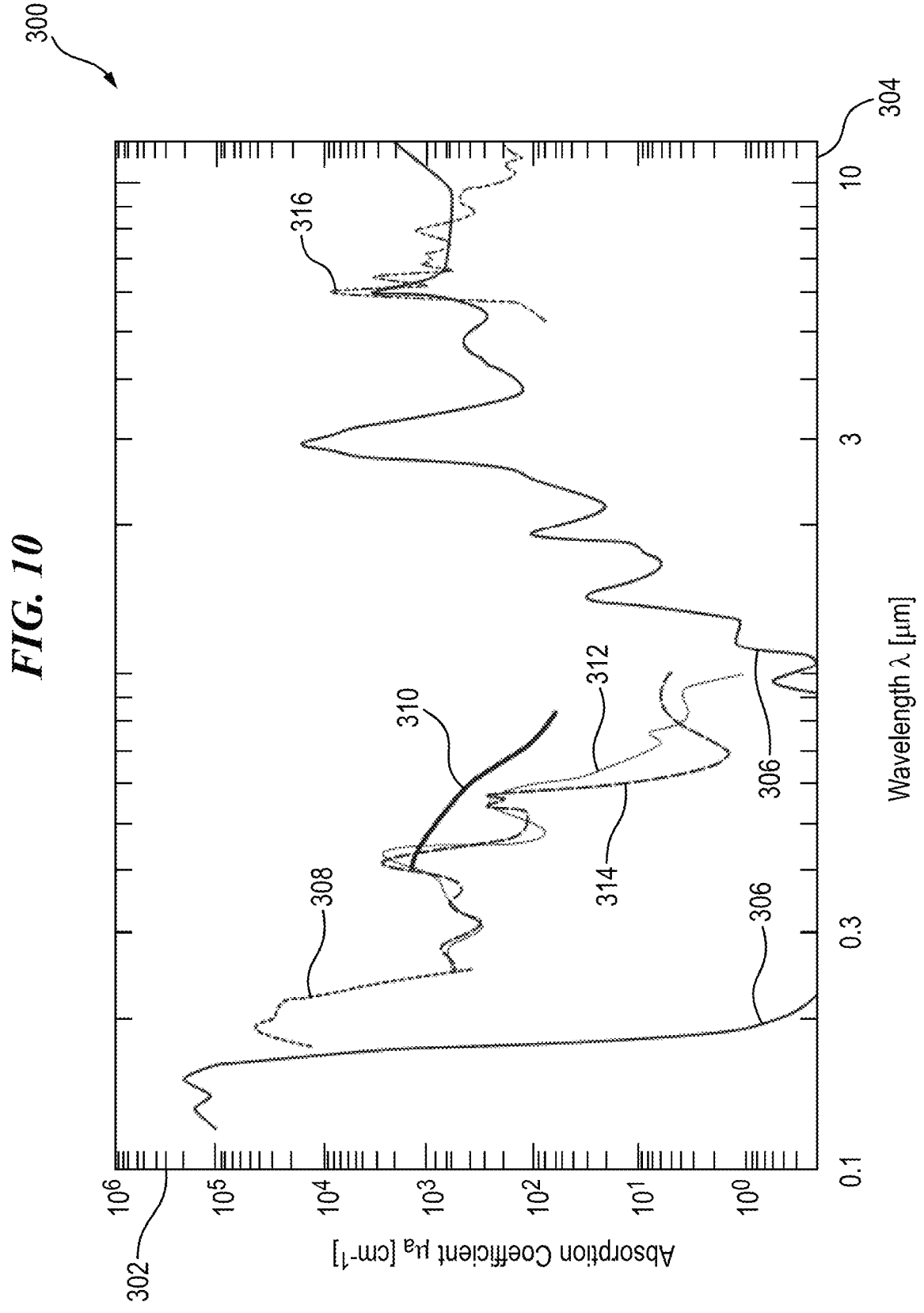
FIG. 10 is a graph showing wavelength versus absorption coefficient for various biological materials.

FIG. 10 shows a graph 300 depicting how the absorption coefficient of various biological materials varies across the EMR wavelength spectrum. In the graph 300, the vertical axis 302 represents absorption coefficient of the biological material in $cm^{-1}$, and the horizontal axis 304 represents EMR wavelength in $\mu$m. A first line 306 in the graph 300 represents the absorption coefficient of water at various EMR wavelengths, a second line 308 represents the absorption coefficient of protein at various EMR wavelengths, a third line 310 represents the absorption coefficient of melanin at various EMR wavelengths, a fourth line 312 represents the absorption coefficient of deoxygenated hemoglobin at various EMR wavelengths, a fifth line 314 represents the absorption coefficient of oxygenated hemoglobin at various EMR wavelengths, and a sixth line 316 represents the absorption coefficient of collagen at various EMR wavelengths. Different tissue types have different combinations of constituent materials and, therefore, the tissue type(s) being visualized by a surgical visualization system can be identified and differentiated between according to the particular combination of detected constituent materials. Accordingly, a spectral imaging system of a surgical visualization system can be configured to emit EMR at a number of different wavelengths, determine the constituent materials of the tissue based on the detected absorption EMR absorption response at the different wavelengths, and then characterize the tissue type based on the particular detected combination of constituent materials.

Figure 11:
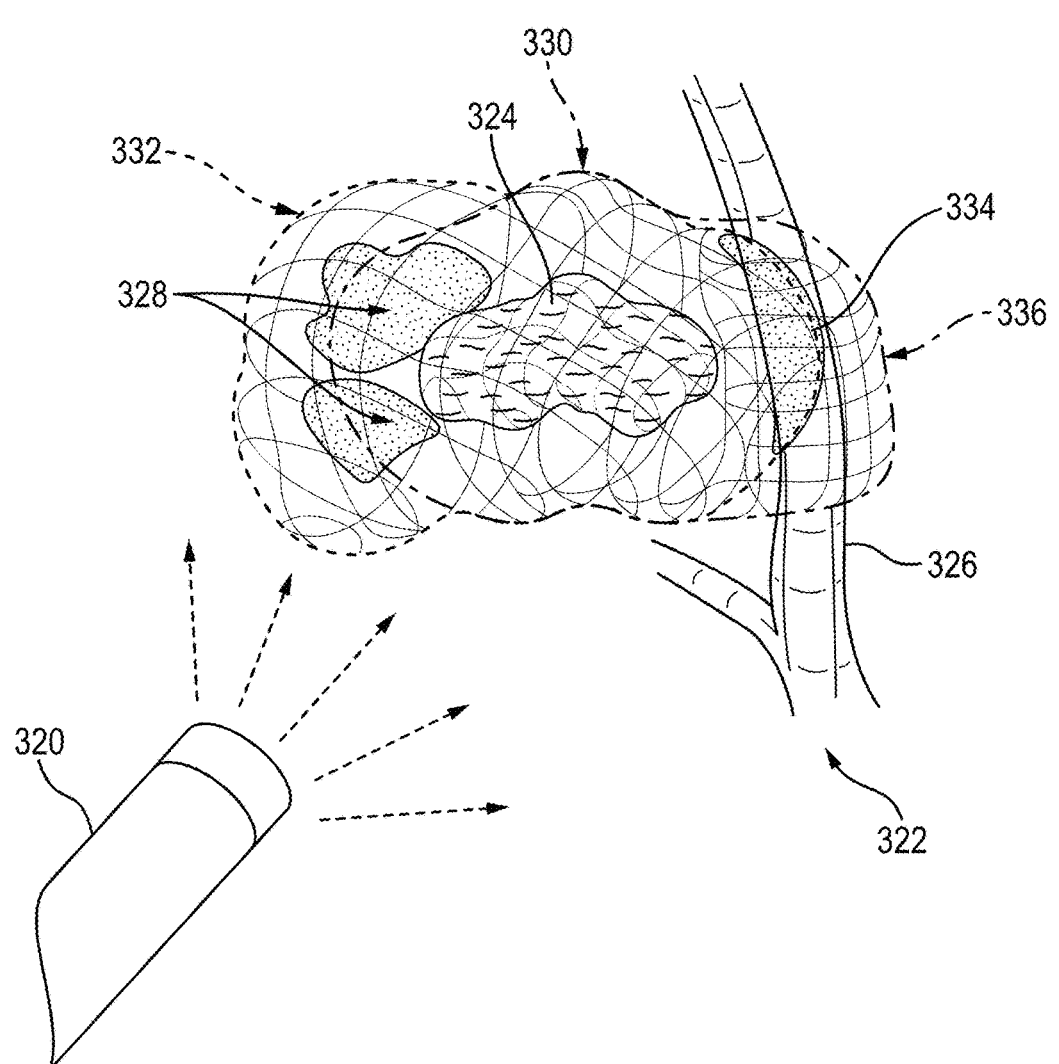
FIG. 11 is a schematic view of one embodiment of a spectral emitter visualizing a surgical site.

FIG. 11 shows an embodiment of the utilization of spectral imaging techniques to visualize different tissue types and/or anatomical structures. In FIG. 11, a spectral emitter 320 (e.g., the spectral light source 150 of FIG. 4) is being utilized by an imaging system to visualize a surgical site 322. The EMR emitted by the spectral emitter 320 and reflected from the tissues and/or structures at the surgical site 322 is received by an image sensor (e.g., the image sensor 135 of FIG. 4) to visualize the tissues and/or structures, which can be either visible (e.g., be located at a surface of the surgical site 322) or obscured (e.g., underlay other tissue and/or structures at the surgical site 322). In this embodiment, an imaging system (e.g., the imaging system 142 of FIG. 4) visualizes a tumor 324, an artery 326, and various abnormalities 328 (e.g., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system (e.g., the display 146 of the imaging system 142 of FIG. 4), on a primary display (e.g., the primary display 819 of FIG. 19), on a non-sterile display (e.g., the non-sterile displays 807, 809 of FIG. 19), on a display of a surgical hub (e.g., the display of the surgical hub 806 of FIG. 19), on a device/instrument display, and/or on another display.

The imaging system can be configured to tailor or update the displayed surgical site visualization according to the identified tissue and/or structure types. For example, as shown in FIG. 11, the imaging system can display a margin 330 associated with the tumor 324 being visualized on a display screen associated with or coupled to the imaging system, on a primary display, on a non-sterile display, on a display of a surgical hub, on a device/instrument display, and/or on another display. The margin 330 can indicate the area or amount of tissue that should be excised to ensure complete removal of the tumor 324. A size of the margin 330 can be, for example, in a range of about 5 mm to about 10 mm. The surgical visualization system's control system (e.g., the control system 133 of FIG. 4) can be configured to control or update the dimensions of the margin 330 based on the tissues and/or structures identified by the imaging system. In this illustrated embodiment, the imaging system has identified multiple abnormalities 328 within the field of view (FOV). Accordingly, the control system can adjust the displayed margin 330 to a first updated margin 332 having sufficient dimensions to encompass the abnormalities 328. Further, the imaging system has also identified the artery 326 partially overlapping with the initially displayed margin 330 (as indicated by a highlighted region 334 of the artery 326). Accordingly, the control system can adjust the displayed margin to a second updated margin 336 having sufficient dimensions to encompass the relevant portion of the artery 326.

Figure 12:
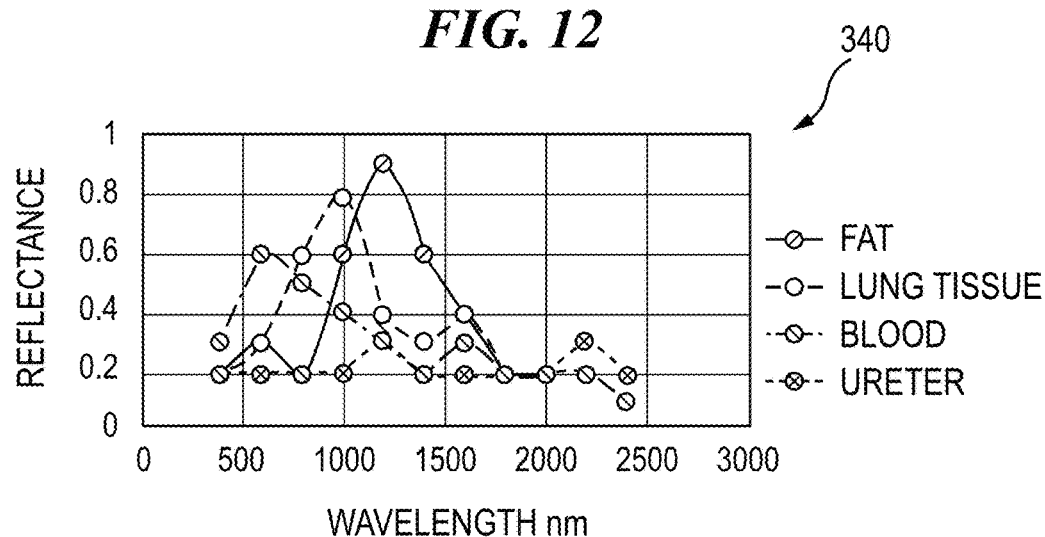
FIG. 12 is a graph depicting illustrative hyperspectral identifying signatures to differentiate a ureter from obscurants.
Figure 13:
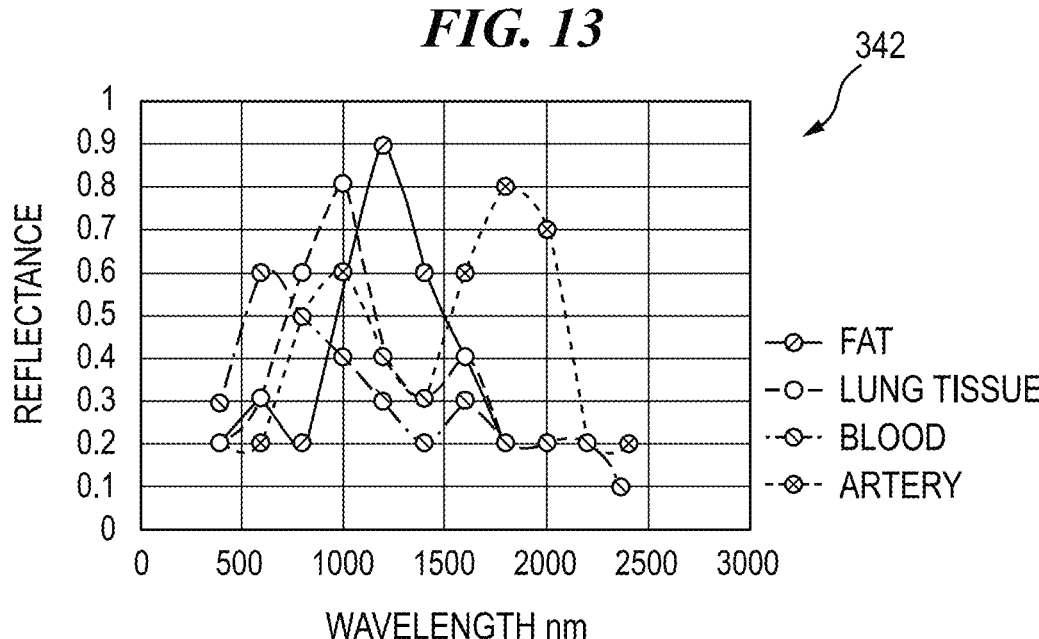
FIG. 13 is a graph depicting illustrative hyperspectral identifying signatures to differentiate an artery from obscurants.
Figure 14:
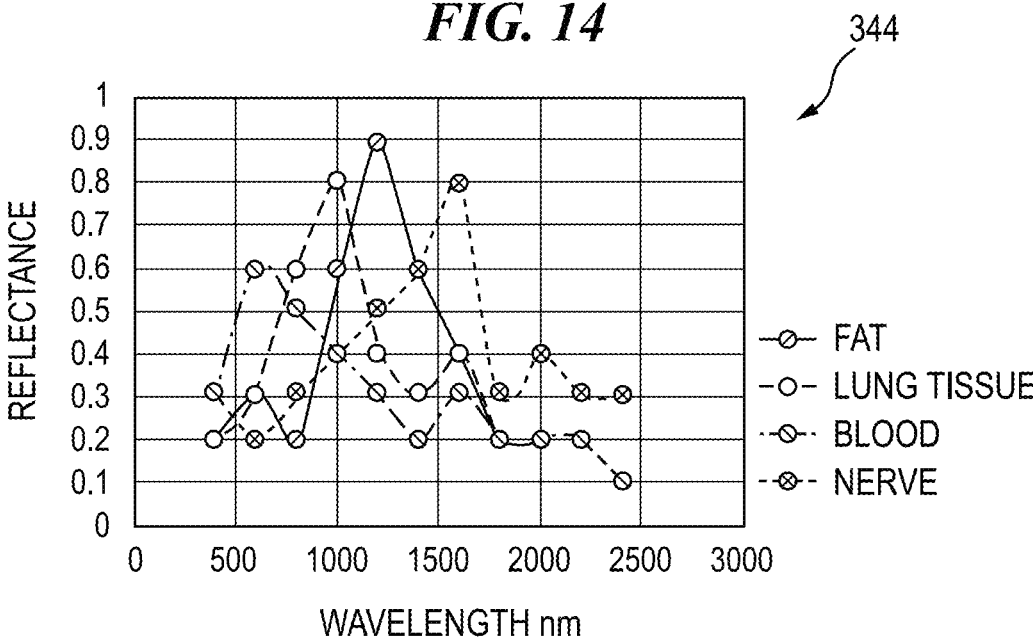
FIG. 14 is a graph depicting illustrative hyperspectral identifying signatures to differentiate a nerve from obscurants.

Tissues and/or structures can also be imaged or characterized according to their reflective characteristics, in addition to or in lieu of their absorptive characteristics described above with respect to FIG. 10 and FIG. 11, across the EMR wavelength spectrum. For example, FIG. 12, FIG. 13, and FIG. 14 illustrate various graphs of reflectance of different types of tissues or structures across different EMR wavelengths. FIG. 12 is a graphical representation 340 of an illustrative ureter signature versus obscurants. FIG. 13 is a graphical representation 342 of an illustrative artery signature versus obscurants. FIG. 14 is a graphical representation 344 of an illustrative nerve signature versus obscurants. The plots in FIG. 12, FIG. 13, and FIG. 14 represent reflectance as a function of wavelength (nm) for the particular structures (ureter, artery, and nerve) relative to the corresponding reflectances of fat, lung tissue, and blood at the corresponding wavelengths. These graphs are simply for illustrative purposes and it should be understood that other tissues and/or structures could have corresponding detectable reflectance signatures that would allow the tissues and/or structures to be identified and visualized.

Select wavelengths for spectral imaging can be identified and utilized based on the anticipated critical structures and/or obscurants at a surgical site (e.g., "selective spectral" imaging). By utilizing selective spectral imaging, the amount of time required to obtain the spectral image can be minimized such that the information can be obtained in real-time and utilized intraoperatively. The wavelengths can be selected by a medical practitioner or by a control circuit based on input by a user, e.g., a medical practitioner. In certain instances, the wavelengths can be selected based on machine learning and/or big data accessible to the control circuit via, e.g., a cloud or surgical hub.

Figures 15, 16:
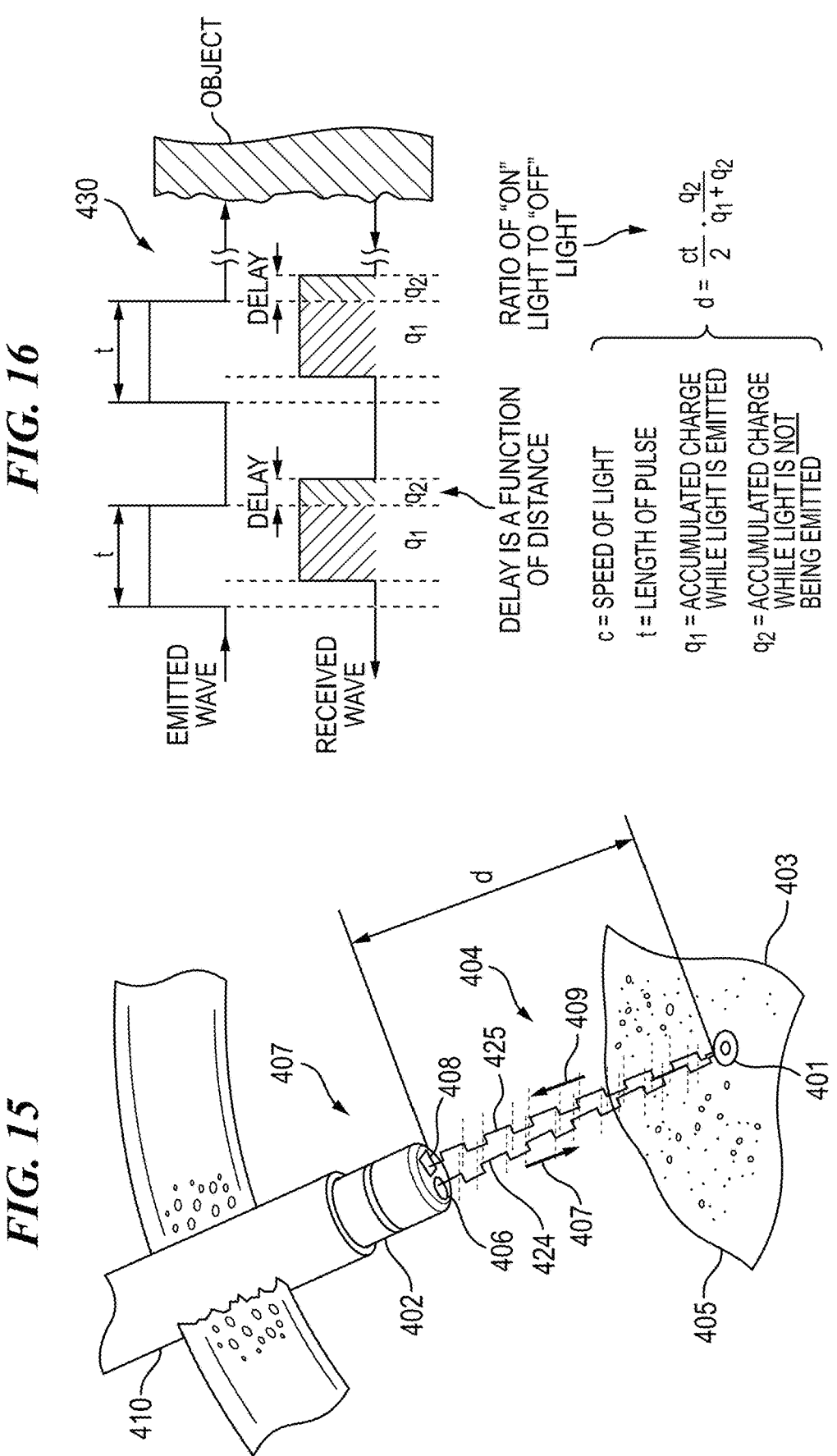
FIG. 15 is a schematic view of one embodiment of a near infrared (NIR) time-of-flight measurement system being utilized intraoperatively.
FIG. 16 shows a time-of-flight timing diagram for the system of FIG. 15.

FIG. 15 illustrates one embodiment of spectral imaging to tissue being utilized intraoperatively to measure a distance between a waveform emitter and a critical structure that is obscured by tissue. FIG. 15 shows an embodiment of a time-of-flight sensor system 404 utilizing waveforms 424, 425. The time-of-flight sensor system 404 can be incorporated into a surgical visualization system, e.g., as the sensor system 104 of the surgical visualization system 100 of FIG. 1. The time-of-flight sensor system 404 includes a waveform emitter 406 and a waveform receiver 408 on the same surgical device 402 (e.g., the emitter 106 and the receiver 108 on the same surgical device 102 of FIG. 1). The emitted wave 400 extends to a critical structure 401 (e.g., the critical structure 101 of FIG. 1) from the emitter 406, and the received wave 425 is reflected back to by the receiver 408 from the critical structure 401. The surgical device 402 in this illustrated embodiment is positioned through a trocar 410 that extends into a cavity 407 in a patient. Although the trocar 410 is used in this in this illustrated embodiment, other trocars or other access devices can be used, or no access device may be used.

The waveforms 424, 425 are configured to penetrate obscuring tissue 403, such as by having wavelengths in the NIR or SWIR spectrum of wavelengths. A spectral signal (e.g., hyperspectral, multispectral, or selective spectral) or a photoacoustic signal is emitted from the emitter 406, as shown by a first arrow 407 pointing distally, and can penetrate the tissue 403 in which the critical structure 401 is concealed. The emitted waveform 424 is reflected by the critical structure 401, as shown by a second arrow 409 pointing proximally. The received waveform 425 can be delayed due to a distance d between a distal end of the surgical device 402 and the critical structure 401. The waveforms 424, 425 can be selected to target the critical structure 401 within the tissue 403 based on the spectral signature of the critical structure 401, as described herein. The emitter 406 is configured to provide a binary signal on and off, as shown in FIG. 16, for example, which can be measured by the receiver 408.

Based on the delay between the emitted wave 424 and the received wave 425, the time-of-flight sensor system 404 is configured to determine the distance d. A time-of-flight timing diagram 430 for the emitter 406 and the receiver 408 of FIG. 15 is shown in FIG. 16. The delay is a function of the distance d and the distance d is given by:

$$d = \frac{ct}{2} \cdot \frac{q_2}{q_1 + q_2}$$

where c=the speed of light; t=length of pulse; $q_1$=accumulated charge while light is emitted; and $q_2$=accumulated charge while light is not being emitted.

The time-of-flight of the waveforms 424, 425 corresponds to the distance d in FIG. 15. In various instances, additional emitters/receivers and/or pulsing signals from the emitter 406 can be configured to emit a non-penetrating signal. The non-penetrating signal can be configured to determine the distance from the emitter 406 to the surface 405 of the obscuring tissue 403. In various instances, a depth of the critical structure 401 can be determined by:

$$d_A = d_w - d_t$$

where $d_A$=the depth of the critical structure 401; $d_w$=the distance from the emitter 406 to the critical structure 401 (d in FIG. 15); and $d_t$=the distance from the emitter 406 (on the distal end of the surgical device 402) to the surface 405 of the obscuring tissue 403.

Figure 17:
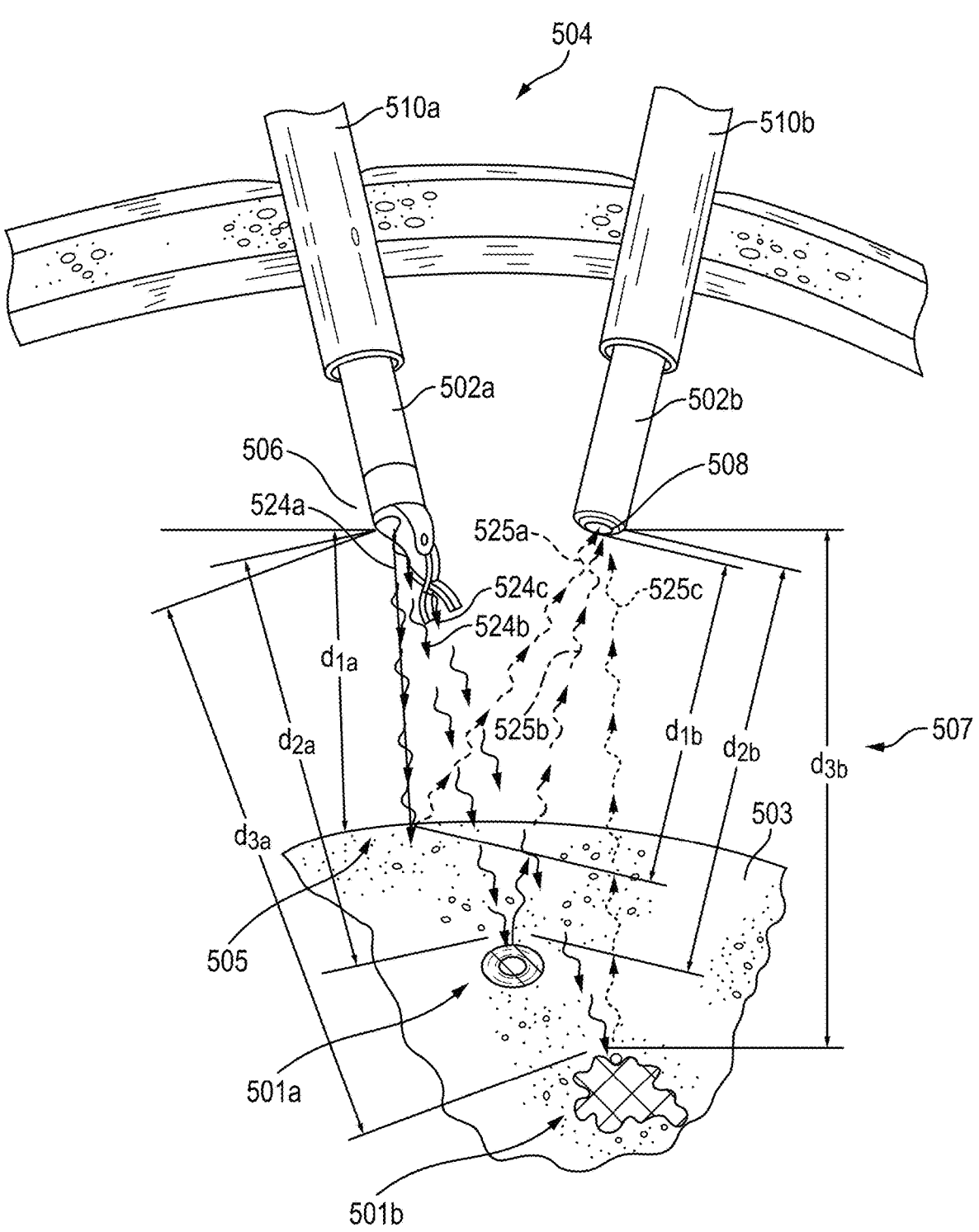
FIG. 17 is a schematic view of another embodiment of a near infrared (NIR) time-of-flight measurement system being utilized intraoperatively.

FIG. 17 illustrates another embodiment of a time-of-flight sensor system 504 utilizing waves 524a, 524b, 524c, 525a, 525b, 525c is shown. The time-of-flight sensor system 504 can be incorporated into a surgical visualization system, e.g., as the sensor system 104 of the surgical visualization system 100 of FIG. 1. The time-of-flight sensor system 504 includes a waveform emitter 506 and a waveform receiver 508 (e.g., the emitter 106 and the receiver 108 of FIG. 1). The waveform emitter 506 is positioned on a first surgical device 502a (e.g., the surgical device 102 of FIG. 1), and the waveform receiver 508 is positioned on a second surgical device 502b. The surgical devices 502a, 502b are positioned through first and second trocars 510a, 510b, respectively, which extend into a cavity 507 in a patient. Although the trocars 510a, 510b are used in this in this illustrated embodiment, other trocars or other access devices can be used, or no access device may be used. The emitted waves 524a, 524b, 524c extend toward a surgical site from the emitter 506, and the received waves 525a, 525b, 525c are reflected back to the receiver 508 from various structures and/or surfaces at the surgical site.

The different emitted waves 524a, 524b, 524c are configured to target different types of material at the surgical site. For example, the wave 524a targets obscuring tissue 503, the wave 524b targets a first critical structure 501a (e.g., the critical structure 101 of FIG. 1), which is a vessel in this illustrated embodiment, and the wave 524c targets a second critical structure 501b (e.g., the critical structure 101 of FIG. 1), which is a cancerous tumor in this illustrated embodiment. The wavelengths of the waves 524a, 524b, 524c can be in the visible light, NIR, or SWIR spectrum of wavelengths. For example, visible light can be reflected off a surface 505 of the tissue 503, and NIR and/or SWIR waveforms can penetrate the surface 505 of the tissue 503. In various aspects, as described herein, a spectral signal (e.g., hyperspectral, multispectral, or selective spectral) or a photoacoustic signal can be emitted from the emitter 506. The waves 524b, 524c can be selected to target the critical structures 501a, 501b within the tissue 503 based on the spectral signature of the critical structures 501a, 501b, as described herein. Photoacoustic imaging is further described in various U.S. patent applications, which are incorporated by reference herein in the present disclosure.

The emitted waves 524a, 524b, 524c are reflected off the targeted material, namely the surface 505, the first critical structure 501a, and the second structure 501b, respectively. The received waveforms 525a, 525b, 525c can be delayed due to distances $d_{1a}$, $d_{2a}$, $d_{3a}$, $d_{1b}$, $d_{2b}$, $d_{2c}$.

In the time-of-flight sensor system 504, in which the emitter 506 and the receiver 508 are independently positionable (e.g., on separate surgical devices 502a, 502b and/or controlled by separate robotic arms), the various distances $d_{1a}$, $d_{2a}$, $d_{3a}$, $d_{1b}$, $d_{2b}$, dec can be calculated from the known position of the emitter 506 and the receiver 508. For example, the positions can be known when the surgical devices 502a, 502b are robotically-controlled. Knowledge of the positions of the emitter 506 and the receiver 508, as well as the time of the photon stream to target a certain tissue and the information received by the receiver 508 of that particular response can allow a determination of the distances $d_{1a}$, $d_{2a}$, $d_{3a}$, $d_{1b}$, $d_{2b}$, $d_{2c}$. In one aspect, the distance to the obscured critical structures 501a, 501b can be triangulated using penetrating wavelengths. Because the speed of light is constant for any wavelength of visible or invisible light, the time-of-flight sensor system 504 can determine the various distances.

In a view provided to the medical practitioner, such as on a display, the receiver 508 can be rotated such that a center of mass of the target structure in the resulting images remains constant, e.g., in a plane perpendicular to an axis of a select target structure 503, 501a, or 501b. Such an orientation can quickly communicate one or more relevant distances and/or perspectives with respect to the target structure. For example, as shown in FIG. 17, the surgical site is displayed from a viewpoint in which the critical structure 501a is perpendicular to the viewing plane (e.g., the vessel is oriented in/out of the page). Such an orientation can be default setting; however, the view can be rotated or otherwise adjusted by a medical practitioner. In certain instances, the medical practitioner can toggle between different surfaces and/or target structures that define the viewpoint of the surgical site provided by the imaging system.

As in this illustrated embodiment, the receiver 508 can be mounted on the trocar 510b (or other access device) through which the surgical device 502b is positioned. In other embodiments, the receiver 508 can be mounted on a separate robotic arm for which the three-dimensional position is known. In various instances, the receiver 508 can be mounted on a movable arm that is separate from a robotic surgical system that controls the surgical device 502a or can be mounted to an operating room (OR) table or fixture that is intraoperatively registerable to the robot coordinate plane. In such instances, the position of the emitter 506 and the receiver 508 can be registerable to the same coordinate plane such that the distances can be triangulated from outputs from the time-of-flight sensor system 504.

Combining time-of-flight sensor systems and near-infrared spectroscopy (NIRS), termed TOF-NIRS, which is capable of measuring the time-resolved profiles of NIR light with nanosecond resolution can be found in "Time-Of-Flight Near-Infrared Spectroscopy For Nondestructive Measurement Of Internal Quality In Grapefruit," Journal of the American Society for Horticultural Science, May 2013 vol. 138 no. 3 225-228, which is hereby incorporated by reference in its entirety.

Embodiments of visualization systems and aspects and uses thereof are described further in U.S. Pat. Pub. No. 2020/0015923 entitled "Surgical Visualization Platform" filed Sep. 11, 2018, U.S. Pat. Pub. No. 2020/0015900 entitled "Controlling An Emitter Assembly Pulse Sequence" filed Sep. 11, 2018, U.S. Pat. Pub. No. 2020/0015668 entitled "Singular EMR Source Emitter Assembly" filed Sep. 11, 2018, U.S. Pat. Pub. No. 2020/0015925 entitled "Combination Emitter And Camera Assembly" filed Sep. 11, 2018, U.S. Pat. Pub. No. 2020/0015899 entitled "Surgical Visualization With Proximity Tracking Features" filed Sep. 11, 2018, U.S. Pat. Pub. No. 2020/0015903 entitled "Surgical Visualization Of Multiple Targets" filed Sep. 11, 2018, U.S. Pat. No. 10,792,034 entitled "Visualization Of Surgical Devices" filed Sep. 11, 2018, U.S. Pat. Pub. No. 2020/0015897 entitled "Operative Communication Of Light" filed Sep. 11, 2018, U.S. Pat. Pub. No. 2020/0015924 entitled "Robotic Light Projection Tools" filed Sep. 11, 2018, U.S. Pat. Pub. No. 2020/0015898 entitled "Surgical Visualization Feedback System" filed Sep. 11, 2018, U.S. Pat. Pub. No. 2020/0015906 entitled "Surgical Visualization And Monitoring" filed Sep. 11, 2018, U.S. Pat. Pub. No. 2020/0015907 entitled "Integration Of Imaging Data" filed Sep. 11, 2018, U.S. Pat. No. 10,925,598 entitled "Robotically-Assisted Surgical Suturing Systems" filed Sep. 11, 2018, U.S. Pat. Pub. No. 2020/0015901 entitled "Safety Logic For Surgical Suturing Systems" filed Sep. 11, 2018, U.S. Pat. Pub. No. 2020/0015914 entitled "Robotic Systems With Separate Photoacoustic Receivers" filed Sep. 11, 2018, U.S. Pat. Pub. No. 2020/0015902 entitled "Force Sensor Through Structured Light Deflection" filed Sep. 11, 2018, U.S. Pat. Pub. No. 2019/0201136 entitled "Method Of Hub Communication" filed Dec. 4, 2018, U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, U.S. patent application Ser. No. 16/729,807 entitled "Method Of Using Imaging Devices In Surgery" filed Dec. 30, 2019, U.S. patent application Ser. No. 17/493,913 entitled "Surgical Methods Using Fiducial Identification And Tracking" filed on Oct. 5, 2021, U.S. patent application Ser. No. 17/494,364 entitled "Surgical Methods For Control Of One Visualization With Another" filed on Oct. 5, 2021, U.S. patent application Ser. No. 17/450,020 entitled "Methods And Systems For Controlling Cooperative Surgical Instruments" filed on Oct. 5, 2021, U.S. patent application Ser. No. 17/450,025 entitled "Methods And Systems For Controlling Cooperative Surgical Instruments With Variable Surgical Site Access Trajectories" filed on Oct. 5, 2021, U.S. patent application Ser. No. 17/450,027 entitled "Methods And Systems For Controlling Cooperative Surgical Instruments" filed on Oct. 5, 2021, and U.S. patent application Ser. No. 17/449,765 entitled "Cooperative Access Hybrid Procedures" filed Oct. 1, 2021, which are hereby incorporated by reference in their entireties.

Surgical Hubs

The various visualization or imaging systems described herein can be incorporated into a system that includes a surgical hub. In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as one or more surgical instruments that are used to conduct medical procedures on patients and/or one or more visualization systems that are used during performance of medical procedures. The surgical hubs provide a wide array of functionality to improve the outcomes of medical procedures. The data generated by the various surgical devices, visualization systems, and surgical hubs about the patient and the medical procedure may be transmitted to the cloud-based medical analytics system. This data may then be aggregated with similar data gathered from many other surgical hubs, visualization systems, and surgical instruments located at other medical facilities. Various patterns and correlations may be found through the cloud-based analytics system analyzing the collected data. Improvements in the techniques used to generate the data may be generated as a result, and these improvements may then be disseminated to the various surgical hubs, visualization systems, and surgical instruments. Due to the interconnectedness of all of the aforementioned components, improvements in medical procedures and practices may be found that otherwise may not be found if the many components were not so interconnected.

Examples of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0201046 entitled "Method For Controlling Smart Energy Devices" filed Dec. 4, 2018, U.S. Pat. Pub. No. 2019/0201114 entitled "Adaptive Control Program Updates For Surgical Hubs" filed Mar. 29, 2018, U.S. Pat. Pub. No. 2019/0201140 entitled "Surgical Hub Situational Awareness" filed Mar. 29, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0206555 entitled "Cloud-based Medical Analytics For Customization And Recommendations To A User" filed Mar. 29, 2018, and U.S. Pat. Pub. No. 2019/0207857 entitled "Surgical Network Determination Of Prioritization Of Communication, Interaction, Or Processing Based On System Or Device Needs" filed Nov. 6, 2018, which are hereby incorporated by reference in their entireties.

Figure 18:
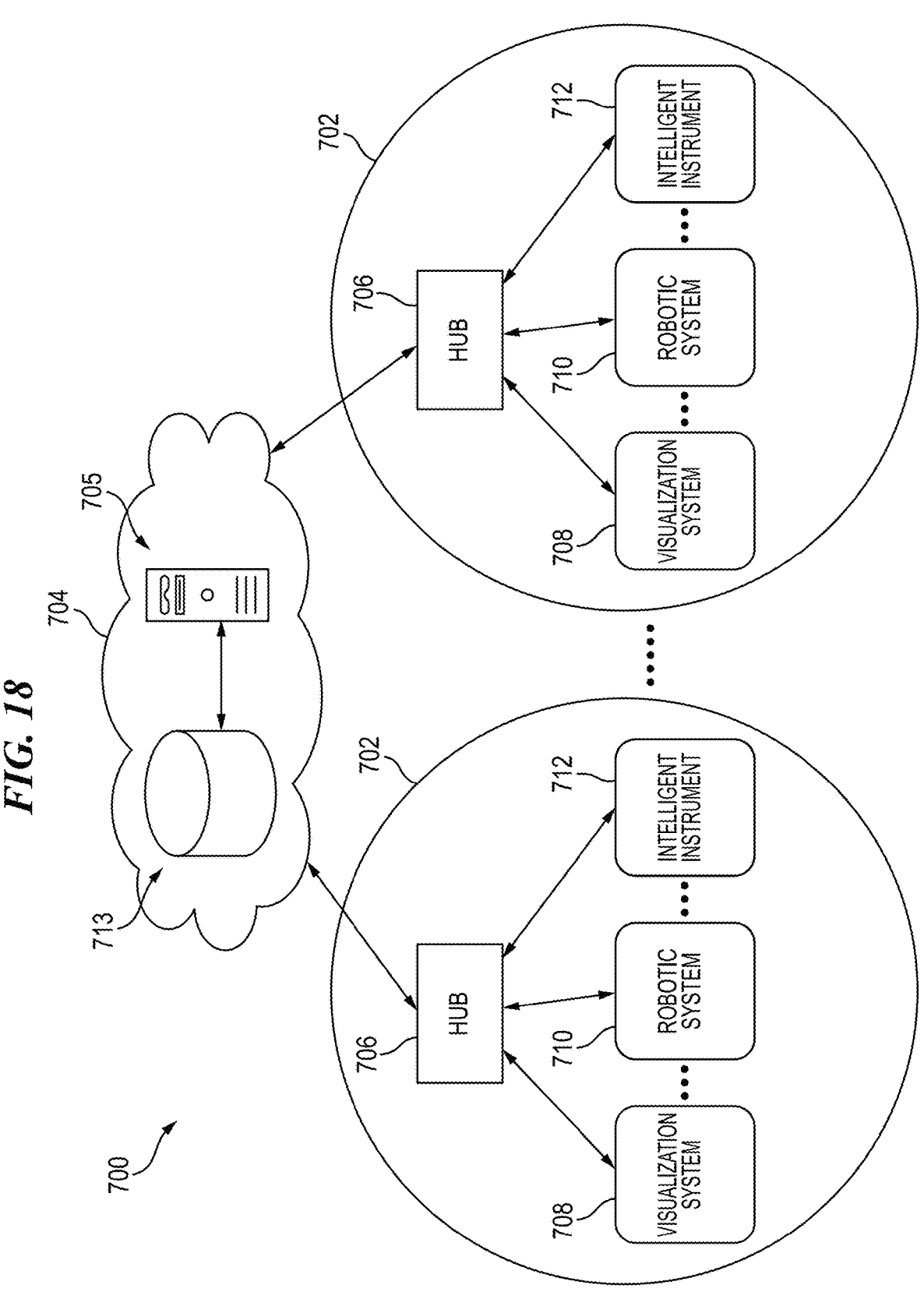
FIG. 18 is a schematic view of one embodiment of a computer-implemented interactive surgical system.

FIG. 18 illustrates one embodiment of a computer-implemented interactive surgical system 700 that includes one or more surgical systems 702 and a cloud-based system (e.g., a cloud 704 that can include a remote server 713 coupled to a storage device 705). Each surgical system 702 includes at least one surgical hub 706 in communication with the cloud 704. In one example, as illustrated in FIG. 18, the surgical system 702 includes a visualization system 708, a robotic system 710, and an intelligent (or "smart") surgical instrument 712, which are configured to communicate with one another and/or the hub 706. The intelligent surgical instrument 712 can include imaging device(s). The surgical system 702 can include an M number of hubs 706, an N number of visualization systems 708, an O number of robotic systems 710, and a P number of intelligent surgical instruments 712, where M, N, O, and P are integers greater than or equal to one that may or may not be equal to any one or more of each other. Various exemplary intelligent surgical instruments and robotic systems are described herein.

Data received by a surgical hub from a surgical visualization system can be used in any of a variety of ways. In an exemplary embodiment, the surgical hub can receive data from a surgical visualization system in use with a patient in a surgical setting, e.g., in use in an operating room during performance of a surgical procedure. The surgical hub can use the received data in any one or more ways, as discussed herein.

The surgical hub can be configured to analyze received data in real time with use of the surgical visualization system and adjust control one or more of the surgical visualization system and/or one or more intelligent surgical instruments in use with the patient based on the analysis of the received data. Such adjustment can include, for example, adjusting one or operational control parameters of intelligent surgical instrument(s), causing one or more sensors of one or more intelligent surgical instruments to take a measurement to help gain an understanding of the patient's current physiological condition, and/or current operational status of an intelligent surgical instrument, and other adjustments. Controlling and adjusting operation of intelligent surgical instruments is discussed further below. Examples of operational control parameters of an intelligent surgical instrument include motor speed, cutting element speed, time, duration, level of energy application, and light emission. Examples of surgical hubs and of controlling and adjusting intelligent surgical instrument operation are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019, and in U.S. patent application Ser. No. 17/068,857 entitled "Adaptive Responses From Smart Packaging Of Drug Delivery Absorbable Adjuncts" filed Oct. 13, 2020, U.S. patent application Ser. No. 17/068,858 entitled "Drug Administration Devices That Communicate With Surgical Hubs" filed Oct. 13, 2020, U.S. patent application Ser. No. 17/068,859 entitled "Controlling Operation Of Drug Administration Devices Using Surgical Hubs" filed Oct. 13, 2020, U.S. patent application Ser. No. 17/068,863 entitled "Patient Monitoring Using Drug Administration Devices" filed Oct. 13, 2020, U.S. patent application Ser. No. 17/068,865 entitled "Monitoring And Communicating Information Using Drug Administration Devices" filed Oct. 13, 2020, and U.S. patent application Ser. No. 17/068,867 entitled "Aggregating And Analyzing Drug Administration Data" filed Oct. 13, 2020, which are hereby incorporated by reference in their entireties.

The surgical hub can be configured to cause visualization of the received data to be provided in the surgical setting on a display so that a medical practitioner in the surgical setting can view the data and thereby receive an understanding of the operation of the imaging device(s) in use in the surgical setting. Such information provided via visualization can include text and/or images.

Figure 19:
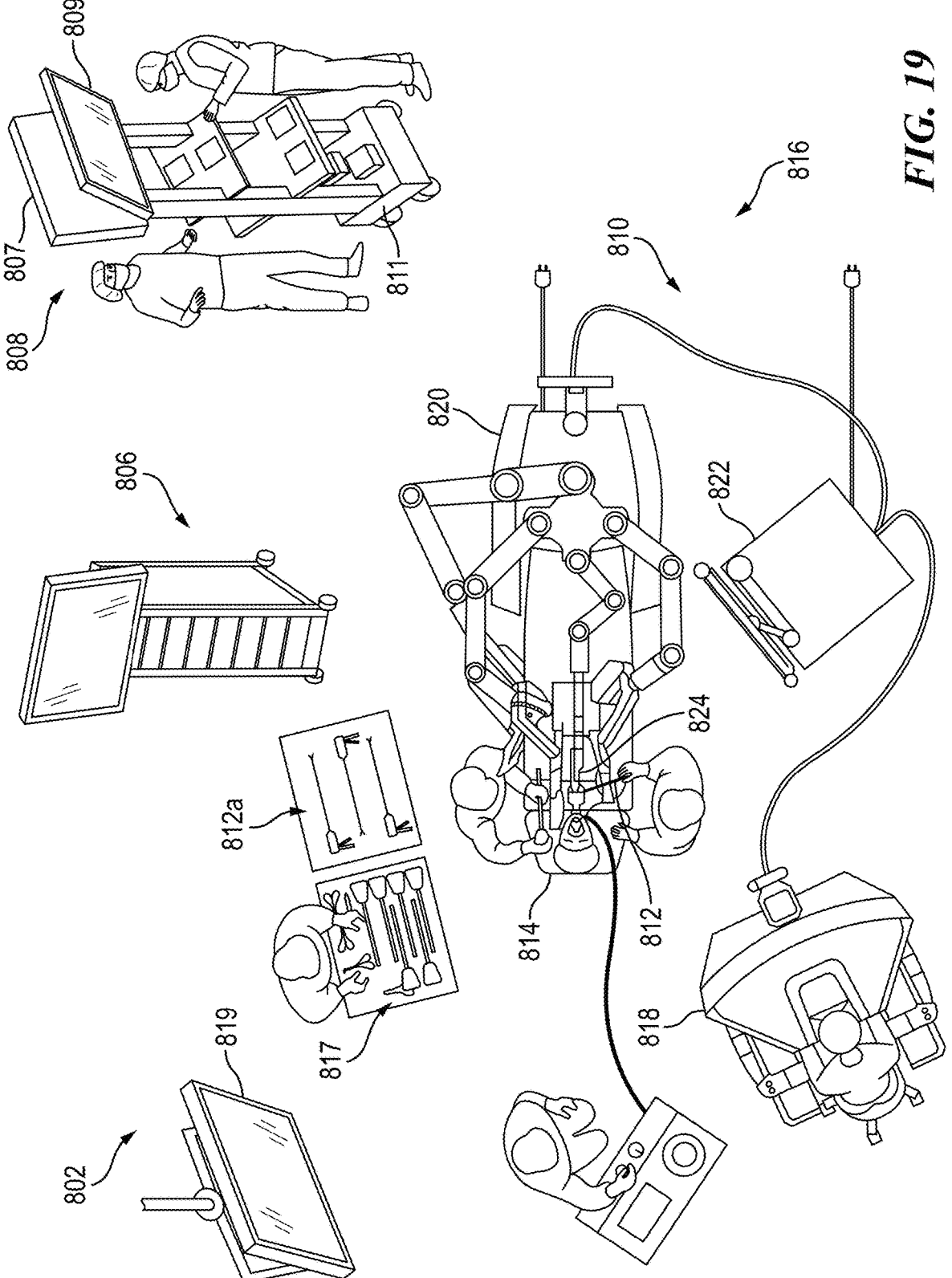
FIG. 19 is a schematic view of one embodiment a surgical system being used to perform a surgical procedure in an operating room.

FIG. 19 illustrates one embodiment of a surgical system 802 including a surgical hub 806 (e.g., the surgical hub 706 of FIG. 18 or other surgical hub described herein), a robotic surgical system 810 (e.g., the robotic surgical system 110 of FIG. 1 or other robotic surgical system herein), and a visualization system 808 (e.g., the visualization system 100 of FIG. 1 or other visualization system described herein). The surgical hub 806 can be in communication with a cloud, as discussed herein. FIG. 19 shows the surgical system 802 being used to perform a surgical procedure on a patient who is lying down on an operating table 814 in a surgical operating room 816. The robotic system 810 includes a surgeon's console 818, a patient side cart 820 (surgical robot), and a robotic system surgical hub 822. The robotic system surgical hub 822 is generally configured similar to the surgical hub 822 and can be in communication with a cloud. In some embodiments, the robotic system surgical hub 822 and the surgical hub 806 can be combined. The patient side cart 820 can manipulate an intelligent surgical tool 812 through a minimally invasive incision in the body of the patient while a medical practitioner, e.g., a surgeon, nurse, and/or other medical practitioner, views the surgical site through the surgeon's console 818. An image of the surgical site can be obtained by an imaging device 824 (e.g., the imaging device 120 of FIG. 1 or other imaging device described herein), which can be manipulated by the patient side cart 820 to orient the imaging device 824. The robotic system surgical hub 822 can be used to process the images of the surgical site for subsequent display to the surgeon through the surgeon's console 818.

A primary display 819 is positioned in the sterile field of the operating room 816 and is configured to be visible to an operator at the operating table 814. In addition, as in this illustrated embodiment, a visualization tower 811 can positioned outside the sterile field. The visualization tower 811 includes a first non-sterile display 807 and a second non-sterile display 809, which face away from each other. The visualization system 808, guided by the surgical hub 806, is configured to utilize the displays 807, 809, 819 to coordinate information flow to medical practitioners inside and outside the sterile field. For example, the surgical hub 806 can cause the visualization system 808 to display a snapshot and/or a video of a surgical site, as obtained by the imaging device 824, on one or both of the non-sterile displays 807, 809, while maintaining a live feed of the surgical site on the primary display 819. The snapshot and/or video on the non-sterile display 807 and/or 809 can permit a non-sterile medical practitioner to perform a diagnostic step relevant to the surgical procedure, for example.

The surgical hub 806 is configured to route a diagnostic input or feedback entered by a non-sterile medical practitioner at the visualization tower 811 to the primary display 819 within the sterile field, where it can be viewed by a sterile medical practitioner at the operating table 814. For example, the input can be in the form of a modification to the snapshot and/or video displayed on the non-sterile display 807 and/or 809, which can be routed to the primary display 819 by the surgical hub 806.

The surgical hub 806 is configured to coordinate information flow to a display of the intelligent surgical instrument 812, as is described in various U.S. patent applications that are incorporated by reference herein in the present disclosure. A diagnostic input or feedback entered by a non-sterile operator at the visualization tower 811 can be routed by the surgical hub 806 to the display 819 within the sterile field, where it can be viewed by the operator of the surgical instrument 812 and/or by other medical practitioner(s) in the sterile field.

The intelligent surgical instrument 812 and the imaging device 824, which is also an intelligent surgical tool, is being used with the patient in the surgical procedure as part of the surgical system 802. Other intelligent surgical instruments 812*a* that can be used in the surgical procedure, e.g., that can be removably coupled to the patient side cart 820 and be in communication with the robotic surgical system 810 and the surgical hub 806, are also shown in FIG. 19 as being available. Non-intelligent (or "dumb") surgical instruments 817, e.g., scissors, trocars, cannulas, scalpels, etc., that cannot be in communication with the robotic surgical system 810 and the surgical hub 806 are also shown in FIG. 19 as being available for use.

Operating Intelligent Surgical Instruments

An intelligent surgical device can have an algorithm stored thereon, e.g., in a memory thereof, configured to be executable on board the intelligent surgical device, e.g., by a processor thereof, to control operation of the intelligent surgical device. In some embodiments, instead of or in addition to being stored on the intelligent surgical device, the algorithm can be stored on a surgical hub, e.g., in a memory thereof, that is configured to communicate with the intelligent surgical device.

The algorithm is stored in the form of one or more sets of pluralities of data points defining and/or representing instructions, notifications, signals, etc. to control functions of the intelligent surgical device. In some embodiments, data gathered by the intelligent surgical device can be used by the intelligent surgical device, e.g., by a processor of the intelligent surgical device, to change at least one variable parameter of the algorithm. As discussed above, a surgical hub can be in communication with an intelligent surgical device, so data gathered by the intelligent surgical device can be communicated to the surgical hub and/or data gathered by another device in communication with the surgical hub can be communicated to the surgical hub, and data can be communicated from the surgical hub to the intelligent surgical device. Thus, instead of or in addition to the intelligent surgical device being configured to change a stored variable parameter, the surgical hub can be configured to communicate the changed at least one variable, alone or as part of the algorithm, to the intelligent surgical device and/or the surgical hub can communicate an instruction to the intelligent surgical device to change the at least one variable as determined by the surgical hub.

The at least one variable parameter is among the algorithm's data points, e.g., are included in instructions for operating the intelligent surgical device, and are thus each able to be changed by changing one or more of the stored pluralities of data points of the algorithm. After the at least one variable parameter has been changed, subsequent execution of the algorithm is according to the changed algorithm. As such, operation of the intelligent surgical device over time can be managed for a patient to increase the beneficial results use of the intelligent surgical device by taking into consideration actual situations of the patient and actual conditions and/or results of the surgical procedure in which the intelligent surgical device is being used. Changing the at least one variable parameter is automated to improve patient outcomes. Thus, the intelligent surgical device can be configured to provide personalized medicine based on the patient and the patient's surrounding conditions to provide a smart system. In a surgical setting in which the intelligent surgical device is being used during performance of a surgical procedure, automated changing of the at least one variable parameter may allow for the intelligent surgical device to be controlled based on data gathered during the performance of the surgical procedure, which may help ensure that the intelligent surgical device is used efficiently and correctly and/or may help reduce chances of patient harm by harming a critical anatomical structure.

The at least one variable parameter can be any of a variety of different operational parameters. Examples of variable parameters include motor speed, motor torque, energy level, energy application duration, tissue compression rate, jaw closure rate, cutting element speed, load threshold, etc.

Figure 20:
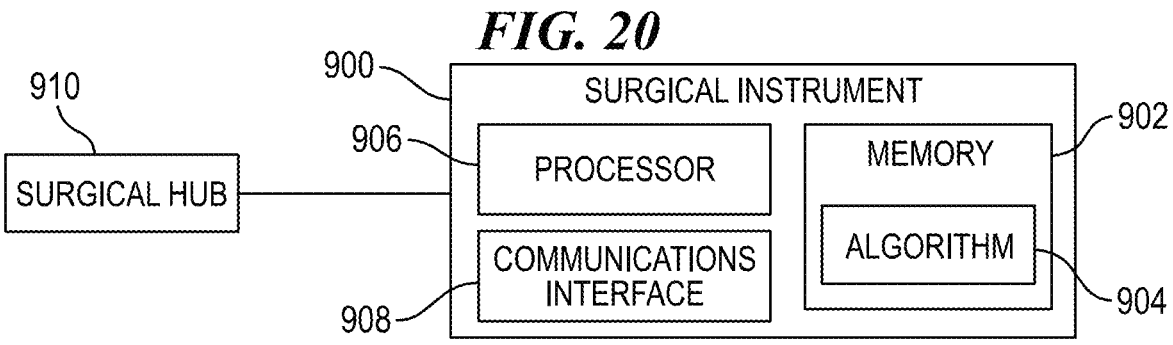
FIG. 20 is a schematic view of one embodiment of a surgical system including a smart surgical instrument and a surgical hub.

FIG. 20 illustrates one embodiment of an intelligent surgical instrument 900 including a memory 902 having an algorithm 904 stored therein that includes at least one variable parameter. The algorithm 904 can be a single algorithm or can include a plurality of algorithms, e.g., separate algorithms for different aspects of the surgical instrument's operation, where each algorithm includes at least one variable parameter. The intelligent surgical instrument 900 can be the surgical device 102 of FIG. 1, the imaging device 120 of FIG. 1, the surgical device 202 of FIG. 8, the imaging device 220 of FIG. 8, the surgical device 402 of FIG. 15, the surgical device 502*a* of FIG. 17, the surgical device 502*b* of FIG. 17, the surgical device 712 of FIG. 18, the surgical device 812 of FIG. 19, the imaging device 824 of FIG. 19, or other intelligent surgical instrument. The surgical instrument 900 also includes a processor 906 configured to execute the algorithm 904 to control operation of at least one aspect of the surgical instrument 900. To execute the algorithm 904, the processor 906 is configured to run a program stored in the memory 902 to access a plurality of data points of the algorithm 904 in the memory 902.

The surgical instrument 900 also includes a communications interface 908, e.g., a wireless transceiver or other wired or wireless communications interface, configured to communicate with another device, such as a surgical hub 910. The communications interface 908 can be configured to allow one-way communication, such as providing data to a remote server (e.g., a cloud server or other server) and/or to a local, surgical hub server, and/or receiving instructions or commands from a remote server and/or a local, surgical hub server, or two-way communication, such as providing information, messages, data, etc. regarding the surgical instrument 900 and/or data stored thereon and receiving instructions, such as from a doctor; a remote server regarding updates to software; a local, surgical hub server regarding updates to software; etc.

The surgical instrument 900 is simplified in FIG. 20 and can include additional components, e.g., a bus system, a handle, a elongate shaft having an end effector at a distal end thereof, a power source, etc. The processor 906 can also be configured to execute instructions stored in the memory 902 to control the device 900 generally, including other electrical components thereof such as the communications interface 908, an audio speaker, a user interface, etc.

The processor 906 is configured to change at least one variable parameter of the algorithm 904 such that a subsequent execution of the algorithm 904 will be in accordance with the changed at least one variable parameter. To change the at least one variable parameter of the algorithm 904, the processor 906 is configured to modify or update the data point(s) of the at least one variable parameter in the memory 902. The processor 906 can be configured to change the at least one variable parameter of the algorithm 904 in real time with use of the surgical device 900 during performance of a surgical procedure, which may accommodate real time conditions.

Additionally or alternatively to the processor 906 changing the at least one variable parameter, the processor 906 can be configured to change the algorithm 904 and/or at least one variable parameter of the algorithm 904 in response to an instruction received from the surgical hub 910. In some embodiments, the processor 906 is configured to change the at least one variable parameter only after communicating with the surgical hub 910 and receiving an instruction therefrom, which may help ensure coordinated action of the surgical instrument 900 with other aspects of the surgical procedure in which the surgical instrument 900 is being used.

In an exemplary embodiment, the processor 906 executes the algorithm 904 to control operation of the surgical instrument 900, changes the at least one variable parameter of the algorithm 904 based on real time data, and executes the algorithm 904 after changing the at least one variable parameter to control operation of the surgical instrument 900.

Figure 21:
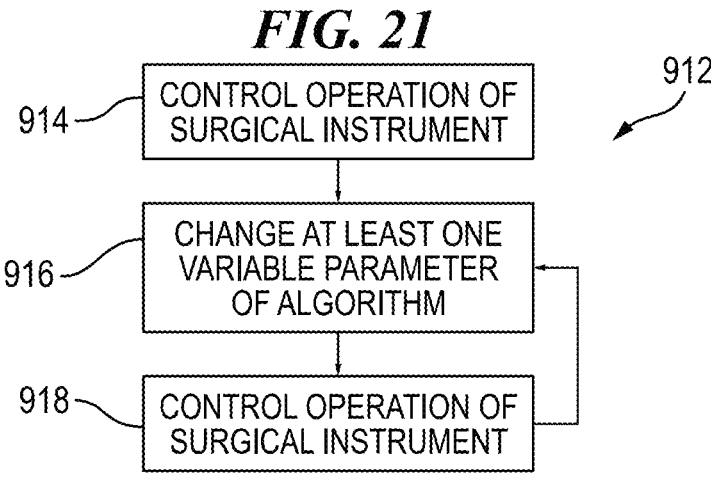
FIG. 21 is a flowchart showing a method of controlling the smart surgical instrument of FIG. 20.

FIG. 21 illustrates one embodiment of a method 912 of using of the surgical instrument 900 including a change of at least one variable parameter of the algorithm 904. The processor 906 controls 914 operation of the surgical instrument 900 by executing the algorithm 904 stored in the memory 902. Based on any of this subsequently known data and/or subsequently gathered data, the processor 904 changes 916 the at least one variable parameter of the algorithm 904 as discussed above. After changing the at least one variable parameter, the processor 906 controls 918 operation of the surgical instrument 900 by executing the algorithm 904, now with the changed at least one variable parameter. The processor 904 can change 916 the at least one variable parameter any number of times during performance of a surgical procedure, e.g., zero, one, two, three, etc. During any part of the method 912, the surgical instrument 900 can communicate with one or more computer systems, e.g., the surgical hub 910, a remote server such as a cloud server, etc., using the communications interface 908 to provide data thereto and/or receive instructions therefrom.

Situational Awareness

Operation of an intelligent surgical instrument can be altered based on situational awareness of the patient. The operation of the intelligent surgical instrument can be altered manually, such as by a user of the intelligent surgical instrument handling the instrument differently, providing a different input to the instrument, ceasing use of the instrument, etc. Additionally or alternatively, the operation of an intelligent surgical instrument can be changed automatically by an algorithm of the instrument being changed, e.g., by changing at least one variable parameter of the algorithm. As mentioned above, the algorithm can be adjusted automatically without user input requesting the change. Automating the adjustment during performance of a surgical procedure may help save time, may allow medical practitioners to focus on other aspects of the surgical procedure, and/or may ease the process of using the surgical instrument for a medical practitioner, which each may improve patient outcomes, such as by avoiding a critical structure, controlling the surgical instrument with consideration of a tissue type the instrument is being used on and/or near, etc.

The visualization systems described herein can be utilized as part of a situational awareness system that can be embodied or executed by a surgical hub, e.g., the surgical hub 706, the surgical hub 806, or other surgical hub described herein.

In particular, characterizing, identifying, and/or visualizing surgical instruments (including their positions, orientations, and actions), tissues, structures, users, and/or other things located within the surgical field or the operating theater can provide contextual data that can be utilized by a situational awareness system to infer various information, such as a type of surgical procedure or a step thereof being performed, a type of tissue(s) and/or structure(s) being manipulated by a surgeon or other medical practitioner, and other information. The contextual data can then be utilized by the situational awareness system to provide alerts to a user, suggest subsequent steps or actions for the user to undertake, prepare surgical devices in anticipation for their use (e.g., activate an electrosurgical generator in anticipation of an electrosurgical instrument being utilized in a subsequent step of the surgical procedure, etc.), control operation of intelligent surgical instruments (e.g., customize surgical instrument operational parameters of an algorithm as discussed further below), and so on.

Although an intelligent surgical device including an algorithm that responds to sensed data, e.g., by having at least one variable parameter of the algorithm changed, can be an improvement over a "dumb" device that operates without accounting for sensed data, some sensed data can be incomplete or inconclusive when considered in isolation, e.g., without the context of the type of surgical procedure being performed or the type of tissue that is being operated on. Without knowing the procedural context (e.g., knowing the type of tissue being operated on or the type of procedure being performed), the algorithm may control the surgical device incorrectly or sub-optimally given the particular context-free sensed data. For example, the optimal manner for an algorithm to control a surgical instrument in response to a particular sensed parameter can vary according to the particular tissue type being operated on. This is due to the fact that different tissue types have different properties (e.g., resistance to tearing, ease of being cut, etc.) and thus respond differently to actions taken by surgical instruments. Therefore, it may be desirable for a surgical instrument to take different actions even when the same measurement for a particular parameter is sensed. As one example, the optimal manner in which to control a surgical stapler in response to the surgical stapler sensing an unexpectedly high force to close its end effector will vary depending upon whether the tissue type is susceptible or resistant to tearing. For tissues that are susceptible to tearing, such as lung tissue, the surgical instrument's control algorithm would optimally ramp down the motor in response to an unexpectedly high force to close to avoid tearing the tissue, e.g., change a variable parameter controlling motor speed or torque so the motor is slower. For tissues that are resistant to tearing, such as stomach tissue, the instrument's algorithm would optimally ramp up the motor in response to an unexpectedly high force to close to ensure that the end effector is clamped properly on the tissue, e.g., change a variable parameter controlling motor speed or torque so the motor is faster. Without knowing whether lung or stomach tissue has been clamped, the algorithm may be sub-optimally changed or not changed at all.

A surgical hub can be configured to derive information about a surgical procedure being performed based on data received from various data sources and then control modular devices accordingly. In other words, the surgical hub can be configured to infer information about the surgical procedure from received data and then control the modular devices operably coupled to the surgical hub based upon the inferred context of the surgical procedure. Modular devices can include any surgical device that is controllable by a situational awareness system, such as visualization system devices (e.g., a camera, a display screen, etc.), smart surgical instruments (e.g., an ultrasonic surgical instrument, an electrosurgical instrument, a surgical stapler, smoke evacuators, scopes, etc.). A modular device can include sensor(s) configured to detect parameters associated with a patient with which the device is being used and/or associated with the modular device itself.

The contextual information derived or inferred from the received data can include, for example, a type of surgical procedure being performed, a particular step of the surgical procedure that the surgeon (or other medical practitioner) is performing, a type of tissue being operated on, or a body cavity that is the subject of the surgical procedure. The situational awareness system of the surgical hub can be configured to derive the contextual information from the data received from the data sources in a variety of different ways. In an exemplary embodiment, the contextual information received by the situational awareness system of the surgical hub is associated with a particular control adjustment or set of control adjustments for one or more modular devices. The control adjustments each correspond to a variable parameter. In one example, the situational awareness system includes a pattern recognition system, or machine learning system (e.g., an artificial neural network), that has been trained on training data to correlate various inputs (e.g., data from databases, patient monitoring devices, and/or modular devices) to corresponding contextual information regarding a surgical procedure. In other words, a machine learning system can be trained to accurately derive contextual information regarding a surgical procedure from the provided inputs. In another example, the situational awareness system can include a lookup table storing precharacterized contextual information regarding a surgical procedure in association with one or more inputs (or ranges of inputs) corresponding to the contextual information. In response to a query with one or more inputs, the lookup table can return the corresponding contextual information for the situational awareness system for controlling at least one modular device. In another example, the situational awareness system includes a further machine learning system, lookup table, or other such system, which generates or retrieves one or more control adjustments for one or more modular devices when provided the contextual information as input.

A surgical hub including a situational awareness system may provide any number of benefits for a surgical system. One benefit includes improving the interpretation of sensed and collected data, which would in turn improve the processing accuracy and/or the usage of the data during the course of a surgical procedure. Another benefit is that the situational awareness system for the surgical hub may improve surgical procedure outcomes by allowing for adjustment of surgical instruments (and other modular devices) for the particular context of each surgical procedure (such as adjusting to different tissue types) and validating actions during a surgical procedure. Yet another benefit is that the situational awareness system may improve surgeon's and/or other medical practitioners' efficiency in performing surgical procedures by automatically suggesting next steps, providing data, and adjusting displays and other modular devices in the surgical theater according to the specific context of the procedure. Another benefit includes proactively and automatically controlling modular devices according to the particular step of the surgical procedure that is being performed to reduce the number of times that medical practitioners are required to interact with or control the surgical system during the course of a surgical procedure, such as by a situationally aware surgical hub proactively activating a generator to which an RF electrosurgical instrument is connected if it determines that a subsequent step of the procedure requires the use of the instrument. Proactively activating the energy source allows the instrument to be ready for use a soon as the preceding step of the procedure is completed.

For example, a situationally aware surgical hub can be configured to determine what type of tissue is being operated on. Therefore, when an unexpectedly high force to close a surgical instrument's end effector is detected, the situationally aware surgical hub can be configured to correctly ramp up or ramp down a motor of the surgical instrument for the type of tissue, e.g., by changing or causing change of at least one variable parameter of an algorithm for the surgical instrument regarding motor speed or torque.

For another example, a type of tissue being operated can affect adjustments that are made to compression rate and load thresholds of a surgical stapler for a particular tissue gap measurement. A situationally aware surgical hub can be configured to infer whether a surgical procedure being performed is a thoracic or an abdominal procedure, allowing the surgical hub to determine whether the tissue clamped by an end effector of the surgical stapler is lung tissue (for a thoracic procedure) or stomach tissue (for an abdominal procedure). The surgical hub can then be configured to cause adjustment of the compression rate and load thresholds of the surgical stapler appropriately for the type of tissue, e.g., by changing or causing change of at least one variable parameter of an algorithm for the surgical stapler regarding compression rate and load threshold.

As yet another example, a type of body cavity being operated in during an insufflation procedure can affect the function of a smoke evacuator. A situationally aware surgical hub can be configured to determine whether the surgical site is under pressure (by determining that the surgical procedure is utilizing insufflation) and determine the procedure type. As a procedure type is generally performed in a specific body cavity, the surgical hub can be configured to control a motor rate of the smoke evacuator appropriately for the body cavity being operated in, e.g., by changing or causing change of at least one variable parameter of an algorithm for the smoke evacuator regarding motor rate. Thus, a situationally aware surgical hub may provide a consistent amount of smoke evacuation for both thoracic and abdominal procedures.

As yet another example, a type of procedure being performed can affect the optimal energy level for an ultrasonic surgical instrument or radio frequency (RF) electrosurgical instrument to operate at. Arthroscopic procedures, for example, require higher energy levels because an end effector of the ultrasonic surgical instrument or RF electrosurgical instrument is immersed in fluid. A situationally aware surgical hub can be configured to determine whether the surgical procedure is an arthroscopic procedure. The surgical hub can be configured to adjust an RF power level or an ultrasonic amplitude of the generator (e.g., adjust energy level) to compensate for the fluid filled environment, e.g., by changing or causing change of at least one variable parameter of an algorithm for the instrument and/or a generator regarding energy level. Relatedly, a type of tissue being operated on can affect the optimal energy level for an ultrasonic surgical instrument or RF electrosurgical instrument to operate at. A situationally aware surgical hub can be configured to determine what type of surgical procedure is being performed and then customize the energy level for the ultrasonic surgical instrument or RF electrosurgical instrument, respectively, according to the expected tissue profile for the surgical procedure, e.g., by changing or causing change of at least one variable parameter of an algorithm for the instrument and/or a generator regarding energy level. Furthermore, a situationally aware surgical hub can be configured to adjust the energy level for the ultrasonic surgical instrument or RF electrosurgical instrument throughout the course of a surgical procedure, rather than just on a procedure-by-procedure basis. A situationally aware surgical hub can be configured to determine what step of the surgical procedure is being performed or will subsequently be performed and then update the control algorithm(s) for the generator and/or ultrasonic surgical instrument or RF electrosurgical instrument to set the energy level at a value appropriate for the expected tissue type according to the surgical procedure step.

As another example, a situationally aware surgical hub can be configured to determine whether the current or subsequent step of a surgical procedure requires a different view or degree of magnification on a display according to feature(s) at the surgical site that the surgeon and/or other medical practitioner is expected to need to view. The surgical hub can be configured to proactively change the displayed view (supplied by, e.g., an imaging device for a visualization system) accordingly so that the display automatically adjusts throughout the surgical procedure.

As yet another example, a situationally aware surgical hub can be configured to determine which step of a surgical procedure is being performed or will subsequently be performed and whether particular data or comparisons between data will be required for that step of the surgical procedure. The surgical hub can be configured to automatically call up data screens based upon the step of the surgical procedure being performed, without waiting for the surgeon or other medical practitioner to ask for the particular information.

As another example, a situationally aware surgical hub can be configured to determine whether a surgeon and/or other medical practitioner is making an error or otherwise deviating from an expected course of action during the course of a surgical procedure, e.g., as provided in a pre-operative surgical plan. For example, the surgical hub can be configured to determine a type of surgical procedure being performed, retrieve a corresponding list of steps or order of equipment usage (e.g., from a memory), and then compare the steps being performed or the equipment being used during the course of the surgical procedure to the expected steps or equipment for the type of surgical procedure that the surgical hub determined is being performed. The surgical hub can be configured to provide an alert (visual, audible, and/or tactile) indicating that an unexpected action is being performed or an unexpected device is being utilized at the particular step in the surgical procedure.

In certain instances, operation of a robotic surgical system, such as any of the various robotic surgical systems described herein, can be controlled by the surgical hub based on its situational awareness and/or feedback from the components thereof and/or based on information from a cloud (e.g., the cloud 713 of FIG. 18).

Embodiments of situational awareness systems and using situational awareness systems during performance of a surgical procedure are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019.

Surgical Procedures of the Lung

Various aspects of the devices, systems, and methods described herein may relate to a surgical procedure performed on a lung. For example, a lung resection, e.g., a lobectomy, is a surgical procedure in which all or part, e.g., one or more lobes, of a lung is removed. The purpose of performing a lung resection is to treat a damaged or diseased lung as a result of, for example, lung cancer, emphysema, or bronchiectasis.

During a lung resection, the lung or lungs are first deflated, and thereafter one or more incisions are made on the patient's side between the patient's ribs to reach the lungs laparoscopically. Surgical instruments, such as graspers and a laparoscope, are inserted through the incision. Once the infected or damaged area of the lung is identified, the area is dissected from the lung and removed from the one or more incisions. The dissected area and the one or more incisions can be closed, for example, with a surgical stapler or stitches.

Since the lung is deflated during surgery, the lung, or certain portions thereof, may need to be mobilized to allow the surgical instruments to reach the surgical site. This mobilization can be carried out by grasping the outer tissue layer of the lung with graspers and applying a force to the lung through the graspers. However, the pleura and parenchyma of the lung are very fragile and therefore can be easily ripped or torn under the applied force. Additionally, during mobilization, the graspers can cut off blood supply to one or more areas of the lung.

Further, a breathing tube is placed into the patient's airway to allow each lung to be separately inflated during surgery. Inflation of the lung can cause the lung to move and match pre-operative imaging and/or allow the surgeon to check for leaks at the dissected area(s). However, by inflating the whole lung, working space is lost around the lung due to the filling of the thoracic cavity. Additionally, inflating a whole lung can take time and does not guarantee easy leak detection if multiple portions of the lung are operated on during the surgical procedure.

Surgical Procedures of the Colon

Figure 22:
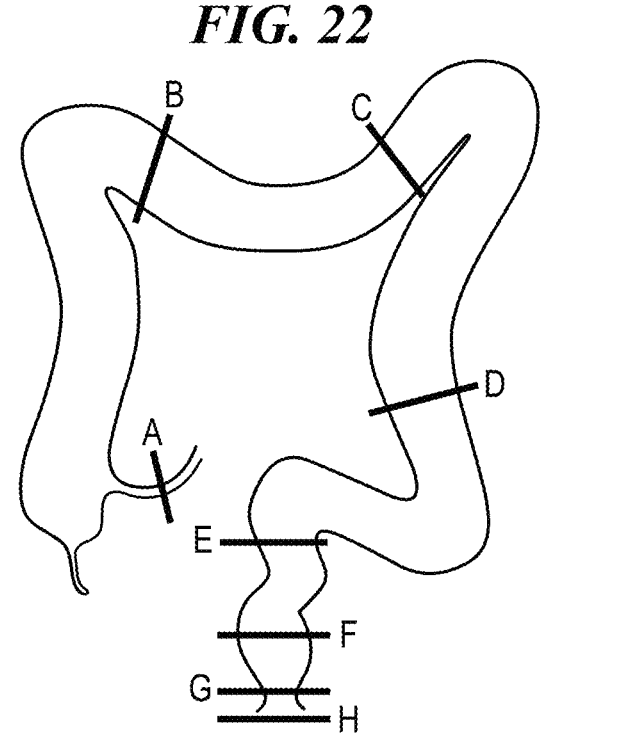
FIG. 22 is a schematic view of a colon illustrating major resections of the colon.

Various aspects of the devices, systems, and methods described herein may relate to a surgical procedure performed on a colon. For example, surgery is often the main treatment for early-stage colon cancers. The type of surgery used depends on the stage (extent) of the cancer, where it is in the colon, and the goal of the surgery. Some early colon cancers (stage 0 and some early stage I tumors) and most polyps can be removed during a colonoscopy. However, if the cancer has progressed, a local excision or colectomy may be required. A colectomy is surgery to remove all or part of the colon. In certain instances, nearby lymph nodes are also removed. If only part of the colon is removed, it's called a hemicolectomy, partial colectomy, or segmental resection in which the surgeon takes out the diseased part of the colon with a small segment of non-diseased colon on either side. Usually, about one-fourth to one-third of the colon is removed, depending on the size and location of the cancer. Major resections of the colon are illustrated in FIG. 22, in which A-B is a right hemicolectomy, A-C is an extended right hemicolectomy, B-C is a transverse colectomy, C-E is a left hemicolectomy, D-E is a sigmoid colectomy, D-F is an anterior resection, D-G is a (ultra) low anterior resection, D-H is an abdomino-perineal resection, A-D is a subtotal colectomy, A-E is a total colectomy, and A-H is a total procto-colectomy. Once the resection is complete, the remaining intact sections of colon are then reattached.

A colectomy can be performed through an open colectomy, where a single incision through the abdominal wall is used to access the colon for separation and removal of the affected colon tissue, and through a laparoscopic-assisted colectomy. With a laparoscopic-assisted colectomy, the surgery is done through many smaller incisions with surgical instruments and a laparoscope passing through the small incisions to remove the entire colon or a part thereof. At the beginning of the procedure, the abdomen is inflated with gas, e.g., carbon dioxide, to provide a working space for the surgeon. The laparoscope transmits images inside the abdominal cavity, giving the surgeon a magnified view of the patient's internal organs on a monitor or other display. Several other cannulas are inserted to allow the surgeon to work inside and remove part(s) of the colon. Once the diseased parts of the colon are removed, the remaining ends of the colon are attached to each other, e.g., via staplers or stitches. The entire procedure may be completed through the cannulas or by lengthening one of the small cannula incisions.

During a laparoscopic-assisted colectomy procedure, it is often difficult to obtain an adequate operative field. Oftentimes, dissections are made deep in the pelvis which makes it difficult to obtain adequate visualization of the area. As a result, the lower rectum must be lifted and rotated to gain access to the veins and arteries around both sides of the rectum during mobilization. During manipulation of the lower rectum, bunching of tissue and/or overstretching of tissue can occur. Additionally, a tumor within the rectum can cause adhesions in the surrounding pelvis, and as a result, this can require freeing the rectal stump and mobilizing the mesentery and blood supply before transection and removal of the tumor.

Further, multiple graspers are needed to position the tumor for removal from the colon. During dissection of the colon, the tumor should be placed under tension, which requires grasping and stretching the surrounding healthy tissue of the colon. However, the manipulating of the tissue surrounding the tumor can suffer from reduced blood flow and trauma due to the graspers placing a high grip force on the tissue. Additionally, during a colectomy, the transverse colon and upper descending colon may need to be mobilized to allow the healthy, good remaining colon to be brought down to connect to the rectal stump after the section of the colon containing the tumor is transected and removed.

After a colectomy, the remaining healthy portions of the colon must be reattached to one another to create a path for waste to leave the body. However, when using laparoscopic instruments to perform the colectomy, one single entry port may not have a large enough range of motion to move the one end of the colon to a connecting portion of the colon. As such, a second entry port is therefore needed to laparoscopically insert surgical instruments to help mobilize the colon in order to properly position the colon.

Surgical Procedures of the Stomach

Various aspects of the devices, systems, and methods described herein may relate to a surgical procedure performed on a stomach. For example, surgery is the most common treatment for stomach cancer. When surgery is required for stomach cancer, the goal is to remove the entire tumor as well as a good margin of healthy stomach tissue around the tumor. Different procedures can be used to remove stomach cancer. The type of procedure used depends on what part of the stomach the cancer is located and how far it has grown into nearby areas. For example, endoscopic mucosal resection (EMR) and endoscopic submucosal dissection (ESD) are procedures on the stomach can be used to treat some early-stage cancers. These procedures do not require a cut in the skin, but instead the surgeon passes an endoscope down the throat and into the stomach of the patient. Surgical tools (e.g., MEGADYNE™ Tissue Dissector or Electrosurgical Pencils) are then passed through the working channel of the endoscope to remove the tumor and some layers of the normal stomach wall below and around it.

Other surgical procedures performed on a stomach include a subtotal (partial) or a total gastrectomy that can be performed as an open procedure. e.g., surgical instruments are inserted through a large incision in the skin of the abdomen, or as a laparoscopic procedure, e.g., surgical instruments are inserted into the abdomen through several small cuts. For example, a laparoscopic gastrectomy procedure generally involves insufflation of the abdominal cavity with carbon dioxide gas to a pressure of around 15 millimeters of mercury (mm Hg). The abdominal wall is pierced and a straight tubular cannula or trocar, such as a cannula or trocar having a diameter in a range of about 5 mm to about 10 mm, is then inserted into the abdominal cavity. A laparoscope connected to an operating room monitor is used to visualize the operative field and is placed through one of the trocar(s). Laparoscopic surgical instruments are placed through two or more additional cannulas or trocars for manipulation by medical practitioner(s), e.g., surgeon and surgical assistant(s), to remove the desired portion(s) of the stomach.

In certain instances, laparoscopic and endoscopic cooperative surgery can be used to remove gastric tumors. This cooperative surgery typically involves introduction of an endoscope, e.g., a gastroscope, and laparoscopic trocars. A laparoscope and tissue manipulation and dissection surgical instruments are introduced through the trocar. The tumor location can be identified via the endoscope and a cutting element that is inserted into the working channel of the endoscope is then used for submucosal resection around the tumor. A laparoscopic dissection surgical instrument is then used for seromuscular dissection adjacent the tumor margins to create an incision through the stomach wall. The tumor is then pivoted through this incision from the intraluminal space, e.g., inside the stomach, to the extraluminal space, e.g., outside of the stomach. A laparoscopic surgical instrument, e.g., an endocutter, can be used to then complete the transection of the tumor from the stomach wall and seal the incision.

Surgical Procedures of the Intestine

Various aspects of the devices, systems, and methods described herein may relate to a surgical procedure performed on an intestine. For example, a duodenal mucosal resurfacing (DMR) procedure can be performed endoscopically to treat insulin-resistant metabolic diseases such as type 2 diabetes. The DMR procedure can be an effective treatment because it affects detection of food. The DMR procedure inhibits duodenum function such that food tends to be sensed deeper in the intestine than normal, e.g., sensed after passage through the duodenum (which is the first part of the small intestine). The patient's body thus senses sugar deeper in the intestine than is typical and thus reacts to the sugar later than is typical such that glycemic control can be improved. The irregular function of the duodenum changes the body's typical response to the food and, through nervous system and chemical signals, causes the body to adapt its response to the glucose level to increase insulin levels.

In the DMR procedure, the duodenal mucosa is lifted, such as with saline, and then the mucosa is ablated, e.g., using an ablation device advanced into the duodenum through a working channel of an endoscope. Lifting the mucosa before ablation helps protect the duodenum's outer layers from being damaged by the ablation. After the mucosa is ablated, the mucosa later regenerates. Examples of ablation devices are NeuWave™ ablation probes (available from Ethicon US LLC of Cincinnati, OH). Another example of an ablation device is the Hyblate catheter ablation probe (available from Hyblate Medical of Misgav, Israel). Another example of an ablation device is the Barxx™ HaloFlex (available from Medtronic of Minneapolis, MN).

Figure 22A:
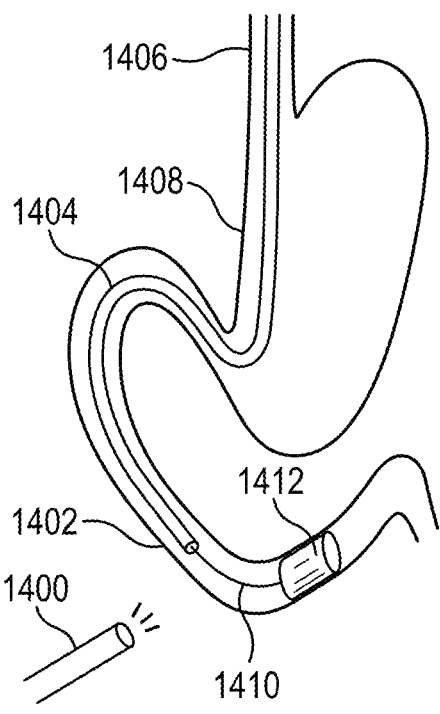
FIG. 22A is a perspective partial cross-sectional view of one embodiment of a duodenal mucosal resurfacing procedure.

FIG. 22A illustrates one embodiment of a DMR procedure. As shown in FIG. 22A, a laparoscope 1400 is positioned external to a duodenum 1402 for external visualization of the duodenum 1402. An endoscope 1404 is advanced transorally through an esophagus 1406, through a stomach 1408, and into the duodenum 1402 for internal visualization of the duodenum 1402. An ablation device 1410 is advanced through a working channel of the endoscope 1404 to extend distally from the endoscope 1404 into the duodenum 1402. A balloon 1412 of the ablation device 1410 is shown expanded or inflated in FIG. 22A. The expanded or inflated balloon 1412 can help center the ablation device's electrode so even circumferential ablating can occur before the ablation device 1410 is advanced and/or retracted to repeat ablation. Before the mucosa is ablated using the ablation device 1410, the duodenal mucosa is lifted, such as with saline. In some embodiments in addition to or instead of including the balloon 1412, the ablation device 1410 can be expandable/collapsible using an electrode array or basket configured to expand and collapse.

The laparoscope's external visualization of the duodenum 1402 can allow for thermal monitoring of the duodenum 1402, which may help ensure that the outer layers of the duodenum 1402 are not damaged by the ablation of the duodenal mucosa, such as by the duodenum being perforated. Various embodiments of thermal monitoring are discussed further, for example, below and in U.S. patent application Ser. No. 17/494,364 entitled "Surgical Methods For Control Of One Visualization With Another" filed on Oct. 5, 2021. The endoscope 1404 and/or the ablation device 1410 can include a fiducial marker thereon that the laparoscope 1400 can be configured to visualize through the duodenum's tissue, e.g., by using invisible light, to help determine where the laparoscope 1400 should externally visualize the duodenum 1402 at a location where ablation occurs. Various embodiments of fiducial markers are discussed further, for example, in U.S. patent application Ser. No. 17/493,913 entitled "Surgical Methods Using Fiducial Identification And Tracking" filed on Oct. 5, 2021 and in U.S. patent application Ser. No. 17/494,364 entitled "Surgical Methods For Control Of One Visualization With Another" filed on Oct. 5, 2021.

Cooperative Surgical Visualization

Devices, systems, and methods for multi-source imaging provided herein may allow for cooperative surgical visualization. In general, in cooperative surgical visualization, first and second imaging systems each gathering images of a surgical site are configured to cooperate to provide enhanced imaging of a surgical site. The first imaging system can be configured similar to the imaging system of FIG. 1 that includes the imaging device 120, the imaging system 142 of FIG. 4, the imaging system of FIG. 11, or other imaging system described herein, and the second imaging system can be configured similar to the imaging system of FIG. 1 that includes the imaging device 120, the imaging system 142 of FIG. 4, the imaging system of FIG. 11, or other imaging system described herein. The cooperative surgical visualization may improve visualization of patient anatomy at the surgical site and/or improve control of surgical instrument(s) at the surgical site.

Each of the first and second imaging systems is configured to gather images of the surgical site from a different point of view by the first and second imaging systems each viewing the surgical site from a different vantage point. The first imaging system can provide a primary visualization of the surgical site, while the second imaging system's visualization of the surgical site can provide a secondary visualization of the surgical site used to enhance the primary visualization as displayed on a display. A single display may thus provide two separate points of view of the surgical site, which may conveniently allow a medical practitioner to view only one display instead of multiple displays. The second imaging system viewing the same surgical site as the first imaging system but from a different perspective allows for the enhancement since a second view, as gathered by the second imaging system, may provide different information than the first imaging system. For example, the first imaging system can be visualizing the surgical site from a first side of a tissue wall at the surgical site, and the second imaging system can be visualizing the surgical site from a second, opposite side of the tissue wall. The display can show the surgical site as visualized by the first imaging system enhanced with images gathered by the second imaging system that the first imaging system cannot gather because the tissue walls blocks the first imaging system from such a view. For another example, the first imaging system can be visualizing the surgical site from inside a body lumen at the surgical site, and the second imaging system can be visualizing the surgical site from outside the body lumen. The display can show the surgical site as visualized by the first imaging system enhanced with images gathered by the second imaging system that the first imaging system cannot gather because a wall of the body lumen blocks the first imaging system from such a view. For yet another example, the first imaging system can be visualizing an organ or other anatomic structure at the surgical site from a first point of view, and the second imaging system can be visualizing the organ or other anatomic structure from a second, different point of view. The display can show the surgical site as visualized by the first imaging system enhanced with images gathered by the second imaging system that the first imaging system cannot gather because of the organ or other anatomic structure blocks the first imaging system from such a view.

Cooperative surgical visualization may allow a critical structure (e.g., the critical structure 101 of FIG. 1, the critical structure 401 of FIG. 15, the first critical structure 501*a* of FIG. 17, the second critical structure 501*b* of FIG. 17, or other critical structure described herein) to be visualized from two different points of view, e.g., from the two different points of view of the first and second imaging systems, and thus provide a medical practitioner with better, more accurate information about how to avoid the critical structure or how to access the critical structure as needed in the particular surgical procedure being performed. In some instances, only one of the first and second imaging systems may be able to see a critical structure (e.g., the critical structure 101 of FIG. 1, the critical structure 401 of FIG. 15, the first critical structure 501*a* of FIG. 17, the second critical structure 501*b* of FIG. 17, or other critical structure described herein) from its point of view, in which case the cooperative surgical visualization may allow the critical structure to be seen when it would otherwise not be visible if a medical practitioner was only viewing images gathered by the other imaging system.

The first and second imaging systems are each configured to be in communication with a surgical hub (e.g., the surgical hub 706 of FIG. 18, the robotic system surgical hub 822 of FIG. 19, or other surgical hub described herein) that can be configured to control the positioning and/or orientation of the second imaging system. The surgical hub can thus be configured to receive images gathered by each of the first and second imaging systems to facilitate the cooperative surgical visualization. In other embodiments, the first and second imaging systems can be each in communication with a robotic surgical system or other computer system to facilitate the cooperative surgical visualization.

In some embodiments, cooperative surgical visualization includes a first imaging system visualizing a surgical site and coupling a second imaging system with the first imaging system, where the second imaging is also visualizing the surgical site but from a different point of view than the first imaging system. The second imaging system may not have a clear view, or any view, of the critical structure. The first imaging system can be used to aid in the positioning and/or orientation of the second imaging system and thus help adjust the point of view the second imaging system has of the surgical site and thereby help improve visualization of the critical structure. Such adjustment can be particularly useful during a tissue interaction activity, such as when the tissue's configuration is being changed during performance of a surgical procedure.

For example, in a surgical procedure on a lung such as a lung resection, the lung needs to be collapsed (deflated) for effective performance of the surgical procedure. The lung being collapsed is an example of a tissue interaction activity. Once the lung is collapsed, the lung is in a different state than shown in any preoperative images and/or intraoperative images of the lung gathered before the lung was collapsed, such as from a CT or MRI scan. It may therefore be difficult for a medical practitioner to locate a tumor and/or other critical structure(s) with the lung collapsed based on the images in which the lung is not collapsed. Before the lung is deflated, the first and second imaging systems can each be visualizing the lung, with at least the second imaging system visualizing the tumor and/or other critical structure(s). Then, during the deflating of the lung, the visualization provided by the first imaging system can be used, e.g., by a surgical hub, a robotic surgical system, or other computer system, to adjust the position and/or orientation of the second imaging system to help the second imaging system maintain and/or provide visualization of the tumor and/or other critical structure(s). The tumor and/or other critical structure(s) may thus still be easily located with the lung collapsed because at least the second imaging system will be visualizing the tumor and/or other critical structure(s) due to its repositioning/reorientation during collapse of the lung.

For another example, a first imaging system, e.g., bronchoscope, can be introduced into a patient trans-bronchially in a surgical procedure on a lung. The first imaging system can thus provide visualization of the lung from a known trans-bronchial position. The visualization provided by the first imaging system from the known trans-bronchial position can be used, e.g., by a surgical hub, to adjust the position and/or orientation of the second imaging system to help the second imaging system maintain and/or provide visualization of the tumor and/or other critical structure(s).

In some embodiments, cooperative surgical visualization includes providing shared visualization on a display from a first imaging system visualizing a surgical site and a second imaging system also visualizing the surgical site but from a different point of view than the first imaging system. For example, some surgical procedures, such as some surgical procedures of the stomach, some surgical procedures of the lung, and some surgical procedures of the intestine, involve laparoscopic and endoscopic cooperative surgery in which a laparoscope and an endoscope are each used to visualize a surgical site. The laparoscope can be controlled by a first medical practitioner viewing images gathered by the laparoscope on a first display, and the endoscope can be controlled by a second medical practitioner viewing images gathered by the endoscope on a second, different display. The medical practitioner control can be manual control or control via a robotic surgical system. Images gathered by each of the first and second imaging systems, e.g., the laparoscope and the endoscope, can each be communicated to a surgical hub or other computer system, thereby allowing the surgical hub or other computer system to provide the images from each of the first and second imaging systems to each of the first and second displays. Each of the first and second medical practitioners may therefore be able to more accurately control their respective imaging systems since they can see the surgical site from multiple points of view on a single display despite each medical practitioner only controlling an imaging system with one point of view.

The images can be provided to each of the first and second displays while each of the first and second imaging systems are moving and thus not providing images from a static point of view. The first and second medical practitioners may thus be able to adjust position and/or orientation of their respective imaging systems based on what the other imaging system is seeing, e.g., to prevent views that are too similar. Alternatively, the images can be provided to each of the first and second displays once at least one of the first and second imaging systems has stopped moving and is thus providing images from a static point of view. The static point of view may facilitate combined imaging by allowing each of the first and second medical practitioners to control movement and positioning of their respective imaging systems based on the view therefrom during setup and a tissue interaction activity and, thereafter, based on views from both of the first and second imaging systems.

Instead of the first and second imaging systems being controlled by first and second medical practitioners, the first and second imaging systems can be controlled by one medical practitioner, either manually or via a robotic surgical system. In such instances, the display associated with the medical practitioner, e.g., the display that the medical practitioner is viewing whether the display be of a robotic surgical console or otherwise, can switch back and forth between showing images gathered by the first imaging system and images gathered by the second imaging system while each of the first and second imaging systems are moving. Then, once at least one of the first and second imaging systems has stopped moving, the display can provide combined imaging from the first and second imaging systems. The static point of view may facilitate combined imaging by allowing the medical practitioner to control movement and positioning of the moving one of the imaging system based on views from both of the first and second imaging systems.

In some embodiments, cooperative surgical visualization includes a first imaging system visualizing a first anatomic aspect at a surgical site and a second imaging system visualizing a second, different anatomic aspect at the surgical site where the first imaging system cannot visualize the second anatomic aspect and the second imaging system cannot visualize the first anatomic aspect. The first imaging system is configured to detect visible light, and the second imaging system is configured to detect invisible light such that the first and second imaging systems are configured to detect different anatomic aspects. The different anatomic aspects may facilitate identification of a critical structure's location and thereby facilitate positioning of at least one of the first and second imaging systems and/or facilitate positioning of at least one instrument at the surgical site. The first imaging system is configured to gather real time images during a surgical procedure, such as with a scope. The images gathered by the second imaging system can be preoperative images or can be real time images gathered during the surgical procedure. The first imaging system can thus be controlled based on the patient's known anatomy as indicated by images gathered by the second imaging system as well as on the images gathered by the first imaging system indicative of its current location and orientation.

Figure 23:
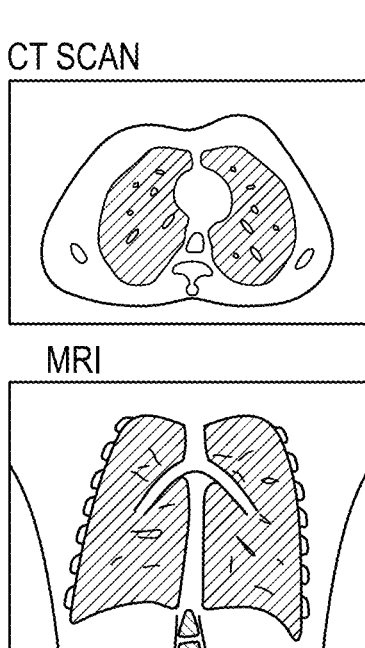
FIG. 23 is a schematic view of one embodiment of a CT scan of a patient and of an MRI of the patient.

For example, a surgical hub, a robotic surgical system, or other computer system can be configured to use preoperative and/or real time images of a patient, such as CT and/or MRI images, gathered by a second imaging system in controlling a scope during performance of a surgical procedure on the patient. The scope's movement can thus be controlled based on the patient's known anatomy as indicated by preoperative data as well as on the data gathered by the scope indicative of its current location and orientation. The preoperative images provide anatomic information of the patient, for example vasculature and/or tumor information. FIG. 23 shows an example of preoperative CT image data of a lung of a patient and an example of preoperative MRI image data of the lung of the patient. A lung is shown by way of example. Data gathered using invisible light may show another body structure, as appropriate for the surgical procedure being performed. As a lung is used in this example, the scope is a bronchoscope, although other types of scopes can be used as appropriate for the procedure being performed and the anatomy accessed. Each of CT image data and MRI image data can be used in controlling the scope, or only one of CT image data and MRI image data can be used. Additionally, as mentioned above, other types of invisible light image data is possible. Image data from the first and second imaging systems may also be shown on a display, as discussed herein.

The control of the scope's movement can include a rate of the scope's advancement to the surgical site, a distance of the scope's advancement to the surgical site, and/or an angle at which the scope is positioned relative to the surgical site. The preoperative images can help inform the rate of the scope's advancement to the surgical site since the scope's current position and the location of the surgical site will each be known. The scope can be advanced more quickly the farther away the scope is from the surgical site and then advanced more slowly as the scope gets closer to or is at the surgical site so the scope's movement can be more granularly controlled at the surgical site to achieve a desired view and/or avoid or access a critical structure as needed. Similarly, the preoperative images can help inform the distance of the scope's advancement to the surgical site with the scope being controlled to move greater distances the farther away the scope is from the surgical site. The preoperative images can help inform the angle at which the scope is positioned relative to the surgical site because the preoperative images can show a critical structure that the scope cannot see using visible light. The scope can thus be positioned at an effective orientation relative to the critical structure so that an instrument can be advanced through the scope to effectively access the critical structure, such as by passing through healthy tissue to an underlying tumor that the scope itself cannot visualize (at least not without the healthy tissue first being cut to expose the underlying tumor).

In some embodiments, cooperative surgical visualization includes tracking of an anatomic location as it undergoes distortions to predict an internal aspect of the anatomy, e.g., predict a tumor. The anatomic location can thus be tracked over two different states, an undistorted state and a distorted state. The undistorted state can provide information useful in determining information, e.g., size, location, shape, and/or orientation, about a tumor or other critical structure in the distorted state.

As mentioned above, in a surgical procedure on a lung such as a lung resection, the lung needs to be collapsed (deflated) for effective performance of the surgical procedure. However, the collapse can make it difficult for a medical practitioner to locate a critical structure such as a tumor based on preoperative and/or intraoperative images in which the lung is not collapsed because the lung collapse can cause the tumor to shift in location and/or change size, shape, and/or orientation. Introducing an imaging system such as a flexible scope into the lung while the lung is inflated can help a surgical hub, a robotic surgical system, or other computer system more easily coordinate the tumor's location as shown via CT imaging with visual and ultrasonic imaging. The scope can be retracted, such as by being automatically retracted by a robotic surgical system controlling the scope, as the lung is deflated to prevent the scope from causing damage to tissue adjacent to the scope with the lung in its deflated state.

Figure 24:
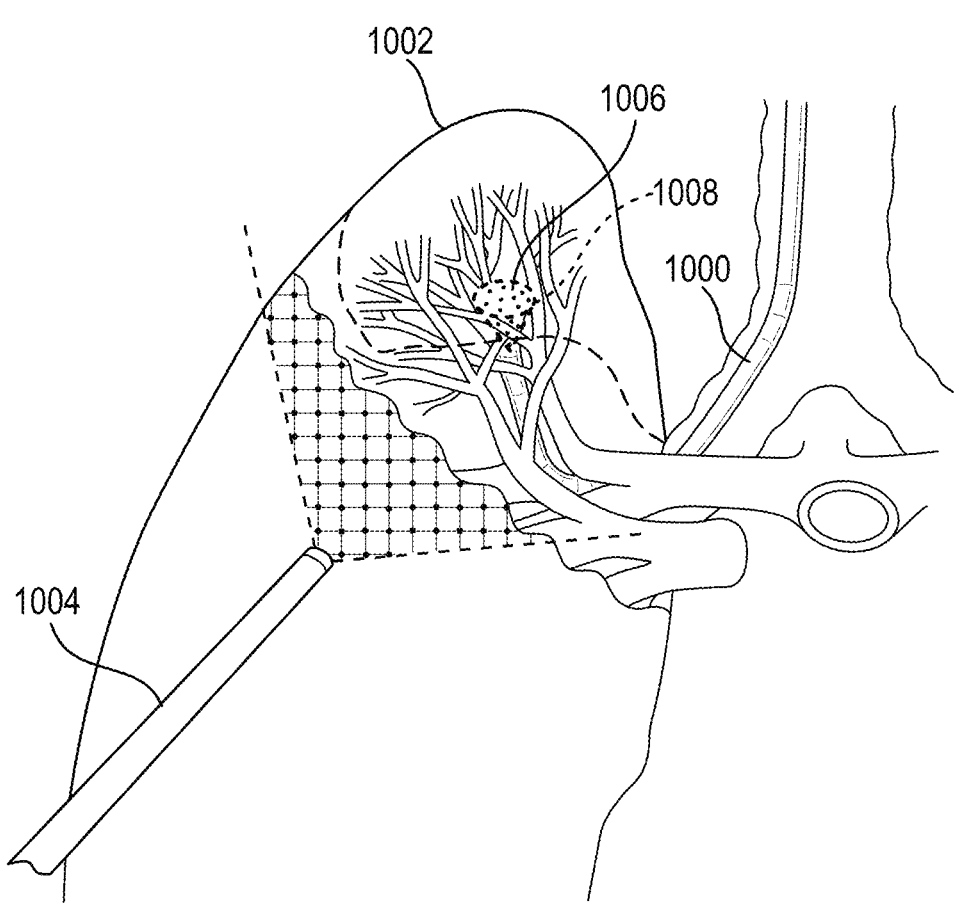
FIG. 24 is a schematic view of a collapsed lung of a patient having a bronchoscope advanced therein.

FIG. 24 shows one embodiment in which a bronchoscope 1000 has been advanced into a lung 1002 and a camera 1004 has been positioned to visualize the lung 1002. The lung 1002 is collapsed in FIG. 24. The bronchoscope 1000 can be introduced via a CT assisted positioning to be desirably positioned relative to a tumor 1006 at the surgical site or can use an ultrasound sensor (obscured in FIG. 24) at a distal end of the bronchoscope 1000 to be desirably positioned relative to the tumor 1006. FIG. 24 illustrates with a dotted line 1008 around the tumor 1006 ultrasound visualization of the tumor 1006 via the ultrasound sensor. The dotted line 1008 can be provided on a display to inform a medical practitioner of the tumor's detected location and extent (size), information which may not be known without invisible imaging such as ultrasound. The dotted line 1008 can be adjusted, such as by a surgical hub, a robotic surgical system, or other computer system, to be larger than the tumor 1006 so as to account for a preplanned margin around the tumor 1006 planned to be excised along with the tumor 1006. The dotted line 1008 can be shown on a display to indicate to a medical practitioner where the tumor 1006 is located even if the tumor 1006 is not visible to the naked eye by being hidden under various structure(s). The dotted line 1008 can be three-dimensional so as to provide 3D viewing of the tumor 1006. Instead of or in addition to ultrasound, one or more other imaging techniques can be used to facilitate locating the tumor 1006, as discussed herein. The dotted line 1008 can dynamically change as the display viewpoint changes and/or as the lung 1002 is collapsed. The dotted line 1008 is an example only, the tumor's location can be identified in other ways, such as by a particularly colored line, by a line defined by a pattern other than dots, by a translucent shape being overlaid on the visualized display at the tumor's location, or in another way.

Figure 25:
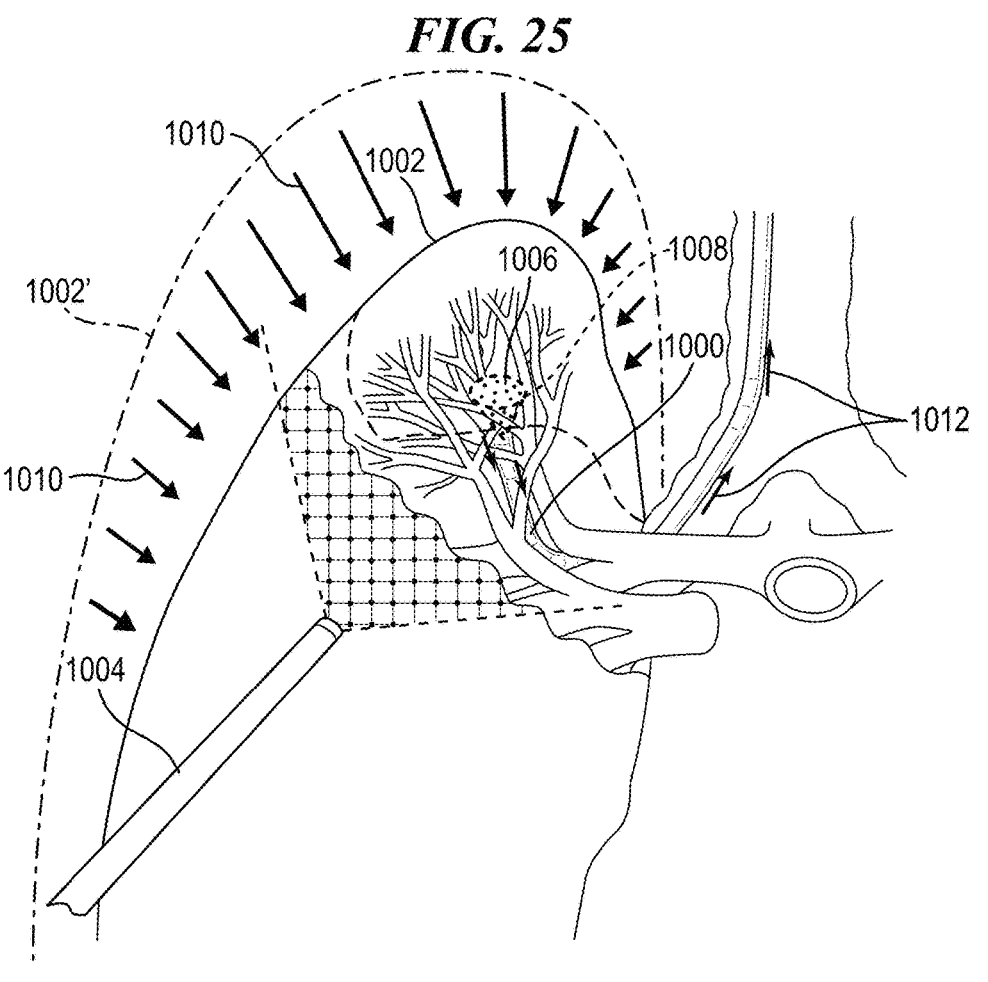
FIG. 25 is a schematic view of retraction of the bronchoscope of FIG. 24.

FIG. 25 illustrates one embodiment of automatic retraction of the bronchoscope 1000 during collapse of the lung 1002 with arrows 1010 showing a direction of the retraction. FIG. 25 shows the collapsed lung 1002 in solid outline as being and shows the inflated lung 1002' in dotted outline with arrows 1012 showing the lung 1002 collapse. The bronchoscope's imaging can be supplemented by preoperative and/or intraoperative CT scan to image the collapsing lung in real time to facilitate the retraction of the bronchoscope 1000 so it is straightened and/or otherwise moved safely, such as to not impact the bronchial branch junction through which the bronchoscope 1000 will pass. One or more elements associated with the bronchoscope 1000, such as an overtube, a control sheath, and any instruments that have been advanced through a working channel of the bronchoscope 1000 to the surgical site, can not be retracted so as to be left at the surgical site, which may help keep track of the identified area of the tumor 1006 (e.g., by leaving the ultrasound sensor at the surgical site (in embodiments in which the ultrasound sensor has been advanced through a working channel of the bronchoscope 1000) and/or by leaving a guidewire-sized catheter at the surgical site providing for a variable wavelength emitting light or LED visible light at the surgical site) and/or may help prevent unintended interaction with tissue as the lung is collapsed.

Figure 26:
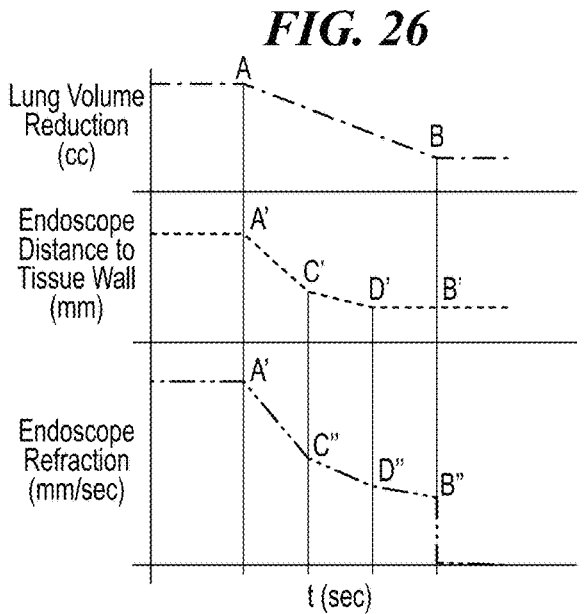
FIG. 26 is a graph showing a rate of retraction of the bronchoscope of FIG. 24, lung volume reduction, and distance between the bronchoscope and an intersecting tissue wall versus time.
Figure 27:
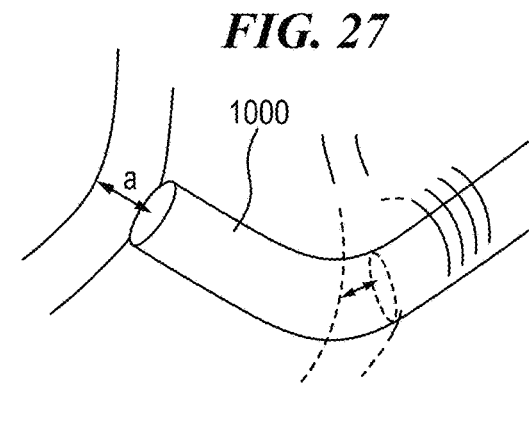
FIG. 27 is a schematic view illustrating the distance of FIG. 26.

The automatic retraction of the bronchoscope 1000 can be controlled based on a plurality of factors. A cumulative or weighted effect of the factors can be used to determine a rate of retraction of the bronchoscope 1000. The factors can include, for example, a distance from the bronchoscope 1000 to the intersecting tissue wall and a rate of change. The rate of change can be a rate of change of lung volume (e.g., CT or ventilator exchange) or a rate of change of the tissue external surface (e.g., as indicated by structured light). FIG. 26 shows a graph indicating a rate of retraction of the bronchoscope 1000 in mm/sec (the bronchoscope 1000 is identified as an "endoscope" in the graph) based on a first factor of lung volume reduction (in cc) and a second factor of bronchoscope 1000 a distance "a" from the bronchoscope 1000 to the intersecting tissue wall (in mm). FIG. 27 illustrates the distance "a."

A lung can be collapsed without the bronchoscope 1000 having first been advanced therein, such that no automatic retraction of a bronchoscope is needed during lung collapse. Without the bronchoscope 1000 in position prior to lung collapse, the tumor 1006 may not be visualized using the ultrasound sensor associated with the bronchoscope 1000 before lung collapse. CT imaging and/or structured light imaging can be used to compare the inflated lung 1002' to the collapsed lung 1002 to track the location and size of the tumor 1006 to facilitate advancement of the bronchoscope 1000 to the tumor 1006 after lung collapse. FIG. 28 illustrates the inflated lung 1002' and the location and size of the tumor 1006' with the lung 1002' inflated, and illustrates the deflated lung 1002 and the location and size of the tumor 1006 with the lung 1002 deflated. FIG. 28 also illustrates a working space 1014 made available after lung collapse for, e.g., tools to be effectively positioned in the patient.

FIG. 29 shows an enlarged detail of the collapsed-state tumor 1006 and inflated-state tumor 1006', which demonstrates how a tumor can be affected and change between lung inflation and deflation, thus also demonstrating how lung collapse can adversely affect being able to locate and access a tumor after lung collapse. The illustrated tumor 1006, 1006' is a ground-glass opacity nodule (GGN) and is an example only. Other tumors, even other GGN tumors, can have different locations, compositions, and sizes and can accordingly change differently in response to lung collapse.

The lung 1002' can be collapsed to control collapse of the tumor 1006' to create a predefined tumor size and shape, e.g., a predefined size and shape of the collapsed-state tumor 1006. The predefined tumor size and shape can correspond to a preferred size and shape for tumor ablation, such as by the collapsed-state tumor 1006 having a size and shape that correlates to microwave antenna performance and/or to a zone of the ablation for optimal energy delivery (e.g., an area of ablation that an ablation device can create). The predefined tumor size and shape can thus be different based on the particular ablation device being used. The controlled lung collapse may facilitate patient treatment by facilitating access to the collapsed-state tumor 106 and thus facilitate effective ablation of the tumor 1006 with the lung 1002 collapsed. Examples of ablation devices are NeuWave™ ablation probes (available from Ethicon US LLC of Cincinnati, OH), which have an ablation zone of 2 cm. Another example of an ablation device is the Hyblate catheter ablation probe (available from Hyblate Medical of Misgav, Israel). Another example of an ablation device is the Barxx™ HaloFlex (available from Medtronic of Minneapolis, MN). Other examples of ablation devices are discussed further in, for example, U.S. patent application Ser. No. 17/494,364 entitled "Surgical Methods For Control Of One Visualization With Another" filed on Oct. 5, 2021.

An amount of lung collapse during lung deflation can be monitored in X, Y, and Z directions using imaging such as any one or more of CT, x-ray, ultrasound, visualization using the bronchoscope 1000, and MRI. The inflated size of the lung is known, e.g., as determined via preoperative imaging, so visualizing the lung during collapse can indicate the lung's percentage of collapse as the lung moves from inflated toward being fully deflated. The imaging during lung collapse can also visualize the tumor so as to indicate a size and shape of the tumor with the lung in its current state of deflation. The tumor's density may also be captured by the imaging. When the tumor has reached a size and shape that can be effectively ablated, e.g., given the ablation device's microwave antenna performance and/or the ablation device's ablation zone, the lung collapse can be stopped. A lung being collapsed for a long period of time can hinder the lung's ability to be re-inflated and/or can allow fluid to build up in the lung cavity. Minimizing an amount that the lung is collapsed by monitoring the tumor during lung deflation and stopping the lung deflation when the tumor can be effectively accessed and ablated may reduce an amount of time that the lung is in a collapsed state because the lung has not been fully collapsed (in most situations with most tumors), may help the lung be more quickly re-inflated, and/or because the lung is deflated an optimal amount in the first place without having to additionally deflate the lung if not initially deflated enough for effective tumor ablation. Controlled lung collapse so the lung collapse is stopped when the tumor has a size and shape within the ablation zone of the ablation device being used to deliver energy to the tumor may help prevent more healthy tissue than is necessary from being ablated because the lung collapse can cease just after the tumor has a size and shape for effective ablation. Ablating a tumor too close to the pleural wall, such as about 1 cm or closer to the pleural wall, could cause damage to the pleural wall, so controlled lung collapse stopping before full lung collapse may help keep the tumor at a safe distance from the pleural wall during ablation.

Figure 31:
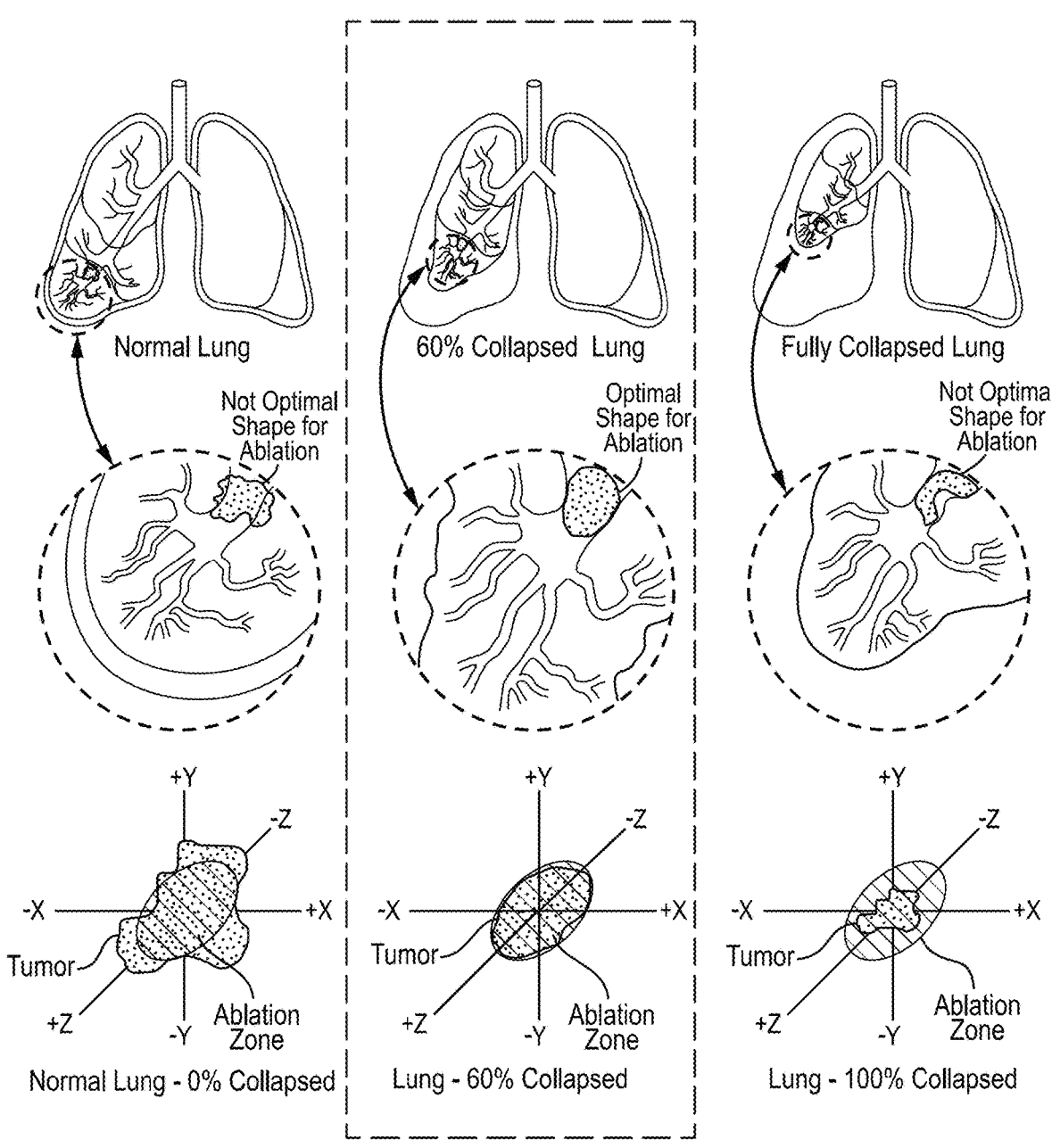
FIG. 31 is a schematic view of an optimal percentage of lung collapse as compared to an inflated lung and a fully delated lung.

FIG. 30 shows a graph indicating ablation zones with respect to a percentage of lung collapse versus tumor size in X, Y, and Z directions. FIG. 31 shows an optimal percentage of lung collapse to ablate a tumor and minimize therapeutic treatment to healthy tissue, as compared to an inflated lung and a fully delated lung. The optimal percentage in this illustrated embodiment is 60%. As shown in FIG. 31, the ablation zone in this illustrated embodiment is elliptical, so having information in multiple directions may help ensure that the tumor at a particular percentage of lung collapse can be effectively ablated since a center of the ablation zone is not a center of the ablation zone's shape like with a circle or a square. With the lung inflated (0% collapsed) the size and shape of the tumor exceeds the ablation zone. With the lung fully collapsed (100% collapsed) there is more healthy tissue in the ablation zone than with the lung inflated, and thus that would be ablated were the tumor ablated with the lung fully collapsed, than with the lung collapsed at 60%. In other instances, the ablation zone may be more circular than elliptical or have a differently sized elliptical shape, e.g., because different ablation devices create differently shaped ablation zones, in which case a different amount of lung collapse may correspond to a size and shape of the tumor for effective ablation.

Different ablation devices can concentrate energy differently, such as some ablation devices concentrating energy pointing proximally from a tip of the ablation device and others concentrating energy pointing distally from a tip of the ablation device. Using multiple types of imaging during lung collapse may allow for images of the tumor to be gathered that will be helpful in determining where to position the ablation device relative to the tumor to help ensure full ablation of the tumor while minimizing damage to healthy, non-targeted tissue.

Controlled lung collapse can be performed in a variety of ways, such as by a combination of extracting air from the airway and controlled sealing and venting by the bronchoscope 1000 if advanced into the lung 1002 before lung collapse. This technique allows portions of the bronchus airways to be sealed and allow other portions of the bronchus airways to be selectively collapsed, thereby causing air removal and tissue strain from adjacent areas to compact the tumor 1006 into the predefined size and shape. Which airways to seal, where to position balloons used to create the seal (in embodiments in which sealing is performed using inflatable balloons), which airways to evacuate, and how much air to evacuate from each of the evacuated airways can be pre-operatively determined by, for example, performing a surgical simulation via a surgical hub that is later used operatively to seal airways as sealed in the surgical simulation saved at the surgical hub and to evacuate airways as evacuated in the surgical simulation saved at the surgical hub. In embodiments in which the bronchoscope 1000 was not advanced into the lung 1002 before lung collapse, controlled lung collapse can be performed, for example, by extracting air from the airway. Which airways to evacuate and how much air to evacuate from each of the evacuated airways can be pre-operatively determined by, for example, performing a surgical simulation via a surgical hub that is later used operatively to evacuate airways as evacuated in the surgical simulation saved at the surgical hub.

As mentioned above, the tumor 1006 can be visualized. In some instances, the tumor 1006 cannot be visualized, such as if an imaging device that can visualize using invisible light is not being used and tissue overlies the tumor 1006 so as to prevent visualization of the tumor 1006 using visible light. In such instances, the overlying tissue can be imaged and tracked similar to that discussed above regarding the tumor 1006 so that the size and shape of the tumor 1006 known to be under the tissue, e.g., because of preoperative imaging, can be predicted based on the changing size and shape of the overlying tissue during lung collapse. A dotted line similar to the dotted line 1008 (or indicator other than a dotted line, as discussed above) can be provided on a display to indicate that predicted size and shape of the tumor 1006 based on the overlying tissue. The predicted size and shape of the tumor 1006 can be used similar to that discussed above in determining how much to collapse the lung 1002 for effective ablation of the tumor 1006.

A structured light projection, as discussed herein, can be used to image and track the overlying tissue. For example, FIG. 32 illustrates one embodiment of using a structured light projection of a laser array supplemented by tissue surface marks to map external surface deformation of a lung to provide information about a tumor in the lung. The differences of the two arrays over time as the lung is deformed allows the surgical hub, a robotic surgical system, or other computer system to measure geometry and tissue strain. FIG. 32 shows the lung 1020 in an inflated state with a corresponding tissue surface geometry 1022, shows the lung 1020' in a partially collapsed state with a corresponding tissue surface geometry 1022', and shows the lung 1020" in a fully collapsed state with a corresponding tissue surface geometry 1022". FIG. 33 shows physical organ tag markers 1024, which can be ink marks or other tag markers, and projected structured light 1026 corresponding to the inflated state (lung 1020 and tissue surface geometry 1022). FIG. 34 shows the physical organ tag markers 1024 and the projected structured light 1026 corresponding to the fully collapsed state (lung 1020" and tissue surface geometry 1022"). With respect to the projected structured light 1026, the physical organ tag markers 1024 have become distorted moving from the inflated state to the partially collapsed state, and further distorted moving from the partially collapsed state to the fully collapsed state. The distortion of the physical organ tag markers 1024 with respect to the projected structured light 1026 measures strain of the lung. The measured strain can then be used to estimate the size and shape of the tumor underlying the strained tissue. In this way, the tumor's size and shape can be predicted.

FIG. 35 illustrates one embodiment of a method 1030 of predicting tumor size using measured tissue strain. The method 1030 is described with respect to a lung illustrated in FIG. 36.

In the method 1030, the lung 1056 is imaged 1032 in the inflated state. CT imaging is used in this example but other imaging is possible. The imaging of the inflated lung 1056 indicates a state of the tissue without strain. The lung 1056' is then partially collapsed 1036, to an 80% partially collapsed state in this illustrated embodiment.

A surgical device 1050 (a scope in this illustrated embodiment) is introduced 1036 to the surgical site and positioned relative to the partially collapsed lung 1056'. An imaging device 1052 is also introduced to the surgical site, either before or after the surgical device 1050, and positioned relative to the partially collapsed lung 1056'. The surgical device 1050 is similar to the surgical device 102 of FIG. 1, the surgical device 202 of FIG. 8, or other surgical device described herein, and the imaging device 1052 is similar to the imaging device 120 of FIG. 1, the imaging device 220 of FIG. 8, or other imaging device described herein. The surgical device 1050 provides a structured light pattern 1054, as described herein, on the partially collapsed lung 1056'. The structured light pattern 1054 is a dot pattern in this illustrated embodiment. The imaging device 1052 detects the structured light pattern 1054, as described herein.

Physical organ tag markers 1058 are on the surface of the lung. The markers 1058 are tattooed ink marks in this illustrated embodiment but other markers are possible. The markers 1058 have been applied with the lung 1056 in the inflated state.

Figure 38:
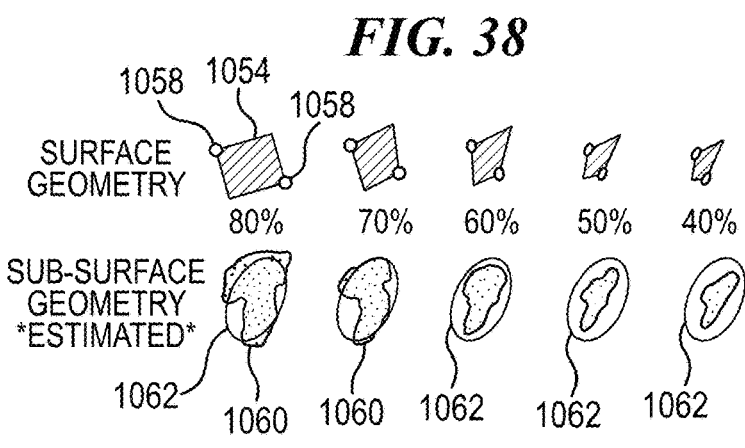
FIG. 38 shows surface geometry and estimated subsurface geometry for the lung of FIG. 36.

With the lung 1056' in the partially collapsed state, a tissue surface deformation map is created 1038 based on the structured light pattern 1054, as discussed herein. The tissue surface deformation map is compared 1040 to the inflated lung image to generate 1042 a tissue strain (or stress) collapsed 3D model of a tumor underlying the lung tissue surface. The generated 1042 3D model can be shown on a display, such as with a dotted line, translucent shape, etc. as described herein, to show the estimated tumor size and shape. FIG. 37 and FIG. 38 illustrate the 80% partially collapsed lung 1056' and the estimated sub-surface geometry of the tumor 1060' with the lung 1056' 80% collapsed. FIG. 38 also shows the estimated sub-surface geometry of the tumor 1060 compared to an ablation zone 1062 of an ablation device to be used to ablate the tumor. The ablation zone 1062 is elliptical in this illustrated embodiment. As the lung continues to be collapsed, a tissue surface deformation map is created 1038 based on the structured light pattern 1054 and compared 1040 to the inflated lung image to generate 1042 a tissue strain (or stress) collapsed 3D model of the tumor corresponding to that state of lung collapse. FIG. 38 shows the estimated sub-surface geometry of the tumor 1060 compared to the ablation zone 1062 at 70% lung collapse, 60% lung collapse, 50% lung collapse, and 40% lung collapse. The estimated tumor geometry can be displayed at each of these lung collapse states as well as lung states therebetween. The tumor's size and shape can thus be visualized in real time during performance of the surgical procedure. The tumor 1060 first fits within the ablation zone 1062 at 60% lung collapse, but the lung continues being collapsed to 40% lung collapse in this illustrated embodiment to help ensure full ablation of the tumor. FIG. 38 also illustrates the deformation of the tissue at each of the 80%, 70%, 60%, 50%, and 40% lung collapse states. FIG. 36 shows the inflated lung 1056, the 80% collapsed lung 1056', the 40% collapsed lung 1056" (also shown in FIG. 37), and 0% (fully deflated) lung 1056". The lung is not fully deflated in this method 1030 but a lung can be fully deflated, or partially deflated at less than 40%, in other embodiments to achieve a desired tumor size and shape.

With the lung 1056" at 40% collapse, which corresponds to the estimated tumor size and shape being at the predefined size and shape corresponding to a preferred size and shape for tumor ablation, the lung 1056" is again imaged 1044. As mentioned above, CT imaging is used in this example. The lung 1056" being imaged 1044 allows the actual size and shape of the tumor 1060 to be determined. The lung can then be inflated or deflated further as needed to achieve the predefined size and shape should the actual tumor 1060 size and shape not sufficiently correspond to the estimated tumor 1060 size and shape.

With the lung deflated as desired, the tumor 1060 is ablated. The effect of the ablation can be monitored, such as by using multi-spectral imaging or using electromagnetic or RF monitoring, to determine an actual ablation zone. The actual ablation zone and the overlaid ablation zone 1062 can each be used to enable more precise treatment triangulation and feedback control to the ablation system that includes the ablation device.

In some embodiments, a camera can provide an intraluminal view, such as by a bronchoscope being introduced into the lung in the inflated state. As the lung is collapsed, e.g., as the lung is deflated to the 40% collapsed state, the intraluminal imaging can be used in combination with the structured light imaging to determine a shape, thickness, and configuration of a tissue wall separating the two visualization systems. Monitoring the shape, thickness, and configuration of the tissue wall is another way that the tissue distortion or tissue strain can be determined. Various embodiments of tissue monitoring are discussed further, for example, in U.S. patent application Ser. No. 17/494,364 entitled "Surgical Methods For Control Of One Visualization With Another" filed on Oct. 5, 2021.

3D Surgical Visualization

Surface irregularities (e.g., deformations and/or discontinuities) on tissue can be difficult to capture and portray in a visualization system. Additionally, tissue often moves and/or changes during a surgical procedure. In other words, tissue is dynamic. For example, the tissue may be distorted, stressed, or become otherwise deformed by a surgical fastening operation. The tissue may also be transected and/or certain portions and/or layers of tissue may be removed. Underlying tissue and/or structures may become exposed during the surgical procedure. As the tissue moves, embedded structures underlying the visible tissue and/or hidden tissue margins within an anatomical structure may also move. For example, a resection margin may be concentrically positioned around a tumor prior to tissue deformation; however, as the anatomical structure is deformed during a surgical procedure, the resection margin may also become deformed. In certain instances, adjacent portions of tissue can shift, including those portions with previously-identified physical characteristics or properties. Generating 3D digital representations or models of the tissue as it is deformed, transected, moved, or otherwise changed during a surgical procedure presents various challenges; however, such dynamic visualization imaging may be helpful to a clinician in certain instances.

In various instances, an adaptive visualization system can provide visualization of motion at the surgical site. Structured light can be used with stereoscopic imaging sensors and multi-source coherent light to map light pattern distortions from one time frame to another time frame. The mapping of light pattern distortions across frames can be used to visualize and analyze anatomic distortion. Moreover, as the 3D digital representations or models are deformed, any superimposed 3D imaging, such as embedded structures, tissue irregularities, and/or hidden boundaries and/or tissue margins, can be proportionately deformed with the 3D model. In such instances, the visualization system can convey movement of the superimposed 3D imaging to a medical practitioner as the tissue is manipulated, e.g., dissected and/or retracted.

An adaptive visualization system can obtain baseline visualization data based on situational awareness (e.g., input from a situational awareness system). For example, a baseline visualization of an anatomical structure and/or surgical site can be obtained before initiation of a surgical procedure, such as before the manipulation and dissection of tissue at the surgical site. The baseline visualization image of the anatomical geometry can include a visualization of the surface of the anatomical structure and its boundaries. Such a baseline visualization image can be used to preserve overall orientation of the surgical site and anatomic structure even as local regions within the anatomic structure are progressively disrupted, altered, or otherwise manipulated during the surgical procedure. Maintaining the baseline visualization image can allow the disrupted regions to be ignored when mapping other imaging irregularities. For example, when mapping or overlaying structures and/or features obtained by other imaging sources, the baseline visualization image can be used and the distorted regions ignored to appropriately position the additional structures and/or features in the updated visualization image.

Various systems and methods of generating 3D digital representations or models of tissue and conveying the 3D models to medical practitioners are further described in, for example, previously mentioned U.S. patent application Ser. No. 16/729,747 entitled "Dynamic Surgical Visualization Systems" filed Dec. 30, 2019.

Devices, systems, and methods for multi-source imaging provided herein may allow for enhanced 3D surgical visualization. In general, the devices, systems, and methods can allow identification and accentuation of anatomical gateways by differentiating tissue planes, localized anomalies, and tissue configuration or composition to enhance a 3D model being used for visualization. In an exemplary embodiment, multiple visualization views can be used to identify, locate, and define boundaries of connective soft tissue planes. The defined planes can be related to a structure and role of the tissue. Examples of the structure and role include tissue composition, tumor location, tumor margin identification, adhesions, vascularization, and tissue fragility. Irregularities can be localized and overlaid onto the defined tissue planes on a display. Properties of a displayed tissue plane may be visible on the display, such as by a medical practitioner highlighting or otherwise selecting the tissue plane. Examples of the properties include tissue type, collagen composition, organized versus remodeled disorganized fiber orientation, tissue viability, and tissue health.

In some embodiments, enhanced 3D surgical visualization includes augmenting cooperative imaging resulting from multiple visualization sources, e.g., from a plurality of imaging devices, to form a composite map. The composite map can identify localized aspects, markers, or landmarks. These enhanced components can be coupled to a surgical procedure plan or global anatomy to identify and highlight aspects of the tissue that correspond to steps in the surgical procedure plan and directions improving visualization during performance of the steps.

Figure 39:
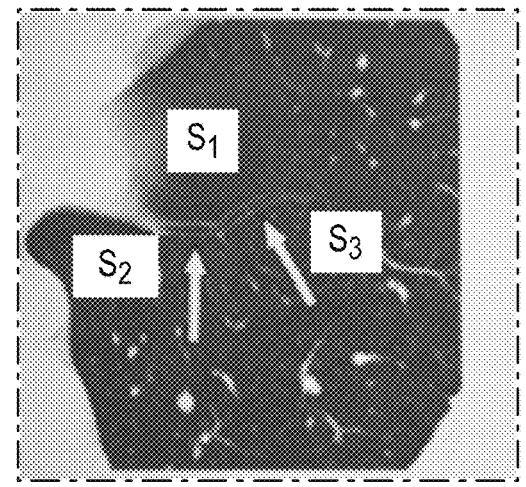
FIG. 39 is a CT image showing an intersegmental plane between three tissue segments.
Figure 40:
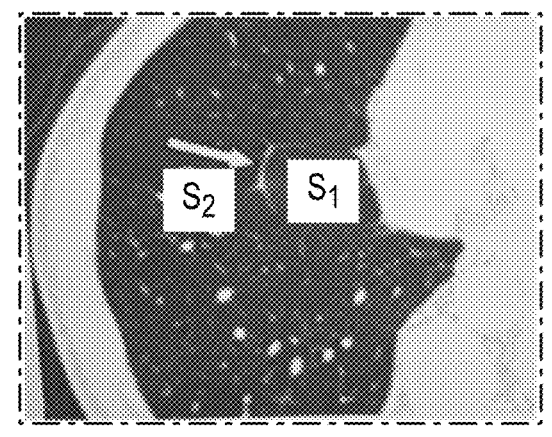
FIG. 40 is a CT image showing an intersegmental plane between two of the tissue segments of FIG. 39.

A CT image of a patient can show a tissue plane between tissue segments. The CT image can be used to locate or identify the tissue plane and display the tissue plane relative to another image of the patient gathered by an imaging device, such as by overlaying a representation of the tissue plane on the image gathered by the imaging device and shown on the display. By way of example, FIG. 39 shows a CT image of a lung with two arrows pointing to an intersegmental plane between segments $S_1$, $S_2$, and $S_3$. Other white lines and areas in the CT image are vessels and airways. FIG. 40 shows another CT image of the lung with one arrow pointing to an intersegmental plane between segments $S_1$ and $S_2$. Other white lines and areas in the CT image are vessels and airways.

Multiple sources of visualization can be overlaid to form a single visualization on a display. The display can also show a secondary global view to coordinate imaging views and reduce confusion or loss of orientation. In an exemplary embodiment, the overlaid information can include identified tissue plane(s) overlaid on a primary visualization provided by a rigid scope. The single visualization can thus define tissue plane location and orientation relative to the primary view to direct tissue plane dissection and separation being executed by a user, such as by the user controlling one or more surgical instruments manually or using a robotic surgical system.

Figure 41:
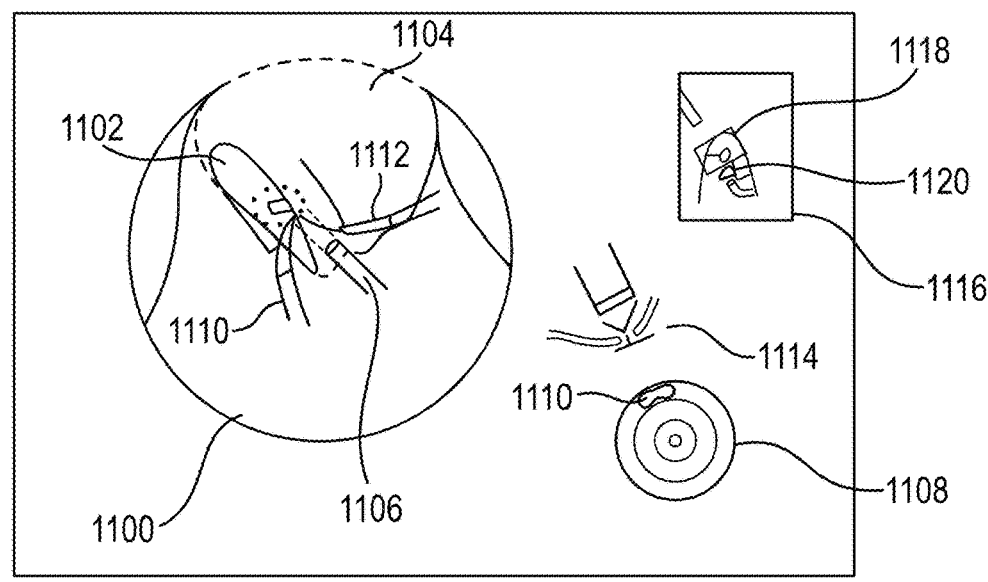
FIG. 41 is a schematic view of a display.

FIG. 41 illustrates one embodiment of a display showing a thoracoscopic view 1100 provided by a rigid scope and showing a tissue plane 1102. A flexible scope 1106 providing a flexible scope view 1108 is visible by the rigid scope and is thus shown in the thoracoscopic view 1100. The rigid scope view 1100 also shows first and second surgical instruments 1110, 1112 at the surgical site. The surgical instruments 1110, 1112 are each dissectors configured to dissect tissue, e.g., to separate tissue at the tissue plane 1102, for removal of a specimen 1104, such as a tumor, that is also visible in the rigid scope's view 1100. The display also shows a ghosted thoracoscopic view 1114 and a 3D model 1116 showing the thoracoscopic visualization plane 1118 and the flexible scope visualization plane 1120.

The display also shows the flexible scope view 1108, which is the view seen by the flexible scope 1106. A medical practitioner can thus see on a single display what each of the rigid and flexible scopes are visualizing. The view 1100 provided by the rigid scope is the primary view on the display, as indicated by its size being larger than the flexible scope view 1108. The medical practitioner can switch between which view is the primary view, and thus which is the larger view on the display.

Figure 42:
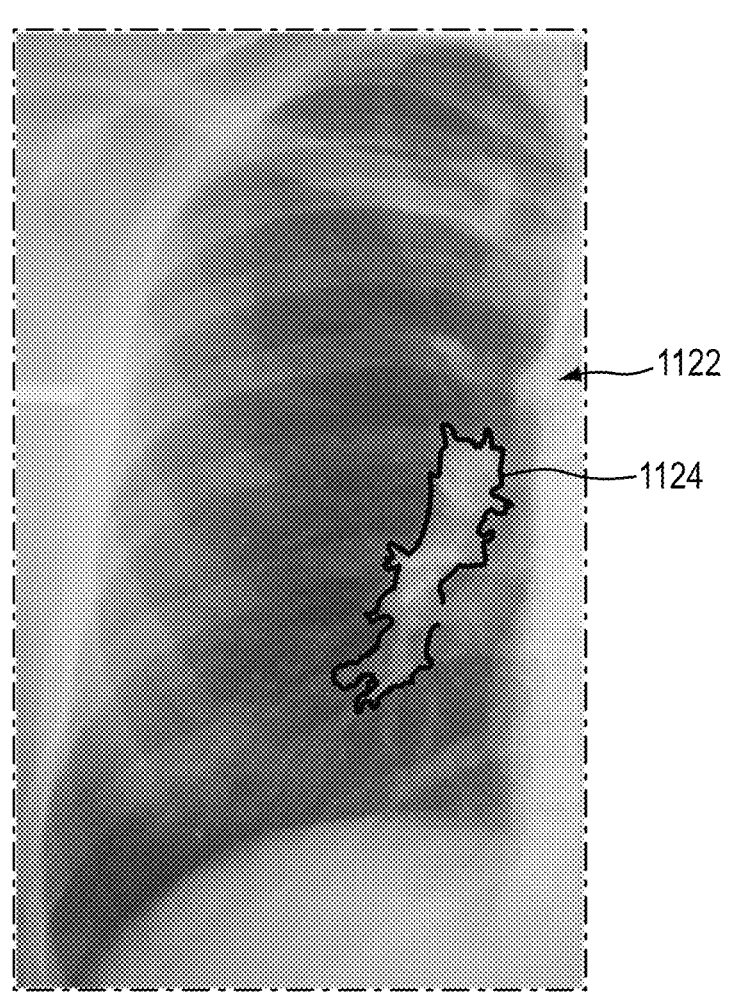
FIG. 42 is an enhanced CT image of a lung.

FIG. 42 illustrates another embodiment in which a CT image 1122 is enhanced with an overlay 1124 outlining an identified critical structure, which is a tumor in this example. Images taken over time can be used to develop the overlay 1124, as discussed herein. The overlay 1124 allows airways to be distinguished from the critical structure. The CT image 1122 shows a lung, but CT images of other anatomic structures can be similarly overlaid. Also images other CT images, such as ultrasound images or MRI images, could similarly have an overlay.

In some embodiments, enhanced 3D surgical visualization includes adaptive differentiation and mapping convergence of a first imaging system via a second imaging system. In other words, enhanced mapping and guidance can be provided using visualizations of a surgical site from different imaging sources. Images gathered by the first imaging system can be enhanced with images from the second imaging system such that the first imaging system is the primary system and the second imaging system is the secondary system. The images gathered by the first imaging system can be enhanced by adding information obscured from the first imaging system but visible by the second imaging system and/or by differentiating aspects of the primary imaging for secondary usage.

For example, in a surgical procedure on a lung, the adaptive differentiation and mapping convergence can include progressive flexible scope imaging of the lung's airways. A front view of lung airways is shown in FIG. 43. FIG. 44 and FIG. 45 show one example of a path of advancement for a flexible scope 1130 in a lung. As the flexible scope 1130 is introduced into the lung, progressive imaging of the lung's internal architecture linked to the scope's tracked position and orientation can be used, e.g., by a surgical hub or other computer system, to enhance, and confirm or adjust, a CT mapping of the airway routes from a moving or indexing starting point to an intended destination, such as a tumor in the lung. In this way, as the flexible scope 1130 advances in the lung, a display can show the scope's progressive advancement along the path of advancement and map (which may include altering) any changes in the CT scanned geometry as the flexible scope 1130 advances. The mapping of local adjacent anatomic structures as the flexible scope 1130 is advanced into position may improve detail along the path of advancement, may provide another data point to confirmation of the primary global CT mapping so as to allow more points of fiducial comparison, and/or may allow the medical practitioner controlling the flexible scope 1130 (and/or other medical practitioner) to define desired local nodal dissection (if any) around a tumor margin or within a zone of confirmation that would allow stoppage during the tumor extraction procedure to dissect out the desired nodes since their locations have already been identified and recorded. The progressive advancement can be enhanced by a Lidar array. The Lidar array allows more precise distance measurement to ultrasound surfaces and thus to the underlying structure.

Figures 46, 47:
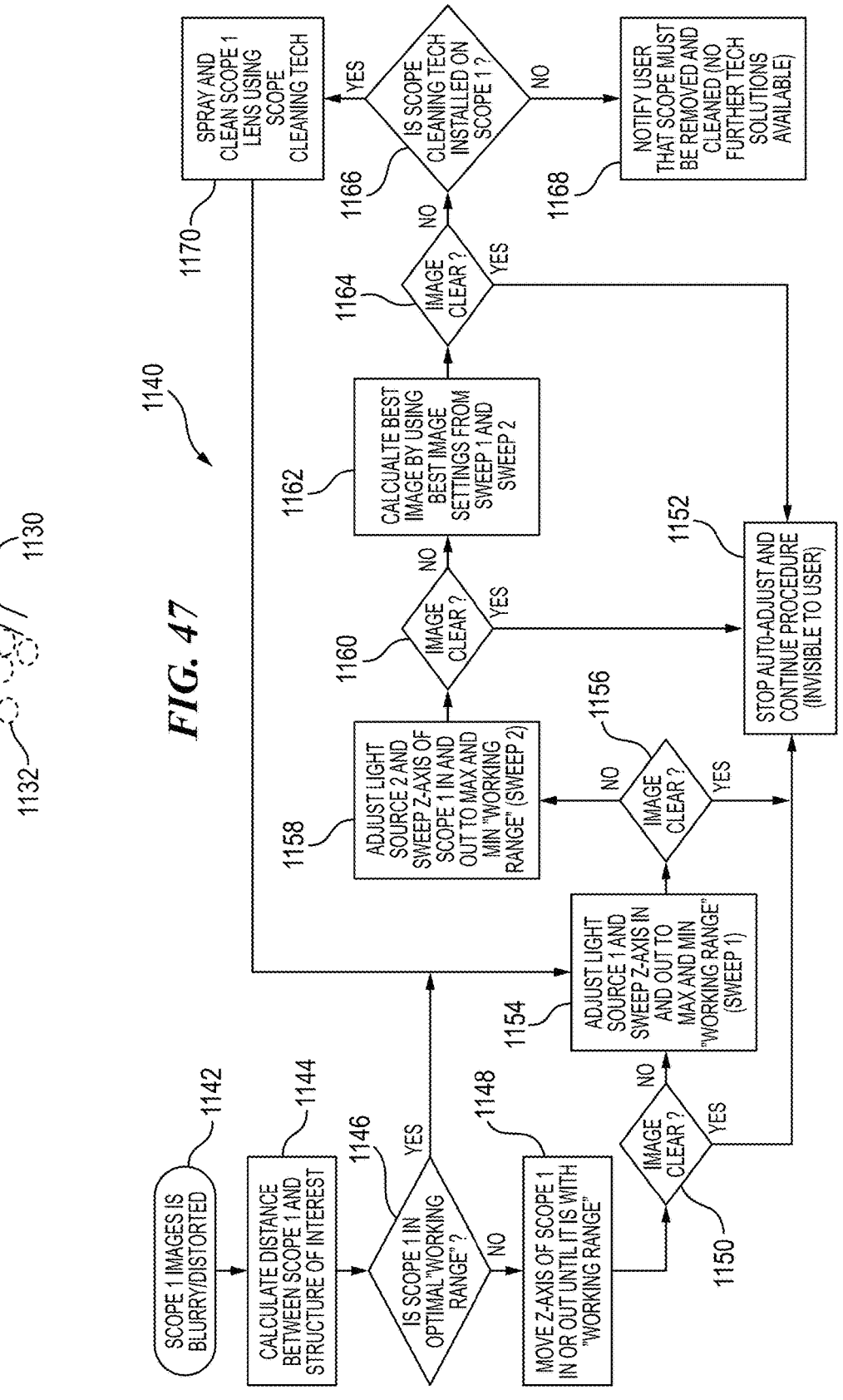
FIG. 46 is a schematic partially cross-sectional view of the scope of FIG. 44 in the lung.
FIG. 47 is a flowchart showing one embodiment of a method of using primary and secondary imaging systems.

FIG. 46 illustrates one embodiment of a display of nodes 1132 that may be defined and dissected as desired. Six nodes are shown, but a different number may be present. FIG. 46 also shows the flexible scope 1130, as a radial endobronchial ultrasound (R-EBUS) probe, in an airway 1134 en route to its intended destination of a tumor 1136. Progressive radial ultrasound achieved using the R-EBUS probe 1130 can be used to facilitate the node 1132 identification and recording. The R-EBUS probe's array can be positioned in a radially spinning connection that allows for circumferential scanning of the anatomy below the locally presented bronchial surface of the airway 1134 in which the scope 1130 is positioned, thereby enabling the scope 1130 to detect nodes, tumors, and irregularities in the anatomy as the scope 1130 is advanced in the lung.

Procedures in other anatomic locations may be similarly mapped and nodes, tumors, and irregularities in the anatomy similarly detected.

For another example, a secondary imaging system using wavelengths outside the visible light range can be used to identify and/or improve visualization features that are obscured from a primary imaging system using visible light and/or to augment the primary imaging system's information regarding those features. In an exemplary embodiment, a secondary imaging system uses multi-spectral imaging using non-visible light, such as light in infrared (IR) and ultraviolet (UV) spectrums, during a surgical procedure to identify features that are obscured to a primary imaging system using visible light for visualization. Light in the ultraviolet spectrum penetrates tissue poorly but can be helpful in identifying superficial crevices, shapes, and other features. Ultraviolet imaging can be performed, for example, using filters on a CMOS array with a UV source coupled to a primary light source or, for another example, using a multi-laser 480 Hz UV, R, G, B, IR imaging system where each spectrum is pulsed separately to create a composite 60 Hz image for display. Light in the infrared spectrum penetrates tissue well and can thus be helpful in identifying structure covered by superficial connective tissue, fat, or other thin tissues that prevent visible light imaging from seeing the underlying structure. Examples of multi-spectrum imaging, such as those that can be used to calculate surface refractivity of tissue to determine the tissue's composition and irregularities, are further described, for example, in U.S. Pat. Pub. No. 2019/0200905 entitled "Characterization Of Tissue Irregularities Through The Use Of Mono-Chromatic Light Refractivity" published Jul. 4, 2019, which is hereby incorporated by reference in its entirety. Examples of 3D imaging using structured light, such as the coupling of 3D generated constructs to key anatomic structures to enable the visualization of tissue parameters, procedure layout plan, predictive distortion of superimposed images, and instrument characterization, are further described, for example, in previously mentioned U.S. Pat. Pub. No. 2021/0196385 entitled "Surgical Systems For Generating Three Dimensional Constructs Of Anatomical Organs And Coupling Identified Anatomical Structures Thereto" published Jul. 1, 2021.

The features may be obscured (fully or partially) to visible light imaging due to being covered by fluid, being covered by tissue, having a washed out contrast, having a similar color to adjacent structure(s), and/or having a similar reflectivity to adjacent structure(s). The secondary imaging may allow for visualization underneath obscuring fluid and/or tissue that visible light visualization cannot provide. The secondary imaging improves contrast of the features and may thus help identify features having a washed out contrast, having a similar color to adjacent structure(s), and/or having a similar reflectivity to adjacent structure(s). A washed out contrast may exist because a visual light imaging system is typically used with as high a brightness level (brightness intensity) as is possible or tolerable to improve visualization of the surgical site. However, the high brightness level tends to wash out the contrast of instruments and tissues, particularly any tissues directly outside of the focused-on site.

The secondary information gathered by the secondary imaging system can be provided via overlay on a display showing the primary information gathered by the primary imaging system (or showing a 3D model generated using the primary images), which may allow a medical practitioner to look at one display for complete visualization information and/or may help the medical practitioner make better decisions on the fly regarding navigation, dissection, and/or other procedure steps than would be possible if only the primary imaging was available without the enhancement provided by the secondary imaging. The non-visible light can be projected at a different intensity than the visible light and/or can be varied over its exposure to improve resolution of identified contrasts, which may allow a surgical hub, a robotic surgical system, or other computer system (e.g., a controller thereof) to look for contrast separately from the visible light imaging and then overlay the visible and non-visible light imaging. If the surgical hub, robotic surgical system, or other computer system detects a contrast that is irregular or inconsistent, the surgical hub, robotic surgical system, or other computer system can automatically adjust field-programmable gate array (FPGA) isolation of the contrast to enhance it or can automatically adjust the intensity while using the irregular or inconsistent region as a focal guide to adjust contrasting to the portions of the image that are most difficult to contrast.

FIG. 47 illustrates one embodiment of a method 1140 of using a primary imaging system utilizing visible light and a secondary imaging system utilizing wavelengths outside the visible light range to identify and/or improve visualization features that are obscured from the primary imaging system. In the method 1140, a surgical hub, a robotic surgical system, or other computer system (e.g., a controller thereof) determines 1142 that an image of a structure gathered by an imaging device (a scope in this example) of the primary imaging system are blurry or distorted. The surgical hub, robotic surgical system, or other computer system calculates 1144 a distance between the scope and the structure. Based on the calculated distance, the surgical hub, robotic surgical system, or other computer system determines 1146 whether the scope is within an optimal working range for visualization. If the calculated distance is above a predetermined maximum threshold distance, the scope can be considered to be outside the optimal working range by being too far away from the structure for optimal non-blurry, non-distorted imaging. If the calculated distance is below a predetermined threshold minimum distance, the scope can be considered to be outside the optimal working range by being too close to the structure for optimal non-blurry, non-distorted imaging.

If the scope is determined 1146 to not be in the optimal working range, the surgical hub, robotic surgical system, or other computer system causes 1148 the Z-axis of the scope to move in or out until the distance is within the optimal working range. The surgical hub, robotic surgical system, or other computer system then determines 1150 whether an image of the structure gathered by the imaging device, after the causing 1148, is clear. If the image is determined 1150 to be clear, then automatic adjustment of the scope stops 1152 and the surgical procedure continues (invisible to the user). If the image is determined 1150 to not be clear, the surgical hub, robotic surgical system, or other computer system adjusts 1154 a light source of the primary imaging system and sweeps the Z-axis of the scope in and out within the optimal working range, e.g., to the predetermined maximum threshold distance and predetermined minimum threshold distance. Then, the surgical hub, robotic surgical system, or other computer system then determines 1156 whether an image of the structure gathered by the imaging device, after the adjustment 1154, is clear. If the image is determined 1156 to be clear, then automatic adjustment of the scope stops 1152 and the surgical procedure continues (invisible to the user). If the image is determined 1156 to not be clear, the surgical hub, robotic surgical system, or other computer system adjusts 1158 a light source of the secondary imaging system and sweeps the Z-axis of the scope in and out within the optimal working range. Then, the surgical hub, robotic surgical system, or other computer system determines 1160 whether an image of the structure gathered by the imaging device, after the adjustment 1158, is clear. If the image is determined 1160 to be clear, then automatic adjustment of the scope stops 1152 and the surgical procedure continues (invisible to the user). If the image is determined 1160 to not be clear, the surgical hub, robotic surgical system, or other computer system calculates 1162 best image settings from the first adjustment 1154 and the second adjustment 1158. Then, the surgical hub, robotic surgical system, or other computer system determines 1164 whether an image of the structure gathered by the imaging device, with the calculated 1162 settings set, is clear. If the image is determined 1164 to be clear, then automatic adjustment of the scope stops 1152 and the surgical procedure continues (invisible to the user). If the image is determined 1164 to not be clear, the blurred or distorted image is likely due to fluid or other matter obstructing the scope's lens. Thus, the surgical hub, robotic surgical system, or other computer system determines 1166 whether scope cleaning technology is installed on the scope. If scope cleaning technology is determined 1166 to not be installed, the surgical hub, robotic surgical system, or other computer system causes 1168 a user notification, e.g., a visual alert on a display, an audible announcement, etc., to be provided indicating that the scope must be removed and cleaned or be replaced with a different scope. In such an instance, the blurred or distorted image is likely due to fluid or other matter obstructing the scope's lens, and no scope cleaning technology is available on the scope to automatically clean the scope at the scope's current location in the patient. If scope cleaning technology is determined 1166 to be installed, the surgical hub, robotic surgical system, or other computer system activates 1170 the scope cleaning technology to clean the scope, such as by causing the scope's lens to be sprayed with cleaning fluid. After the activation 1170 of the scope cleaning technology, the first adjustment 1154 occurs again and the method 1140 continues as discussed above. If the surgical hub, robotic surgical system, or other computer system determines 1164 a second time that the image is not clear, the method 1140 can continue as discussed above or can instead proceed directly to causing 1168 a user notification since the previous cleaning was unsuccessful.

If the scope is determined 1146 to be in the optimal working range, the surgical hub, robotic surgical system, or other computer system adjusts 1154 the light source of the primary imaging system and the method 1140 continues as discussed above. If the surgical hub, robotic surgical system, or other computer system determines 1164 a second time that the image is not clear, the method 1140 can continue as discussed above or can instead proceed directly to causing 1168 a user notification since the previous cleaning was unsuccessful.

For yet another example, local imaging, such as multi-spectral light or ultrasound, can be used to adjust 3D constructs, mapping, or CT imaging based on identified deviations from a preoperative surgical plan or a preoperative scan to more up-to-date, higher precision, and/or improved imaging from a local imaging system. The local imaging can be used to adjust global imaging (e.g., a preoperative full body CT planned scan) or focused cone-beam CT intraoperative imaging based on changes, deviations, and/or irregularities identified locally using the local imaging. Examples of using an independent color cascade of illumination sources including visible light and light outside of the visible range to image one or more tissues within a surgical site at different times and at different depths, and using sequential laser light from differing sources to IR-R-B-G-UV coloration and determining properties of back scattered light and Doppler effect to track moving particles, are further described, for example, in U.S. Pat. Pub. No. 2019/0206050 entitled "Use Of Laser Light And Red-Green-Blue Coloration To Determine Properties Of Back Scattered Light" published Jul. 4, 2019, which is hereby incorporated by reference in its entirety.

In an exemplary embodiment, a contrasting agent can be introduced into a patient's physiologic system to highlight, fluoresce, or contrast anatomic structures intraoperatively. Contrast-enhanced ultrasound with microbubbles can be used, such as for blood perfusion in organs, thrombosis (such as in myocardial infraction), abnormalities in the heart, liver masses, kidney masses, inflammatory activity in inflammatory bowel disease, and a chemotherapy treatment response. Microbubble contrast materials are tiny bubbles of an injectable gas held in a supporting shell. The microbubble shells dissolve in the patient, usually within a range of about 10 minutes to about 15 minutes, and the gas is removed from the body through exhalation. As another example, indocyanine green (ICG) IT fluorescing can be used, such as for fluorescing blood vessels. As yet another example, barium sulfide and iodine, such as iodine-containing contrast medium (ICCM) can be used, such as for CT blood vessel imaging. As still another example, gadolinium can be used, such as for MRI imaging.

Figure 48:
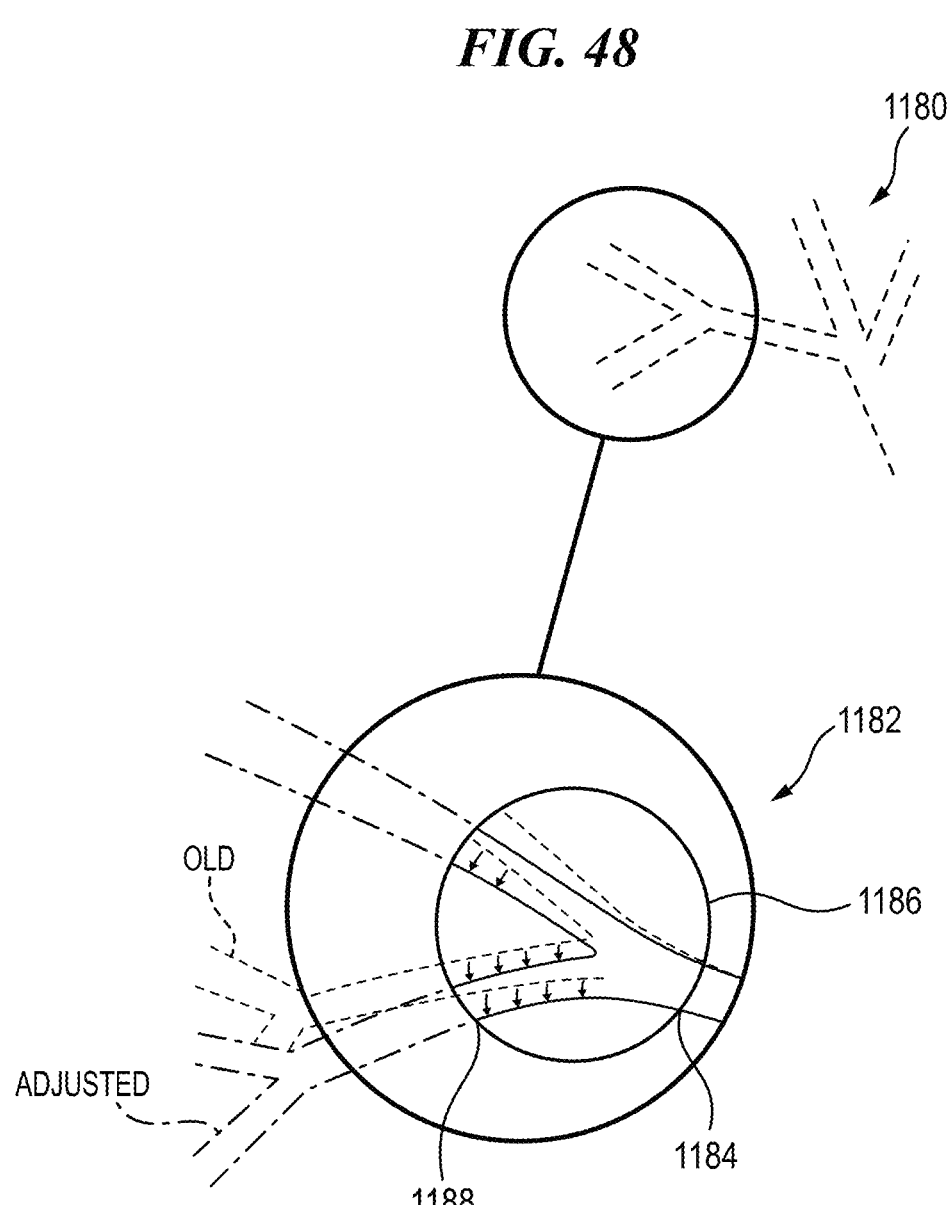
FIG. 48 is a schematic view of one embodiment of a display showing an on-the-fly adaptation of vascular CT with real-time local scanning.

FIG. 48 illustrates one embodiment of a display showing an on-the-fly adaptation of vascular CT with real-time local scanning. The display includes a preoperative CT scan 1180 showing anticipated vascular location. The display also includes an adaptive real time view 1182 that includes real-time local scanning. The adaptive real time view 1182 includes ICG real-time vascular imaging 1184 indicating real-time vascular location overlaid with the relevant area 1186 (shown via a first color dotted line) of the preoperative CT scan 1180 and overlaid with a real time realigned vascular imaging 1188 (shown via a second color dotted line) based on the local imaging 1184 and the preoperative CT scan 1180. The overlays are shown with differently colored dotted lines in this illustrated embodiment but can be indicated in other ways, such as by differently styled lines (dotted versus dashed, etc.) of a same color, differently styled lines of different colors, lines of different brightness, etc.

Controlling Cooperative Surgical Imaging Interactions

Devices, systems, and methods for multi-source imaging provided herein may allow for controlling cooperative surgical imaging interactions. In general, identifying, determining a location of, and determining an orientation of a first and second imaging systems relative to one another can allow for controlling cooperative surgical imaging interactions. In an exemplary embodiment, one of the first and second imaging systems can be identified and tracked by the other one of the imaging systems with the first and second imaging systems being positioned on opposite sides of a tissue wall such that the tissue wall provides an obstruction preventing the first and second imaging systems from seeing one another.

Figure 49:
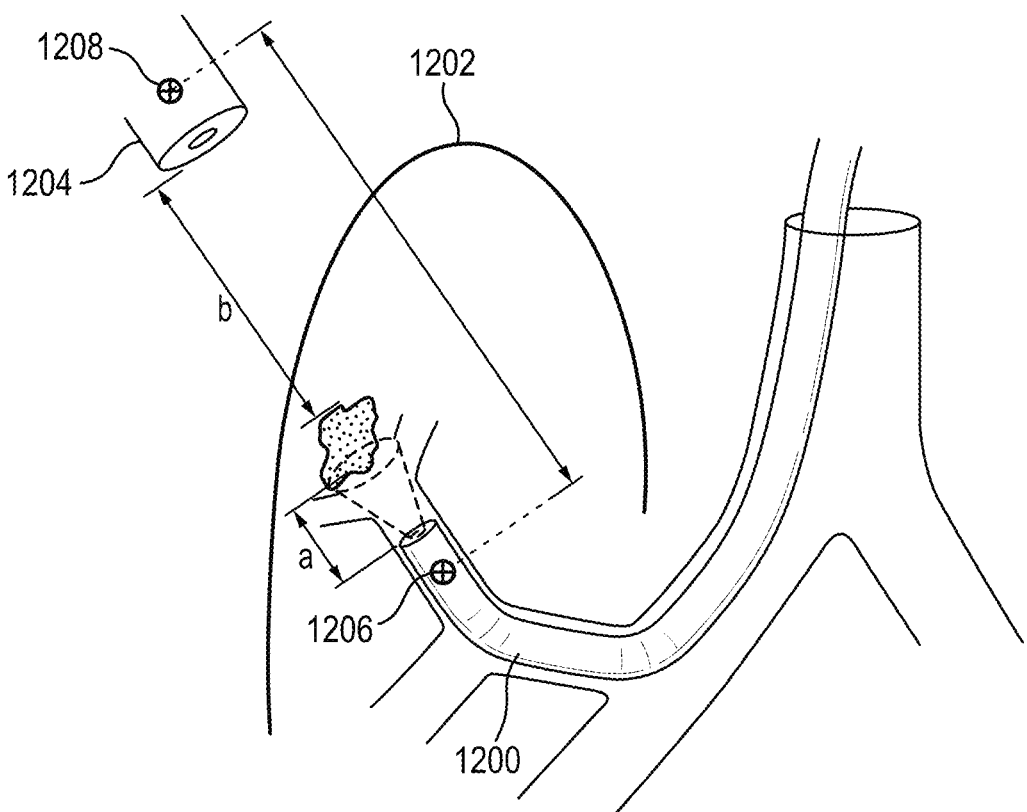
FIG. 49 is a schematic view of first and second imaging systems positioned relative to a tissue.

For example, a first imaging system located on a first side of a tissue wall can be configured to use magnetic sensing to detect a location of a second imaging system located on a second, opposite side of the tissue wall. FIG. 49 illustrates one embodiment of a first imaging system, including a flexible scope 1200, located on a first side of a tissue wall 1202 configured to use magnetic sensing to detect a location of a second imaging system, including a rigid scope 1204, located on a second, opposite side of the tissue wall 1202. The flexible scope 1200 includes a first magnetic fiducial marker 1206, and the rigid scope 1204 includes a second magnetic fiducial marker 1208. FIG. 49 illustrates a lung, but imaging systems can be located on opposite sides of a tissue wall of another anatomic structure. Various embodiments of magnetic fiducial markers and using magnetic fiducial markers in detecting location are discussed further, for example, in U.S. patent application Ser. No. 17/494,364 entitled "Surgical Methods For Control Of One Visualization With Another" filed on Oct. 5, 2021.

Figure 50:
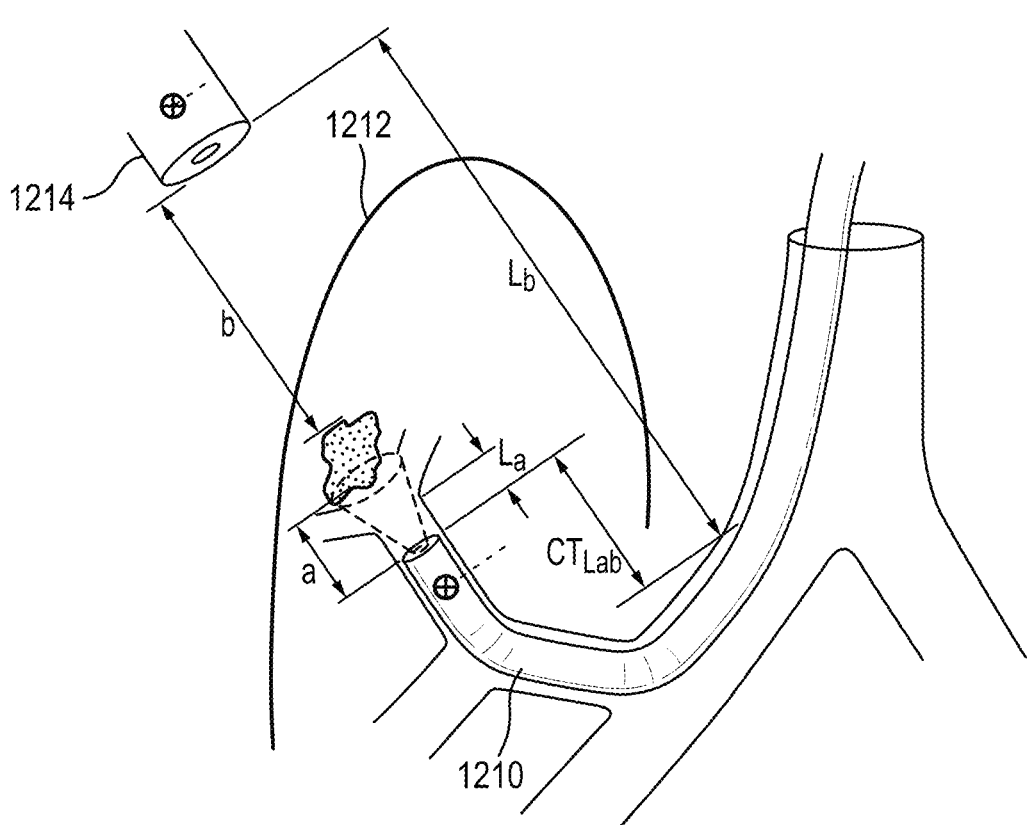
FIG. 50 is another schematic view of first and second imaging systems positioned relative to a tissue.

For another example, a first imaging system located on a first side of a tissue wall can be configured to use common anatomic landmarks to detect a location and orientation of a second imaging system located on a second, opposite side of the tissue wall. FIG. 50 illustrates one embodiment of a first imaging system, including a flexible scope 1210, located on a first side of a tissue wall 1212 and a rigid scope 1214, located on a second, opposite side of the tissue wall 1212.

For yet another example, a structured light scan can be used to create a 3D map. Electromagnetic tracking of a distal end of a first scope, e.g., using a fiducial marker such as the distal fiducial marker 1206 or the distal fiducial marker 1208, provides 3D registration of the map. A perimeter can then be created around a tumor or other critical structure using manual line or guides by confocal laser endomicroscopy to provide real time histology guidance. A line as registered in space can be communicated to a second scope located on an opposite side of a tissue wall as the first scope for pinch assist on the second scope's side of the tissue wall for submucosal resection or geofencing for full wall resection.

Figure 51:
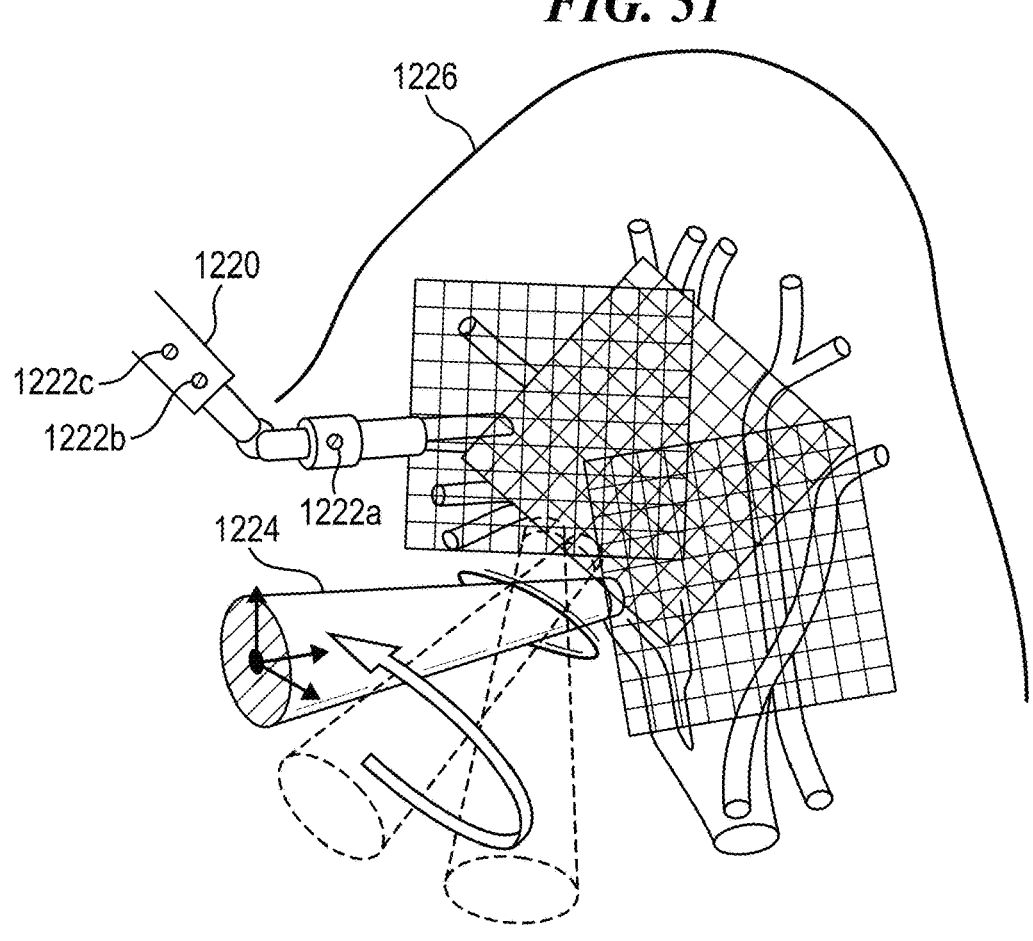
FIG. 51 is a perspective view of one embodiment of a surgical instrument including a plurality of fiducial markers.

For still another example, a surgical instrument can be tracked by an imaging system using a fiducial marker on the surgical instrument. Any number of surgical instruments can be tracked in this way during performance of a surgical procedure. FIG. 51 illustrates one embodiment of a surgical instrument 1220 that includes a fiducial marker 1222a, 1222b, 1222c. Three fiducial marker 1222a, 1222b, 1222c are used in this illustrated embodiment, but another number is possible. FIG. 51 shows a camera 1224 and the surgical instrument 1220 positioned relative to a lung 1226.

Figure 52:
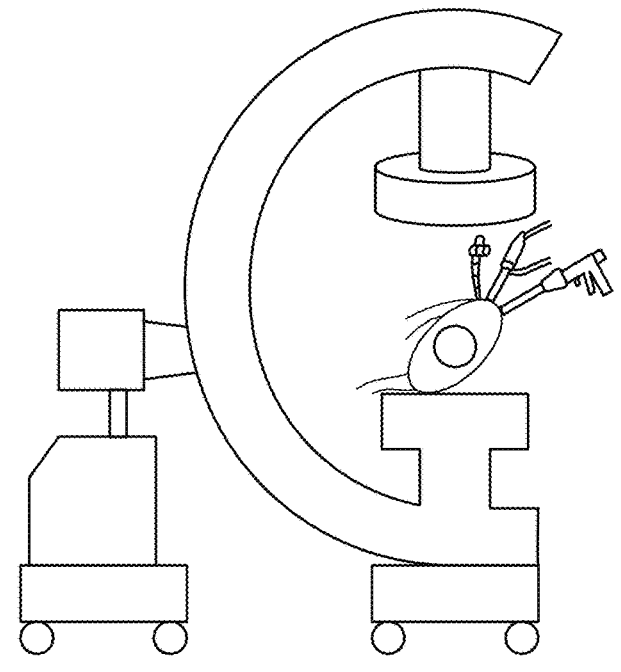
FIG. 52 is a schematic view of one embodiment of intraoperative C-arm CT imaging.

For another example, as shown in one embodiment in FIG. 52, intraoperative C-arm CT imaging can cooperate with flexible scope imaging to track a tumor or other critical structure for improved control in hard to access locations.

In some embodiments, controlling cooperative surgical imaging interactions includes using smart device location cooperatively with scope tracking. In general, a non-magnetic sensing system can be used for 3D tracking to provide X, Y, Z coordinates using a single receiver and at least one emitter. A time-of-flight distance sensor system, discussed above, may thus be used.

For example, the non-magnetic sensing system can include ultrasonic sensor technology and radiofrequency (RF) sensor technology. A time of flight system can include an emitter and a receiver. To facilitate controlling cooperative surgical imaging interactions, the emitter includes an ultrasonic sensor (ultrasonic beacon) configured to transmit ultrasonic pulses, and the receiver includes an RF receiver configured to transmit an RF signal that commands the emitter to begin transmitting the ultrasonic pulses. The ultrasonic pulses are reflected back by object(s) within their range. The RF receiver is configured to record the ultrasonic pulses and to, based on the recorded ultrasonic pulses, calculate 3D coordinates (X, Y, Z) of the emitter. The sound propagation time of the ultrasonic pulses allows the RF receiver to calculate the 3D coordinates and to calculate distance to objects.

Figure 53:
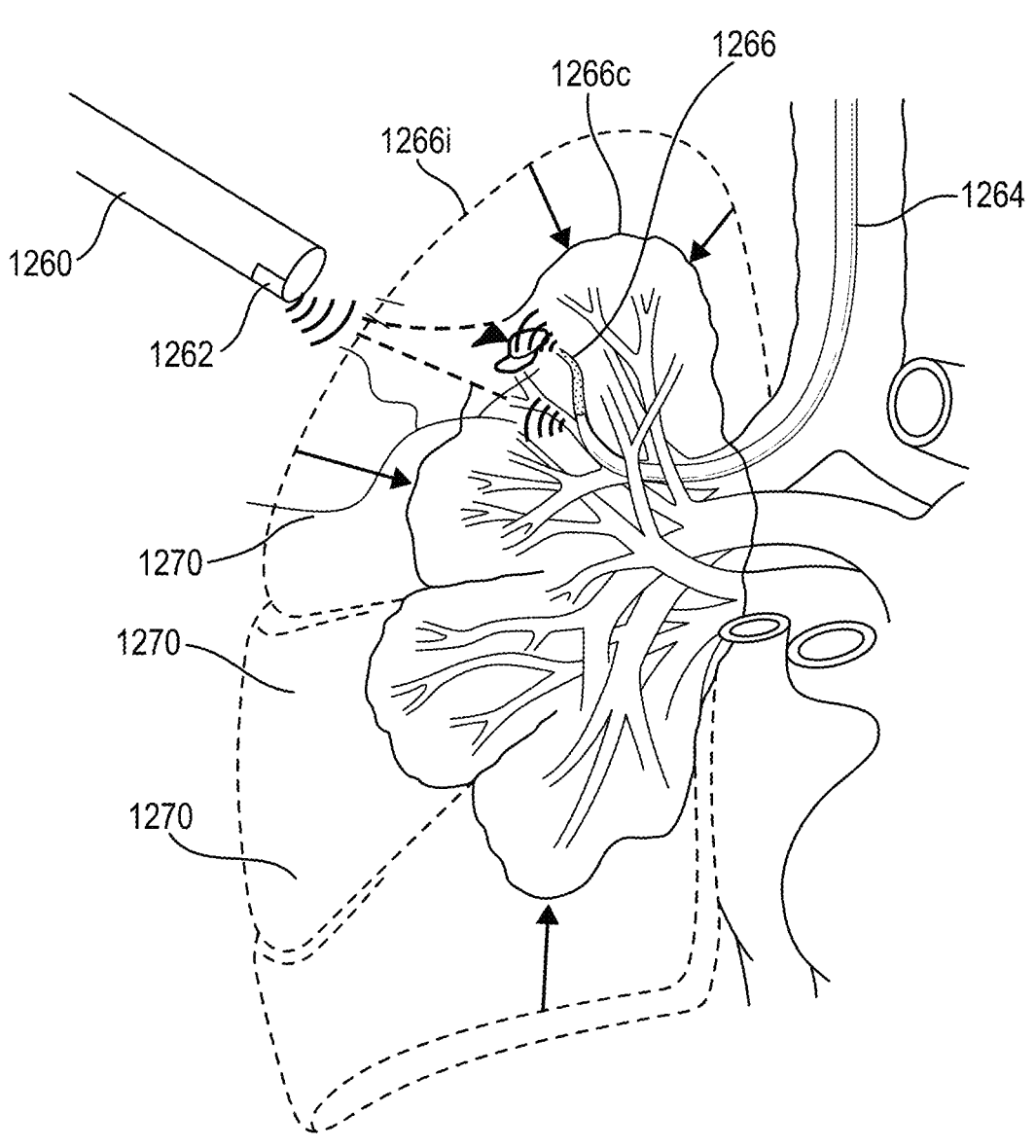
FIG. 53 is a schematic view of one embodiment of a camera and a scope positioned relative to a lung.

FIG. 53 illustrates one embodiment in which a camera 1260 includes a receiver 1262, a flexible scope 1264 includes a first ultrasonic sensor (obscured in FIG. 53), and a surgical instrument 1266 includes a second ultrasonic sensor (obscured in FIG. 53). The camera 1260 is positioned relative to a lung outside of the lung. The scope 1264 has been advanced into the lung and is positioned in the lung, and the instrument 1266 has been advanced through a working channel of the scope 1264 to extend distally out of the scope 1264. FIG. 53 shows the lung 1268$i$ in an inflated state (lung in dotted line) and shows the lung 1268$c$ in a collapsed state (lung in solid line), which illustrates a working space 1270 made available after lung collapse for, e.g., tools such as the camera 1260 to be effectively positioned in the patient. Arrows pointing inward in FIG. 53 indicate the lung collapse. 3D coordinates (X, Y, Z) can thus be calculated for the instrument 1266 and the scope 1264.

Controlling Power

Devices, systems, and methods for multi-source imaging provided herein may allow for controlling power. In general, controlling power can prevent an ablation device from applying too much power to tissue via an electrode of the ablation device, which can result in inadvertent collateral damage such as tissue wall perforation. The power output by an ablation device can be monitored, thereby allowing for the power control. Examples of ablation devices are Neu-Wave™ ablation probes (available from Ethicon US LLC of Cincinnati, OH). Another example of an ablation device is the Hyblate catheter ablation probe (available from Hyblate Medical of Misgav, Israel). Another example of an ablation device is the Barxx™ HaloFlex (available from Medtronic of Minneapolis, MN). Other examples of ablation devices are discussed further in, for example, U.S. patent application Ser. No. 17/494,364 entitled "Surgical Methods For Control Of One Visualization With Another" filed on Oct. 5, 2021.

After a laparoscopic portion of a segmentectomy (segment resection) has been completed, an ablation device can be advanced through a working channel of a flexible endoscope and used to ablate a tumor or other target tissue. The ablation device can be a radiofrequency (RF) cautery tool or a microwave ablation tool. Ablation devices can be used to ablate tissue in other types of surgical procedures as well.

The energy (power) of an ablation device can be controlled by visualizing thermal or therapeutic effects from an opposite side of a tissue wall from where the ablation device is applying the energy. FIG. 54 illustrates one embodiment in which the energy (power) of a microwave ablation device (probe) 1280 can be controlled by visualizing thermal or therapeutic effects from an opposite side of a tissue wall 1282, e.g., using an infrared (IR) thermal camera 1284 positioned outside the tissue wall 1282, from where the ablation device 1280 is applying the energy to a tumor 1286. The tissue wall 1282 is a lung wall in this illustrated embodiment, but thermal or therapeutic effects can be similarly visualized and used in controlling power in surgical procedures performed elsewhere, such as in a duodenal mucosal resurfacing procedure in which duodenal mucosa is ablated. Infrared images 1288 gathered by the IR thermal camera at four times $t_0$, $t_2$, $t_4$, to are shown in FIG. 54.

FIG. 54 also shows a graph indicating each of IR camera 1284 temperature (° C.), ablation probe 1280 position (cm), and ablation probe 1280 power level (W) versus time. As indicated in the graph, the IR thermal camera 1284 monitors the temperature of the ablation device's ablation zone (e.g., an area of ablation that an ablation device 1280 can create), which includes the tumor 1286 and a margin area around the tumor 1286 within the ablation zone. The times in the graph include the four times $t_0$, $t_2$, $t_4$, to for which IR images are shown.

The therapeutic temperature range for tissue ablation is in a range from about 60° C. to about 100° C. As shown in the graph, the power level is controlled so the tumor 1286 is being ablated within the therapeutic temperature range from a time between times $t_1$ and $t_2$ to when energy application stops shortly before time to between times $t_5$ and $t_6$. The temperature decreases from time $t_2$ and $t_3$, so the power level is increased at time $t_3$ to prevent the temperature from falling below about 60° C. The temperature increases from time $t_3$ and $t_4$, so the power level is decreased at time $t_4$ to prevent the temperature from rising above about 100° C. The temperature decreases again shortly before time $t_5$, so the power level is increased at time $t_5$ to prevent the temperature from falling below about 60° C.

Tissue being at a temperature up to about 41° C. can cause blood vessel dilation and increased blood perfusion and trigger a heat-shock response but have little long term effect. The tissue being at a temperature above about 41° C. makes the tissue susceptible to or causes the tissue to incur irreversible cell damage, with the higher the temperature corresponding to more damage. As shown in the graph, the power level is also controlled so the temperature of the healthy, non-target lung tissue in the ablation zone is kept below about 41° C. for as long as possible while maintaining effective ablation of the tumor 1286.

For yet another example, an ablation device can include a plurality of electrodes that are equally spaced about a center of the device. The plurality of electrodes are configured to move between a compressed configuration, which facilitates movement of the ablation device into and out of a patient, and an expanded configuration, which facilitates energy application to tissue by the electrodes that each contacts the tissue. Each of the electrodes is segmented and is configured to take initial impedance and temperature readings. One embodiment of such an ablation device 1290 is shown in FIG. 55, FIG. 56, and FIG. 57. FIG. 55 shows the ablation device 1290 in a compressed configuration in which the ablation device's electrodes extend linearly. FIG. 56 and FIG. 57 show the ablation device 1290 in an expanded configuration in which the electrodes are radially expanded. FIG. 57 also shows the ablation device 1290 advanced into position relative to a tumor 1292 through an endoscope 1294, with the electrodes advanced distally out of the ablation device's sheath 1290. The distal advancement of the electrodes out of the sheath 1296 (or proximal movement of the sheath 1296 relative to the electrodes) causes the electrodes to automatically radially expand. Correspondingly, proximal movement of the electrodes into the sheath 1296 (or distal movement of the sheath 1296 relative to the electrodes) causes the electrodes to automatically radially contract. In some embodiments, the sheath 1296 may be omitted such that movement of the electrodes into and out of the endoscope 1294 causes expansion and compression of the electrodes.

To facilitate power control, each of the electrodes can contact tissue on one side of a tissue wall. A camera, e.g., the IR thermal camera 1284 of FIG. 54, can be positioned on an opposite side of the tissue wall. The electrodes can then begin applying a low level of power to the tissue. These low level energy pulses can be used to align the camera to the precise area to be internally heated. The ablation device 1290 can share the electrodes' initial impedance and temperature readings, which can serve as a baseline. The electrodes can then begin applying therapeutic energy, with the power being controlled based on the thermal energy measured by the camera as discussed above, such as by adjusting at least one variable parameter of a control algorithm. Such an approach can be used in a bipolar or a monopolar configuration. Introducing saline between the mucosa and submucosa may help control the tissue heating to just the mucosa and to more specific depths by impedance monitoring. The ablation device 1290 can be rotated clockwise or counterclockwise such that the electrodes correspondingly rotate clockwise or counterclockwise, which may provide higher current density in the event that additional heating is required, such as if the tissue is not being heated to the therapeutic ablation temperature range.

Color of tissue adjacent to tissue being ablated can be monitored and used to control power. The color of tissue can be used to indicate either the heal of the tissue or the tissue's vascularization capacity. In general, a color change over time can indicate that ablation energy level should be adjusted.

Figure 58:
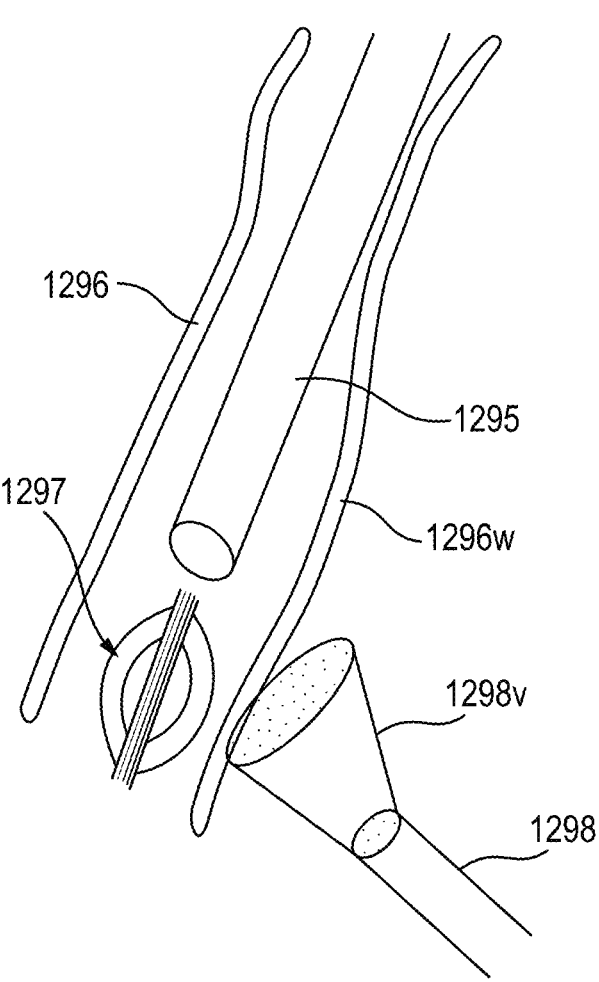
FIG. 58 is a schematic partially cross-sectional view of one embodiment of a tissue lumen having a flexible scope positioned therein and a laparoscope positioned outside thereof.

FIG. 58 illustrates one embodiment in which tissue color can be used to control power. A flexible scope 1295 has been advanced into a body lumen 1296. An ablation device 1297 has been advanced through a working channel of the scope 1295 to extend distally beyond the scope 1295 such that an expandable member 1297f of the ablation device 1297 has expanded radially. A laparoscope 1298 has been positioned outside the lumen 1296 so as to be positioned on an opposite side of a tissue wall 1296w (defined by the lumen 1296) than the scope 1295 and the ablation device 1297. A field of view 1298v is shown for the laparoscope 1298. Before the ablation device 1297 begins applying energy to the tissue via an electrode (which can be one or more electrodes) of the ablation device 1297, the laparoscope 1298 establishes an average color scale for tissue within its field of view 1298w, within which energy will be applied on the other side of the tissue wall 1296w. Thereafter, as energy is applied to the tissue via the electrode and the tissue is cooked from the inside, the tissue will tend to change color by becoming lighter. For example, the average color scale of tissue can be a pinkish red, and the energy application can cause the tissue to lighten to a lighter pinkish red or to a whitish shade. As the tissue changes color during energy application, and the laparoscope 1298 continues to monitor the tissue color, the laparoscope 1298 can trigger the energy level to change, e.g., providing a signal to a surgical hub, robotic surgical system, or other computer system also in communication with the ablation device 1297 that triggers a change in at least one variable parameter, in response to the color reaching a predetermined light shade. There may be a plurality of predetermined light shades, each corresponding to a different energy control change. The change in energy level may be moving to an energy level of zero so as to stop energy delivery, as the tissue color change may indicate that the tissue is being coagulated such that energy application should be stopped. Additionally, bubbling, effects of escaping steam, or effects of higher temperature fluids on adjacent tissue(s) can be monitored, either directly or by monitoring the effects on the adjacent tissue(s).

Figure 59:
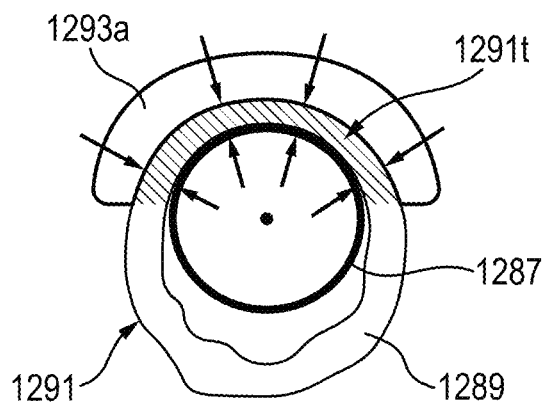
FIG. 59 is a schematic cross-sectional view of one embodiment of a flexible force probe pressing on a tissue wall in which a scope is positioned.
Figure 60:
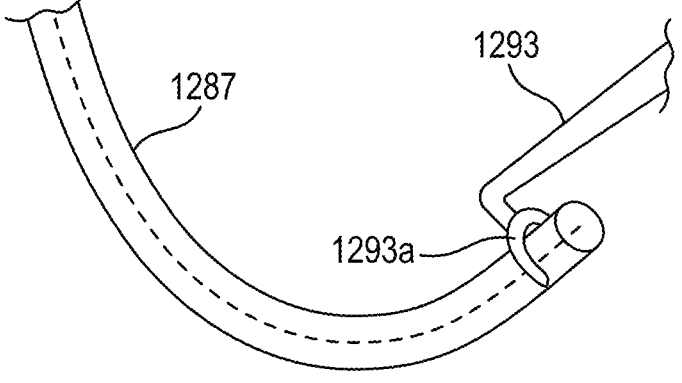
FIG. 60 is a perspective view of the probe and the scope of FIG. 59.

In some embodiments in which tissue is ablated, a flexible force probe can be used to help keep a consistent thickness of tissue, which may help ensure that the tissue eventually ablated has a consistent thickness. Consistent thickness generally helps ensure consistent heating of the tissue. FIG. 59 and FIG. 60 illustrate one embodiment of a flexible force probe 1293 configured to apply force to a tissue wall 1291 from one side of the tissue wall 1291, which in this illustrated embodiment is outside of a body lumen 1289 in which a scope 1287 is positioned. The lumen 1289 is not shown in FIG. 60. The flexible force probe 1293 includes an arm 1293a configured to abut and press against the tissue wall 1291. The arm 1293a can be flexible to allow the arm 1293a to conform to the shape of the tissue wall 1291. With the scope 1287 positioned on the opposite side of the tissue wall 1291 while the arm 1293a is pressing against the tissue wall 1291, a thickness 1291t of the tissue wall 1291 can be controlled to a consistent thickness. Since the internal path of the scope 1287 is known within the lumen 1289, the probe 1293 external to the lumen 1289 can follow the same spline path with the arm 1293a pressing on the tissue wall 1291 to control the tissue thickness 1291t.

In some embodiments in which tissue is ablated using an ablation device, visualization can be used to monitor either collateral effects of the ablation device's energy application or the active intentional use of the ablation device near critical structure(s). The monitoring may help prevent inadvertent damage. The monitoring can include monitoring a location of the ablation device and data communicated from the ablation device indicating that the ablation device is active (e.g., is applying energy), monitoring tissue temperature, monitoring color of ejected steam, and/or monitoring effects caused by the ablation device. The monitoring can serve a means to compare the ablation device's affected ablation zone to surrounding critical structure(s) location and sensitivity. For example, multi-spectral imaging can be used to detect a ureter in proximity to a location where the ablation device is applying energy and to trigger the ablating to stop if the ablation zone becomes within a threshold distance of the ureter.

Devices and systems disclosed herein can be designed to be disposed of after a single use, or they can be designed to be used multiple times. In either case, however, the devices can be reconditioned for reuse after at least one use. Reconditioning can include any combination of the steps of disassembly of the devices, followed by cleaning or replacement of particular pieces, and subsequent reassembly. In particular, the devices can be disassembled, and any number of the particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

It can be preferred that devices disclosed herein be sterilized before use. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 issued Feb. 14, 2012 and entitled "System And Method Of Sterilizing An Implantable Medical Device." It is preferred that device, if implanted, is hermetically sealed. This can be done by any number of ways known to those skilled in the art.

The present disclosure has been described above by way of example only within the context of the overall disclosure provided herein. It will be appreciated that modifications within the spirit and scope of the claims may be made without departing from the overall scope of the present disclosure. All publications and references cited herein are expressly incorporated herein by reference in their entirety for all purposes.

What is claimed is:

1. A surgical method, comprising:

visualizing, with a rigid scoping device located outside of an organ, a first side of a tissue wall during performance of a surgical procedure, the rigid scoping device being thoracoscopic or laparoscopic;

visualizing, with a flexible scoping device advanced into the organ, a second, opposite side of the tissue wall during the performance of the surgical procedure, the rigid scoping device and the flexible scoping device being unable to directly visualize each other, wherein at least one of the rigid scoping device or the flexible scoping device is configured to emit a structured light pattern via a structured light emitter, emit a spectral light via a spectral light emitter, and detect a reflected structured light pattern and reflected spectral light via an image sensor;

generating a 3D map based on a visualization provided by the rigid scoping device and a visualization provided by the flexible scoping device;

guiding a first surgical instrument based on the visualization provided by the rigid scoping device and the visualization provided by the flexible scoping device, and based on a location of the first surgical instrument on the 3D map; and guiding a second surgical instrument based on the visualization provided by the flexible scoping device and based on the visualization provided by the rigid scoping device.

2. The method of claim 1, wherein at least one of the first surgical instrument or the second surgical instrument identifies a location of the at least one first surgical instrument or the second surgical instrument; and the method further comprises communicating the location to a first imaging system and an endoscopic imaging system so as to provide secondary location verification on the 3D map to the first imaging system and the endoscopic imaging system.

3. The method of claim 1, further comprising determining, with a first imaging system that includes the rigid scoping device, a location and orientation of the second surgical instrument relative to the first surgical instrument to facilitate the first surgical instrument being guided based on the visualization provided by the flexible scoping device; and determining, with an endoscopic imaging system that includes the flexible scoping device, a location and orientation of the first surgical instrument relative to the second surgical instrument to facilitate the second surgical instrument being guided based on the visualization provided by the rigid scoping device.

4. The method of claim 1, further comprising visualizing, with each of the rigid scoping device and the flexible scoping device, a common anatomic landmark and thereby facilitate guiding of the first and second surgical instruments relative to one another.

5. The method of claim 1, further comprising visualizing, with a computerized tomography (CT) imaging system, the first and second instruments and thereby facilitate guiding of the first and second surgical instruments relative to one another.

6. The method of claim 1, further comprising gathering, using at least one of ultrasonic energy and radiofrequency (RF) energy, data indicative of a location of the first and second surgical instruments and thereby facilitate guiding of the first and second surgical instruments relative to one another.

7. The method of claim 1, wherein the first and second surgical instruments are each releasably coupled to a robotic surgical system that controls the guiding of each of the first and second surgical instruments.

8. The method of claim 1, wherein the rigid scoping device is a thoracoscopic device, the organ is a lung, and the flexible scoping device is advanced transorally into the lung.

9. The method of claim 1, wherein the rigid scoping device is a laparoscopic device, the organ is a stomach or an intestine, and the flexible scoping device is advanced transorally into the stomach or the intestine.

10. The method of claim 1, wherein the first and second surgical instruments are each releasably coupled to a robotic surgical system operatively coupled to a plurality of surgical hubs; and one of the surgical hubs controls the guiding of each of the first and second surgical instruments.

11. A surgical method, comprising:

visualizing, with a first imaging system, a first side of a tissue wall during performance of a surgical procedure, the first imaging system being a thoracoscopic imaging system or a laparoscopic imaging system;

visualizing, with an endoscopic imaging system, a second, opposite side of the tissue wall during the performance of the surgical procedure, the first imaging system and the endoscopic imaging system being unable to directly visualize each other, and the first imaging system and the endoscopic imaging system being operatively coupled together;

guiding a first surgical instrument based on the visualization provided by the first imaging system and the visualization provided by the endoscopic imaging system; and guiding a second surgical instrument based on the visualization provided by the endoscopic imaging system and based on the visualization provided by the first imaging system;

wherein one of the first imaging system and the endoscopic imaging system includes a structured light emitter configured to emit a structured light pattern on a surface of an organ, a spectral light emitter configured to emit spectral light in a plurality of wavelengths capable of penetrating the organ and reaching an internal aspect located below the surface of the organ, and an image sensor configured to detect reflected structured light pattern, reflected spectral light, and reflected visible light; and the surgical method further comprises constructing, with a controller, a three-dimensional (3D) digital representation of the organ from the reflected structured light pattern detected by the image sensor, detecting, with the controller, the internal aspect from the reflected spectral light detected by the image sensor, integrating, with the controller, the internal aspect with the 3D digital representation of the organ, and causing, with the controller, a display device to show the internal aspect and a 3D rendering of the organ based on the 3D digital representation of the organ.

12. The method of claim 11, wherein at least one of the first and second surgical instruments identifies a location of the at least one first surgical instrument and second surgical instrument; and the method further comprises communicating the location to the first imaging system and the endoscopic imaging system so as to provide secondary location verification to the first imaging system and the endoscopic imaging system.

13. The method of claim 11, further comprising determining, with the first imaging system, a location and orientation of the second surgical instrument relative to the first surgical instrument to facilitate the first surgical instrument being guided based on the visualization provided by the endoscopic imaging system; and determining, with the endoscopic imaging system, a location and orientation of the first surgical instrument relative to the second surgical instrument to facilitate the second surgical instrument being guided based on the visualization provided by the first imaging system.

14. The method of claim 11, further comprising visualizing, with each of the first imaging system and the endoscopic imaging system, a common anatomic landmark and thereby facilitate guiding of the first and second surgical instruments relative to one another.

15. The method of claim 11, further comprising visualizing, with a computerized tomography (CT) imaging system, the first and second instruments and thereby facilitate guiding of the first and second surgical instruments relative to one another.

16. The method of claim 11, further comprising gathering, using at least one of ultrasonic energy and radiofrequency (RF) energy, data indicative of a location of the first and second surgical instruments and thereby facilitate guiding of the first and second surgical instruments relative to one another.

17. The method of claim 11, wherein the first and second surgical instruments are each releasably coupled to a robotic surgical system that controls the guiding of each of the first and second surgical instruments.

18. The method of claim 11, wherein the first and second surgical instruments are each releasably coupled to a robotic surgical system operatively coupled to a plurality of surgical hubs; and one of the surgical instruments controls the guiding of each of the first and second surgical instruments.

19. The method of claim 11, wherein the first imaging system includes a rigid scoping device; and the endoscopic imaging system includes a flexible scoping device.

* * * * *